(12) United States Patent
Lakowicz et al.

(10) Patent No.: US 10,107,807 B2
(45) Date of Patent: *Oct. 23, 2018

(54) ONE DIMENSIONAL PHOTONIC CRYSTALS FOR ENHANCED FLUORESCENCE BASED SENSING, IMAGING AND ASSAYS

(71) Applicants: Joseph R. Lakowicz, Ellicott City, MD (US); Ramachandram Badugu, Ellicott City, MD (US)

(72) Inventors: Joseph R. Lakowicz, Ellicott City, MD (US); Ramachandram Badugu, Ellicott City, MD (US)

(73) Assignee: The University of Maryland, Baltimore, Baltimore, MD (US)

( * ) Notice: Subject to any disclaimer, the term of this patent is extended or adjusted under 35 U.S.C. 154(b) by 567 days.

This patent is subject to a terminal disclaimer.

(21) Appl. No.: 14/718,464

(22) Filed: May 21, 2015

(65) Prior Publication Data
US 2015/0338345 A1   Nov. 26, 2015

Related U.S. Application Data

(60) Provisional application No. 62/001,653, filed on May 22, 2014.

(51) Int. Cl.
*G01N 33/551*   (2006.01)
*G01N 33/543*   (2006.01)
(Continued)

(52) U.S. Cl.
CPC ... *G01N 33/54373* (2013.01); *G01N 21/6445* (2013.01); *G01N 21/7703* (2013.01);
(Continued)

(58) Field of Classification Search
None
See application file for complete search history.

(56) References Cited

U.S. PATENT DOCUMENTS

| | | | | |
|---|---|---|---|---|
| 2008/0225293 A1* | 9/2008 | Ye | ...................... | G01N 21/6408 356/364 |
| 2010/0065732 A1* | 3/2010 | Ye | .......................... | B82Y 20/00 250/281 |
| 2012/0258549 A1* | 10/2012 | Lu | ...................... | G01N 21/6428 436/501 |

OTHER PUBLICATIONS

Lakowicz, J., et al., "Radiative Decay Engineering 2. Effects of Silver Island Films on Fluorescence Intensity, Lifetimes, and Resonance Energy Transfer", Analytical Biochemistry, Jan. 15, 2002, pp. 261-277, vol. 301, Publisher: Elsevier Science, Published in: doi:10.1006/abio.2001.5503.

(Continued)

*Primary Examiner* — Christopher L Chin
(74) *Attorney, Agent, or Firm* — Eugene J. Molinelli; Beusse Wolter Sanks & Maire

(57) ABSTRACT

Techniques for enhanced fluorescence include a functionalized substrate for a target optical frequency comprising a one dimensional photonic crystal that is functionalized with a bioactive target molecule that has an affinity for a particular analytic. The one dimensional photonic crystal includes a plurality of dielectric layers including a plurality of high index of refraction layers alternating with a plurality of low index of refraction layers. The thickness of each layer is within a factor of four of a wavelength of the optical frequency in the layer. For emissions from a fluorophore bound to the target molecule and excited by incident light, there is an emission intensity maximum centered at an angle independent of the direction of the incident light.

34 Claims, 22 Drawing Sheets

(51) Int. Cl.

| | |
|---|---|
| *G01N 33/552* | (2006.01) |
| *G02B 1/00* | (2006.01) |
| *G01N 21/64* | (2006.01) |
| *G02B 5/00* | (2006.01) |
| *G01N 21/77* | (2006.01) |
| *G02B 6/122* | (2006.01) |
| *G01N 33/58* | (2006.01) |

(52) U.S. Cl.
CPC ......... *G01N 33/551* (2013.01); *G01N 33/552* (2013.01); *G01N 33/58* (2013.01); *G02B 1/005* (2013.01); *G02B 5/008* (2013.01); *G02B 6/1225* (2013.01); *G01N 2021/7786* (2013.01)

(56) References Cited

OTHER PUBLICATIONS

Lakowicz, J., "Radiative decay engineering 3. Surface plasmon-coupled directional emission", Anal. Biochem., Jan. 15, 2004, pp. 153-169, vol. 324, No. 2, Publisher: NIH Public Access, Published in: doi:10.1016/j.ab.2003.09.039.

Lakowicz, J., "Radiative decay engineering 5. metal-enhanced fluorescence and plasmon emission", Analytical Biochemistry, Dec. 13, 2014, pp. 171-194, vol. 337, Publisher: Elsevier, Published in: doi:10.1016/j.ab.2004.11.026.

Lakowicz, J., et al., "Plasmon-controlled fluorescence: a new paradigm in fluorescence spectroscopy", Analyst, Jul. 16, 2008, pp. 1308-1346, vol. 133, Publisher: Royal Society of Chemistry, Published in: DOI: 10.1039/b802918k.

Leistikow, M. D., et al., "Inhibited Spontaneous Emission of Quantum Dots Observed in a 3D Photonic Band Gap", Phys Rev Lett, Nov. 4, 2011, pp. 1-5, vol. 107, No. 193903, Publisher: American Physical Society, Published in: http://dx.doi.org/10.1103/PhysRevLett.107.193903.

Liscidini, M., et al., "Enhancement of diffraction for biosensing applications via Bloch surface waves", Appl. Phys. Lett., Dec. 21, 2007, pp. 253125 1-4, vol. 91, No. 25, Publisher: American Institute of Physics, Published in: http://dx.doi.org/10.1063/1.2826545.

Liscidini, M., et al., "Analysis of Bloch-surface-wave assisted diffraction-based biosensors", J. Opt. Soc. Am. B, Feb. 1, 2009, pp. 279-289, vol. 26, No. 2, Publisher: Optical Society of America, Published in: doi: 10.1364/JOSAB.26.000279.

Lodahl, P., et al., "Controlling the dynamics of spontaneous emission from quantum dots by photonic crystals", Nature, Aug. 5, 2004, pp. 654-657, vol. 430, No. 7000, Publisher: Nature Publishing Group, Published in: doi:10.1038/nature02772.

Meade, R., et al., "Electromagnetic Bloch waves at the surface of a photonic crystal", Physical Review B, Nov. 15, 1991, pp. 44-49, vol. 44, No. 19, Publisher: APS Physics, Published in: http://dx.doi.org/10.1103/PhysRevB.44.10961.

Michelotti, F., et al., "Probing losses of dielectric multilayers by means of Bloch surface waves", Optics Letters, Feb. 21, 2013, pp. 616-618, vol. 38, No. 5, Publisher: OSA Publishing, Published in: doi: 10.1364/OL.38.000616.

Nair, R., et al., "Photonic crystal sensors: An overview", Progress in Quantum Electronics, May 1, 2010, pp. 89-134, vol. 34, No. 3, Publisher: Elsevier, Published in: doi:10.1016/j.pquantelec.2010.01.001.

Nikolaev, I., et al, Fluorescence Lifetime of Emitters with Broad Homogeneous Linewidths Modified in Opal Photonic Crystals, The Journal of Physical Chemistry C, Jan. 28, 2008, pp. 7250-7254, vol. 112, No. 18, Publisher: ACS Publications, Published in: http://pubs.acs.org/doi/abs/10.1021/jp7111439.

Nikolaev, I., et al., "Accurate calculation of the local density of optical states in inverse-opal photonic crystals," Journal of the Optical Society of America B, Feb. 11, 2009, pp. 987-997, vol. 26, No. 5, Publisher: OSA Publishing, Published in: doi: 10.1364/JOSAB.26.000987.

Norton, S., et al, "Plasmonics Quenching and Enhancement of a Fluorescing Molecule Outside and Inside a Silver Metallic Nanoshell", IEEE Transactions on Nanotechnology, Mar. 10, 2011, pp. 1264-1274, vol. 10, No. 6, Publisher: IEEE, Published in: http://ieeexplore.ieee.org/xpl/login.jsp?tp=&arnumber=5727961&url=http%3A%2F%2Fieeexplore.ieee.org%2Fxpls%2Fabs_all.jsp%3Farnumber%3D5727961.

Paeder, V., et al., "Detection of protein aggregation with a Bloch surface wave based sensor", Sensors and Actuators B: Chemical, Sep. 20, 2011, pp. 260-264, vol. 157, No. 1, Publisher: Elsevier, Published in: doi:10.1016/j.snb.2011.03.060.

Ramos-Mendieta, F., et al., "Surface electromagnetic waves in two-dimensional photonic crystals: Effect of the position of the surface plane", Physical Review B, Aug. 15, 1999, pp. 15112-15120, vol. 59, No. 23, Publisher: APS Physics, Published in: http://dx.doi.org/10.1103/PhysRevB.59.15112.

Ray, K., et al., "Aluminum Nanostructured Films as Substrates for Enhanced Fluorescence in the Ultraviolet-Blue Spectral Region", Analytical Chemistry, Aug. 8, 2007, pp. 6480-6487, vol. 79, No. 17, Publisher: ACS Publications, Published in: DOI: 10.1021/ac071363I.

Ricciardi, C., et al., "Amorphous Silicon Nitride: a suitable alloy for optical multilayered structures", Journal of Non-Crystalline Solids, Jun. 15, 2006, pp. 1294-1297, vol. 352, No. 9-20, Publisher: Elsevier, Published in: http://dx.doi.org/10.1016/j.jnoncrysol.2005.10.056.

Rivolo, P., et al., "Real time secondary antibody detection by means of silicon-based multilayers sustaining Bloch surface waves", Sensors and Actuators B: Chemical, Jan. 3, 2012, pp. 1046-1052, vol. 161, No. 1, Publisher: Elsevier, Published in: http://dx.doi.org/10.1016/j.snb.2011.12.006.

Rong, G., et al., "Resolving Sub-Diffraction Limit Encounters in Nanoparticle Tracking Using Live Cell Plasmon Coupling Microscopy", Nano Letters, Sep. 13, 2008, pp. 3386-3393, vol. 8, No. 10, Publisher: ACS Publications, Published in: DOI: 10.1021/nl802058q.

Schadt, E., et al., "A window into third-generation sequencing", Human Molecular Genetics, Sep. 21, 2010, pp. R227-R240, vol. 19, No. 2, Publisher: Oxford Journals, Published in: doi:10.1093/hmg/ddq416.

Sfez, T., et al., "Two-dimensional optics on silicon nitride multilayer: Refraction of Bloch surface waves", Applied Physics Letters, Apr. 12, 2010, pp. 151101, vol. 96, No. 15, Publisher: AIP Publishing, Published in: http://dx.doi.org/10.1063/1.3385729.

Sinibaldi, A., et al., "Hydrogenated amorphous silicon nitride photonic crystals for improved-performance surface electromagnetic wave biosensors", Biomedical Optics Express, Sep. 6, 2012, pp. 2405-2410, vol. 3, No. 10, Publisher: OSA Publishing, Published in: doi: 10.1364/BOE.3.002405.

Sinibaldi, A., et al., "Direct comparison of the performance of Bloch surface wave and surface plasmon polariton sensors", Sensors and Actuators B: Chemical, Aug. 18, 2012, pp. 292-298, vol. 174, Publisher: Elsevier, Published in: http://dx.doi.org/10.1016/j.snb.2012.07.015.

Spirk, R., et al., "Optical emission in periodic dielectrics", Europhysics Letters, Aug. 1, 1996, pp. 265-270, vol. 35, No. 4, Publisher: IOP Publishing, Published in: http://iopscience.iop.org/article/10.1209/epl/i1996-00564-y/meta.

Su, S., et al., "Optical surface edge Bloch modes: low-loss subwavelength-scale two-dimensional light localization", Optics Letters, Oct. 19, 2012, pp. 4398-4400, vol. 37, No. 21, Publisher: OSA Publishing, Published in: doi: 10.1364/OL.37.004398.

Sukhoivanov, I.A., et al., "Photonic density of states maps for design of photonic crystal devices", Microelectronics Journal, Mar. 31, 2008, pp. 685-689, vol. 39, No. 3-4, Publisher: Elsevier, Published in: doi:10.1016/j.mejo.2007.07.091.

Szmacinski, Henryk, et al., "Time-Resolved Fluorometric Method for One-Step Immunoassays Using Plasmonic Nanostructures", Journal of Physical Chemistry C, Dec. 15, 2009, pp. 7236-7241, vol. 114, No. 16, Publisher: ACS Publications, Published in: DOI: 10.1021/jp906743m.

(56) References Cited

OTHER PUBLICATIONS

Tang, Fu, et al, "Control of Metal-Enhanced Fluorescence with pH- and Thermoresponsive Hybrid Microgels", Langmuir, Nov. 8, 2011, pp. 883-888, vol. 28, No. 1, Publisher: ACS Publications, Published in: DOI: 10.1021/la203704j.

Thongrattanasiri, S., et al., "Analytical technique for subwavelength far field imaging", Applied Physics Letters, Sep. 7, 2010, pp. 101103, vol. 97, No. 10, Publisher: AIP Publishing, Published in: doi:10.1063/1.3487779.

Vats, N., et al., "Theory of fluorescence in photonic crystals", Physical Review A, Mar. 21, 2002, pp. 043808, vol. 65, No. 4, Publisher: APS Physics, Published in: DOI: 10.1103/PhysRevA.65.043808.

Vedantam, S., et al., "A Plasmonic Dimple Lens for Nanoscale Focusing of Light", Nano Letters, Sep. 9, 2009, pp. 3447-3452, vol. 9, No. 10, Publisher: ACS Publications, Published in: DOI: 10.1021/nl9016368.

Velev, O., et al., "Materials Fabricated by Micro- and Nanoparticle Assembly The Challenging Path from Science to Engineering", Advanced Materials, Feb. 27, 2009, pp. 1897-1905, vol. 21, No. 19, Publisher: Wiley, Published in: DOI: 10.1002/adma.200801837.

Wagner, Rebecca, et al., "Back focal plane imaging spectroscopy of photonic crystals", Applied Physics Letters, Aug. 21, 2012, pp. 081904, vol. 101, No. 8, Publisher: AIP Publishing, Published in: http://dx.doi.org/10.1063/1.4746251.

Yablonovitch, E., "Inhibited Spontaneous Emission in Solid-State Physics and Electronics", Physical Review Letters, May 18, 1987, pp. 2059-2062, vol. 58, No. 20, Publisher: APS Physics, Published in: http://journals.aps.org/prl/abstract/10.1103/PhysRevLett.58.2059.

Ye, J., et al., "Enhancement of two-photon excited fluorescence using one-dimensional photonic crystals", Applied Physics Letters, Dec. 6, 1999, pp. 3605-3607, vol. 75, No. 23, Publisher: AIP Publishing, Published in: http://dx.doi.org/10.1063/1.125402.

Ye, J., et al., "Enhancing fluorescence detection with a photonic crystal structure in a total-internal-reflection configuration", Optics Letters, Aug. 1, 2008, pp. 1729-1731, vol. 33, No. 15, Publisher: OSA Publishing, Published in: doi: 10.1364/OL.33.001729.

Zhang, Y., et al., "Metal-enhanced fluorescence from copper substrates", Applied Physics Letters, Apr. 25, 2007, pp. 173116, vol. 90, No. 17, Publisher: AIP Publishing, Published in: http://dx.doi.org/10.1063/1.2732185.

Zhang, Y., et al., "Broad Wavelength Range Metal-Enhanced Fluorescence Using Nickel Nanodeposits", The Journal of Physical Chemistry C, Aug. 18, 2009, pp. 15811-15816, vol. 113, No. 36, Publisher: ACS Publications, Published in: DOI: 10.1021/jp900958n.

Zhang, J., et al., "Detection of CXCR4 receptors on cell surface using a fluorescent metal nanoshell", Journal of Biomedical Optics, Jan. 18, 2011, pp. 016011, vol. 16, No. 1, Publisher: SPIE, Published in: doi:10.1117/1.3528623.

Zhao J. "Localized surface plasmon resonance biosensors", Nanomedicine, Aug. 1, 2006, pp. 219-228, vol. 1, No. 2, Publisher: Future Medicine, Published in: DOI 10.2217/17435889.1.2.219.

Zhou, L., et al., "Enhancement of Immunoassays Fluorescence and Detection Sensitivity Using Three-Dimensional Plasmonic Nano-Antenna-Dots Array", Analytical Chemistry, Apr. 20, 2012, pp. 4489-4495, vol. 84, No. 10, Publisher: ACS Publications, Published in: DOI: 10.1021/ac3003215.

Zhu, Y., et al., "Highly modified spontaneous emissions in YVO4:Eu3+ inverse opal and refractive index sensing application", Applied Physics Letters, Feb. 21, 2012, pp. 081104, vol. 100, No. 8, Publisher: AIP Publishing, Published in: http://dx.doi.org/10.1063/1.3688167.

Akbay, N., et al., "Metal-enhanced intrinsic fluorescence of nucleic acids using platinum nanostructured substrates", Chemical Physics Letters, Aug. 16, 2012, pp. 45-50, vol. 548, Publisher: Elsevier, Published in: http://dx.doi.org/10.1016/j.cplett.2012.08.020.

Alexeev, V., et al., "High Ionic Strength Glucose-Sensing Photonic Crystal", Analytical Chemistry, May 15, 2003, pp. 2316-2323, vol. 75, No. 10, Publisher: American Chemical Society, Published in: pubs.acs.org/doi/abs/10.1021/ac030021m.

Angelini, A., et al., "Fluorescence diffraction assisted by Bloch surface waves on a one-dimensional photonic crystal", New Journal of Physics, Jul. 2, 2013, pp. 1-13, vol. 15, Publisher: IOP Publishing Ltd. & Deutsche Physikalische Gesellschaft, Published in: doi:10.1088/1367-2630/15/7/073002.

Badugu, R., et al., "Radiative decay engineering 6: Fluorescence on one-dimensional photonic crystals", Analytical Biochemistry, Jul. 27, 2013, pp. 83-96, vol. 442, Publisher: Elsevier, Published in: http://dx.doi.org/10.1016/j.ab.2013.07.021.

Badugu, R., et al., "Radiative decay engineering 7: Tamm state-coupled emission using a hybrid plasmonicphotonic structure", Analytical Biochemistry, Oct. 14, 2013, pp. 1-13, vol. 445, Publisher: Elsevier, Published in: http://dx.doi.org/10.1016/j.ab.2013.10.009.

Ballarini, M., et al., "Bloch surface waves-controlled emission of organic dyes grafted on a one-dimensional photonic crystal", Applied Physics Letters, Jul. 27, 2011, pp. 1-4, vol. 99, Publisher: American Institute of Physics, Published in: http://dx.doi.org/10.1063/1.3616144.

Barth, M., et al., "Spectral and angular redistribution of photoluminescence near a photonic stop band", Physical Review B, Aug. 23, 2005, pp. 1-10, vol. 72, Publisher: American Physical Society, Published in: DOI: 10.1103/PhysRevB.72.085129.

Bharadwaj, P., et al., "Spectral dependence of single molecule fluorescence enhancement", Optics Express, Oct. 12, 2007, pp. 14266-14274, vol. 15, No. 21, Publisher: Optical Society of America, Published in: https://www.osapublishing.org/oe/abstract.cfm?uri=oe-15-21-14266.

Block, I., et al., "A detection instrument for enhanced-fluorescence and label-free imaging on photonic crystal surfaces", Optics Express, Jul. 17, 2009, pp. 13222-13235, vol. 17, No. 15, Publisher: Optical Society of America, Published in: https://www.osapublishing.org/oe/abstract.cfm?uri=oe-17-15-13222&origin=search.

Boriskina, S., et al., "Optical gaps, mode patterns and dipole radiation in two-dimensional aperiodic photonic structures", Physica E, Aug. 22, 2008, pp. 1102-1106, vol. 41, Publisher: Elsevier, Published in: doi.org/10.1016/j.physe.2008.08.039.

Cao, S., et al., "Surface Plasmon-Coupled Emission: What Can Directional Fluorescence Bring to the Analytical Sciences?", Ann. Rev. Anal. Chem., Apr. 9, 2012, pp. 317-336, vol. 5, Publisher: Annual Reviews, Published in: doi: 10.1146/annurev-anchem-062011-143208.

Cesa, Y., et al., "Manipulation of the local density of photonic states to elucidate fluorescent protein emission rates", Physical Chemistry Chemical Physics, Feb. 11, 2009, pp. 2525-2531, vol. 11, Publisher: Owner Societies, Published in: DOI: 10.1039/b817902f.

Chatteirjee, R., et al., "Achieving Subdiffraction Imaging through Bound Surface States in Negative Refraction Photonic Crystals in the Near-Infrared Range," Physical Review Letters, May 9, 2008, pp. 1-4, vol. 100, No. 18, Publisher: American Physical Society, Published in: DOI: 10.1103/PhysRevLett.100.187401.

Choudhury, S., et al., "Tuning Fluorescence Direction with Plasmonic MetalDielectricMetal Substrates", J Phys Chem Lett, Sep. 4, 2013, pp. 227-232, vol. 4, No. 1, Publisher: NIH Public Access, Published in: doi:10.1021/z301867b.

Chowdhury, M., et al., "Imaging three-dimensional light propagation through periodic nanohole arrays using scanning aperture microscopy", Appl Phys Lett, Mar. 1, 2007, pp. 1-7, vol. 91, No. 10, Publisher: NIH Public Access, Published in: doi:10.1063/1.2783177.

Deng, W., et al., "Enhanced Flow Cytometry-Based Bead Immunoassays Using Metal Nanostructures", Analytical Chemistry, Aug. 4, 2009, pp. 7248-7255, vol. 81, No. 17, Publisher: American Chemical Society, Published in: doi: 10.1021/ac900947h.

Deng, W., et al., "Plasmonic Approach to Enhanced Fluorescence for Applications in Biotechnology and the Life Sciences", Langmuir, May 8, 2012, pp. 10152-10163, vol. 28, Publisher: American Chemical Society, Published in: dx.doi.org/10.1021/la300332x.

Descrovi, E., et al., "Near-field imaging of Bloch surface waves on silicon nitride one-dimensional photonic crystals", Optics Express, Apr. 3, 2008, pp. 5453-5464, vol. 16, No. 8, Publisher: Optical

(56) References Cited

OTHER PUBLICATIONS

Society, Published in: https://www.osapublishing.org/oe/abstract.cfm?uri=oe-16-8-5453&origin=search.

Descrovi, E., et al., "Guided Bloch Surface Waves on Ultrathin Polymeric Ridges", Nano Letters, May 6, 2010, pp. 2087-2091, vol. 10, Publisher: American Chemical Society, Published in: DOI: 10.1021/nl100481q.

Ding, Y., et al., "Resonant leaky-mode spectral-band engineering and device applications", Optics Express, Nov. 15, 2004, pp. 5661-5674, vol. 12, No. 23, Publisher: Optical Society, Published in: doi: 10.1364/OPEX.12.005661.

Engelen, R.J.P., et al., "Subwavelength Structure of the Evanescent Field of an Optical Bloch Wave", Physical Review Letters, Jan. 19, 2009, pp. 1-5, vol. 102, No. 2, Publisher: American Physical Society, Published in: http://dx.doi.org/10.1103/PhysRevLett.102.023902.

Estrada, L.C., et al., "Small volume excitation and enhancement of dye fluorescence on a 2D photonic crystal surface", Optics Express, Feb. 5, 2010, pp. 3693-3699, vol. 18, No. 4, Publisher: Optical Society, Published in: doi: 10.1364/OE.18.003693.

Farmer, A., et al., "Biosensing using surface electromagnetic waves in photonic band gap multilayers", Sensors and Actuators B, Jun. 16, 2012, pp. 79-84, vol. 173, Publisher: Elsevier, Published in: file:///C|/Users/Dorothy%20Altmiller/AppData/Local/Temp/Temp2_JL-2013-117%20(US)%20IDS%20References.zip/dx.doi.org/10.1016/j.snb.2012.06.015.

Feng, X., et al., "Spontaneous Emission Rate Enhancement of Silicon Nanocrystals by Plasmonic Bandgap on Copper Grating", Journal of Lightwave Technology, May 1, 2010, pp. 1420-1430, vol. 28, No. 9, Publisher: IEEE, Published in: doi: 10.1109/JLT.2010.2042788.

Frascella, F., et al., "A Fluorescent One-Dimensional Photonic Crystal for Label-Free Biosensing Based on Bloch Surface Waves", Sensors, Feb. 5, 2013, pp. 2011-2022, vol. 13, Publisher: MDPI, Published in: doi:10.3390/s130202011.

Frezza, L., et al., "Directional Enhancement of Spontaneous Emission in Polymer Flexible Microcavities", Journal of Physical Chemistry, Aug. 31, 2011, pp. 19939-19946, vol. 115, Publisher: American Chemical Society, Published in: dx.doi.org/10.1021/jp206105r.

Fu, Y., et al., "Large enhancement of single molecule fluorescence by coupling to hollow silver nanoshells", Chem Commun (Camb.), Oct. 9, 2012, pp. 9726-9728, vol. 48, No. 78, Publisher: Royal Society of Chemistry, Published in: doi:10.1039/c2cc34025a.

Ganesh, N., et al., "Enhanced fluorescence emission from quantum dots on a photonic crystal surface", Nature Nanotechnology, Jul. 29, 2007, pp. 515-520, vol. 2, Publisher: Nature, Published in: http://www.nature.com/doifinder/10.1038/nnano.2007.216.

Ganesh, N., et al., "Leaky-mode assisted fluorescence extraction: application to fluorescence enhancement biosensors", Optics Express, Dec. 15, 2008, pp. 21626-21640, vol. 16, No. 26, Publisher: Optical Society, Published in: doi: 10.1364/OE.16.021626.

Gao, J., et al., "Experimental confirmation of strong fluorescence enhancement using one-dimensional GaP/SiO2 photonic band gap structure", Optical Materials Express, Oct. 12, 2011, pp. 1216-1223, vol. 1, No. 7, Publisher: Optical Society, Published in: doi: 10.1364/OME.1.001216.

Gao, J., et al., "Polarization multiplexed fluorescence enhancer using a pixelated one-dimensional photonic band gap structure", Optics Letters, Jun. 25, 2012, pp. 2640-2642, vol. 37, No. 13, Publisher: Optical Society, Published in: doi: 10.1364/OL.37.002640.

Giorgis, F., et al., "Experimental determination of the sensitivity of Bloch Surface Waves based sensors", Optics Express, Apr. 12, 2010, pp. 1-7, vol. 18, No. 8, Publisher: Optical Society, Published in: https://www.osapublishing.org/oe/abstract.cfm?uri=oe-18-8-8087.

Gryczynski, I., et al., "Effects of Sample Thickness on the Optical Properties of Surface Plasmon-Coupled Emission", J. Phys. Chem. B, Jul. 16, 2004, pp. 12073-12083, vol. 108, Publisher: American Chemical Society, Published in: doi:10.1021/jp0312619.

Gryczynski, I., et al, "Radiative decay engineering 4. Experimental studies of surface plasmon-coupled directional emission", Anal. Biochem., Jan. 15, 2004, pp. 170-182, vol. 324, No. 2, Publisher: NIH Public Access, Published in: doi:10.1016/j.ab.2003.09.036.

Guillermain, E., et al., "Bragg surface wave device based on porous silicon and its application for sensing", Applied Physics Letters, Jun. 15, 2007, pp. 1-3, vol. 90, No. 24116, Publisher: American Institute of Physics, Published in: http://dx.doi.org/10.1063/1.2747671.

Guo, Y., et al., "Sensitive molecular binding assay using a photonic crystal structure in total internal reflection", Optics Express, Jul. 22, 2008, pp. 11741-11749, vol. 16, No. 16, Publisher: Optical Society, Published in: https://www.osapublishing.org/oe/abstract.cfm?uri=oe-16-16-11741.

Holtz, J., et al., "Polymerized colloidal crystal hydrogel films as intelligent chemical sensing materials", Nature, Oct. 23, 1997, pp. 829-832, vol. 389, Publisher: Macmillan Publishers Ltd., Published in: http://www.nature.com/nature/journal/v389/n6653/abs/389829a0.html.

Huang, C., et al., "Application of Photonic Crystal Enhanced Fluorescence to Cancer Biomarker Microarrays", Anal. Chem., Jan. 21, 2011, pp. 1425-1430, vol. 83, Publisher: ACS Publications, Published in: dx.doi.org/10.1021/ac102989n.

Inoue, A., et al., "One dimensional polymeric photonic crystal doped with second-order nonlinear optical chromophore", Organic Photonic Materials and Devices XI, Feb. 17, 2009, pp. 1-8, vol. 7213, No. 1C, Publisher: SPIE, Published in: doi: 10.1117/12.809268.

Inouye, H., et al., "Optical Properties of a Total-Reflection-Type One-Dimensional Photonic Crystal", Journal of Quantum Electronics, Jul. 1, 2002, pp. 867-871, vol. 38, No. 7, Publisher: IEEE, Published in: doi:10.1109/JQE.2002.1017599.

John, S., "Strong Localization of Photons in Certain Dsordered Dielectric Superlattices", Physical Review Letters, Jun. 8, 1987, pp. 2486-2489, vol. 58, No. 23, Publisher: American Physical Society, Published in: DOI:http://dx.doi.org/10.1103/PhysRevLett.58.2486.

Kaniber, M., et al., "Highly efficient single-photon emission from single quantum dots within a two-dimensional photonic band-gap", Physical Review B, Feb. 28, 2008, pp. 1-4, vol. 77, No. 073312, Publisher: American Physical Society, Published in: DOI: 10.1103/PhysRevB.77.073312.

Kelly, C., et al., "An Array of Planar Apertures for Near-Field Fluorescence Correlation Spectroscopy", Biophysical Journal, Apr. 1, 2011, pp. L34-L36, vol. 100, Publisher: Biophysical Society, Published in: doi: 10.1016/j.bpj.2011.02.034.

Kinkhabwala, A., et al., "Large single-molecule fluorescence enhancements produced by a bowtie nanoantenna", Nature Photonics, Oct. 18, 2009, pp. 654-657, vol. 3, Publisher: Nature, Published in: doi: 10.1038/nphoton.2009.187.

Knoben, W., et al., "Metal-induced fluorescence enhancement as a new detection mechanism for vapor sensing", Sensors and Actuators B, May 4, 2010, pp. 307-314, vol. 148, Publisher Elsevier BV, Published in: doi.org/10.1016/j.snb.2010.04.044.

Koenderink, A., et al., "Spontaneous emission in the near-field of 2D photonic crystals", Optics Letters, May 15, 2005, pp. 3210-3212, vol. 30, Publisher: Optics Society, Published in: doi:10.1364/OL.30.003210.

Kubo, S., et al., "Anisotropic Accelerated Emission of the Chromophores in Photonic Crystals Consisting of a Polystyrene Opal Structure", J. Phys. Chem. C, Jun. 4, 2009, pp. 11704-11711, vol. 113, Publisher: American chemical Society, Published in: doi: 10.1021/jp901743r.

Kurt, P., et al, "Structural color via layer-by-layer deposition: layered nanoparticle arrays with near-UV and visible reflectivity bands", Journal of Materials Chemistry, Oct. 15, 2009, pp. 8920-8927, vol. 19, Publisher: Royal Society of Chemistry, Published in: DOI: 10.1039/b912211g.

Lai, C., et al., "Highly-directional emission patterns based on near single guided mode extraction from GaN-based ultrathin microcavity light-emitting diodes with photonic crystals", Applied Physics Letters, Jul. 9, 2010, pp. 1-3, vol. 97, No. 013108, Publisher: American Institute of Physics, Published in: doi:10.1063/1.3459970.

(56) References Cited

OTHER PUBLICATIONS

Lakowicz, J., "Radiative Decay Engineering: Biophysical and Biomedical Applications", Analytical Biochemistry, Oct. 5, 2001, pp. 1-24, vol. 298, Publisher: Academic Press, Published in: doi:10.1006/abio.2001.5377.

\* cited by examiner

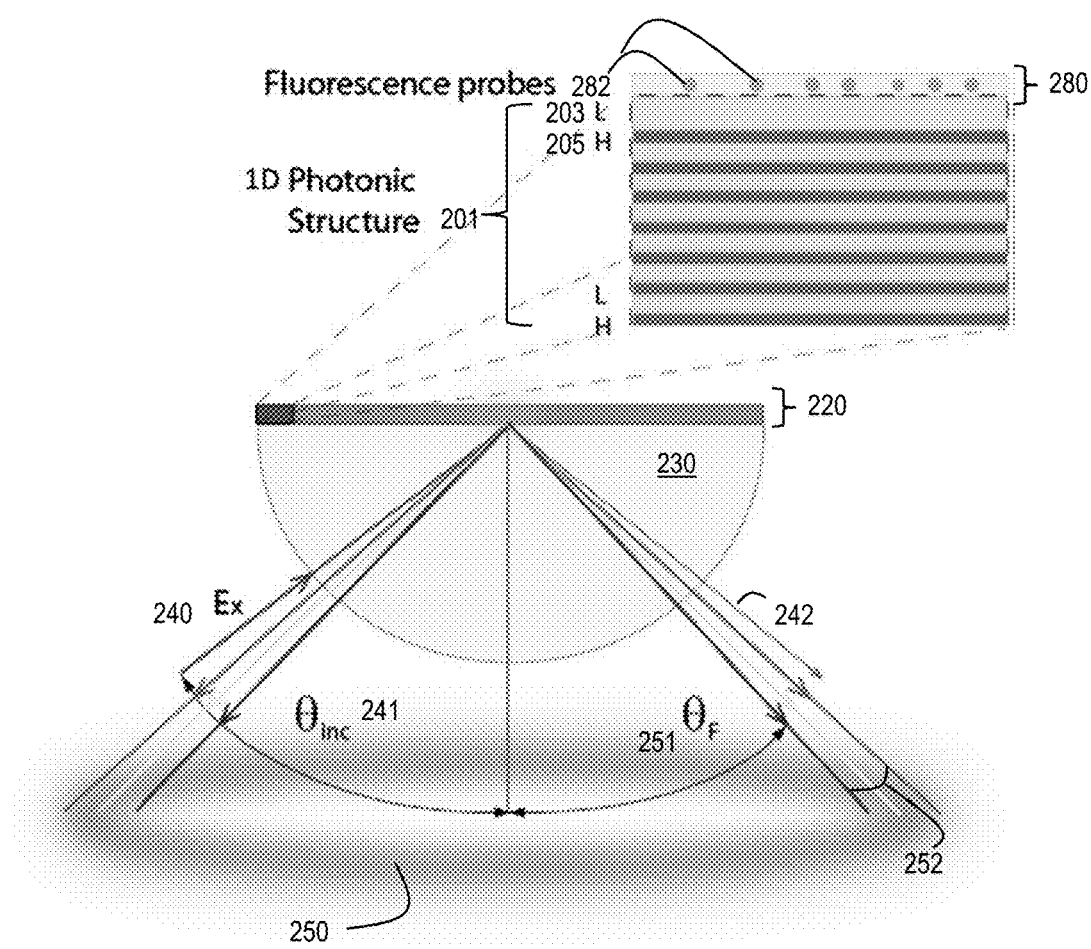

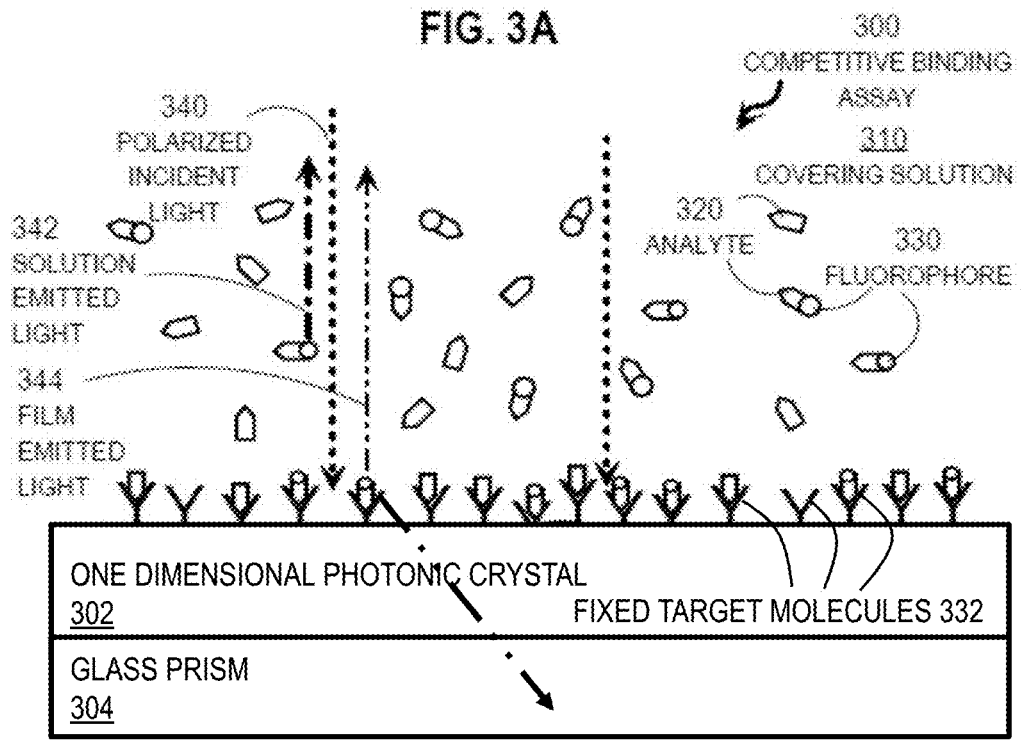
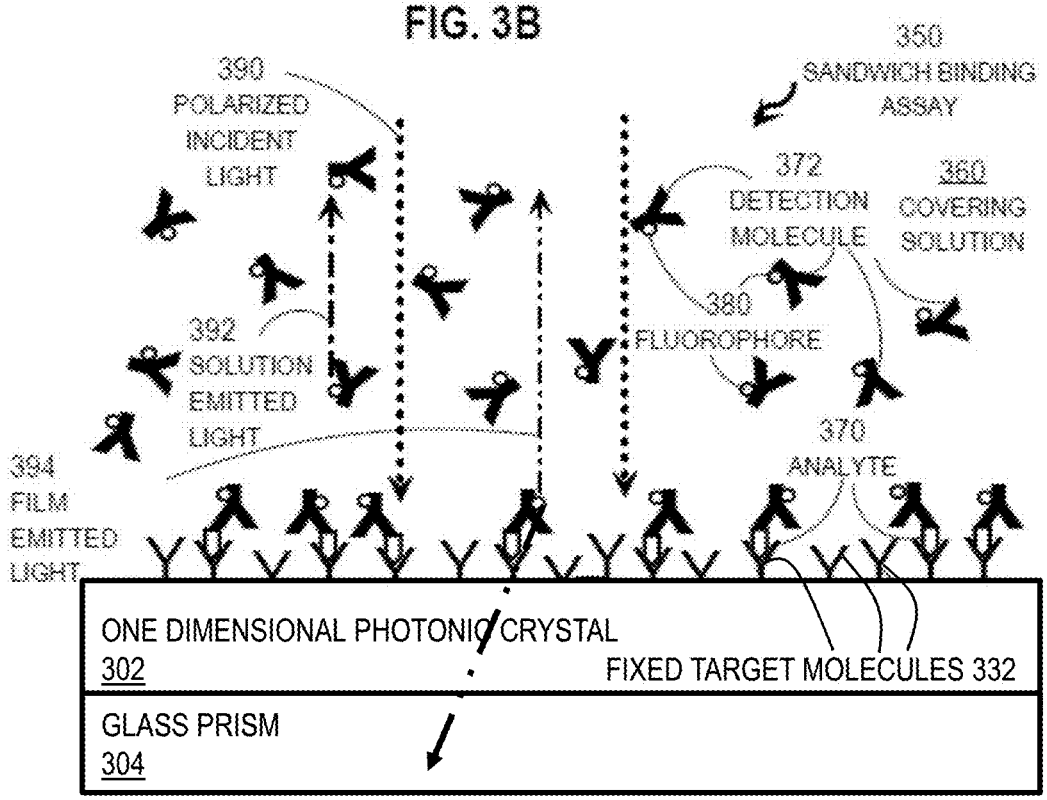

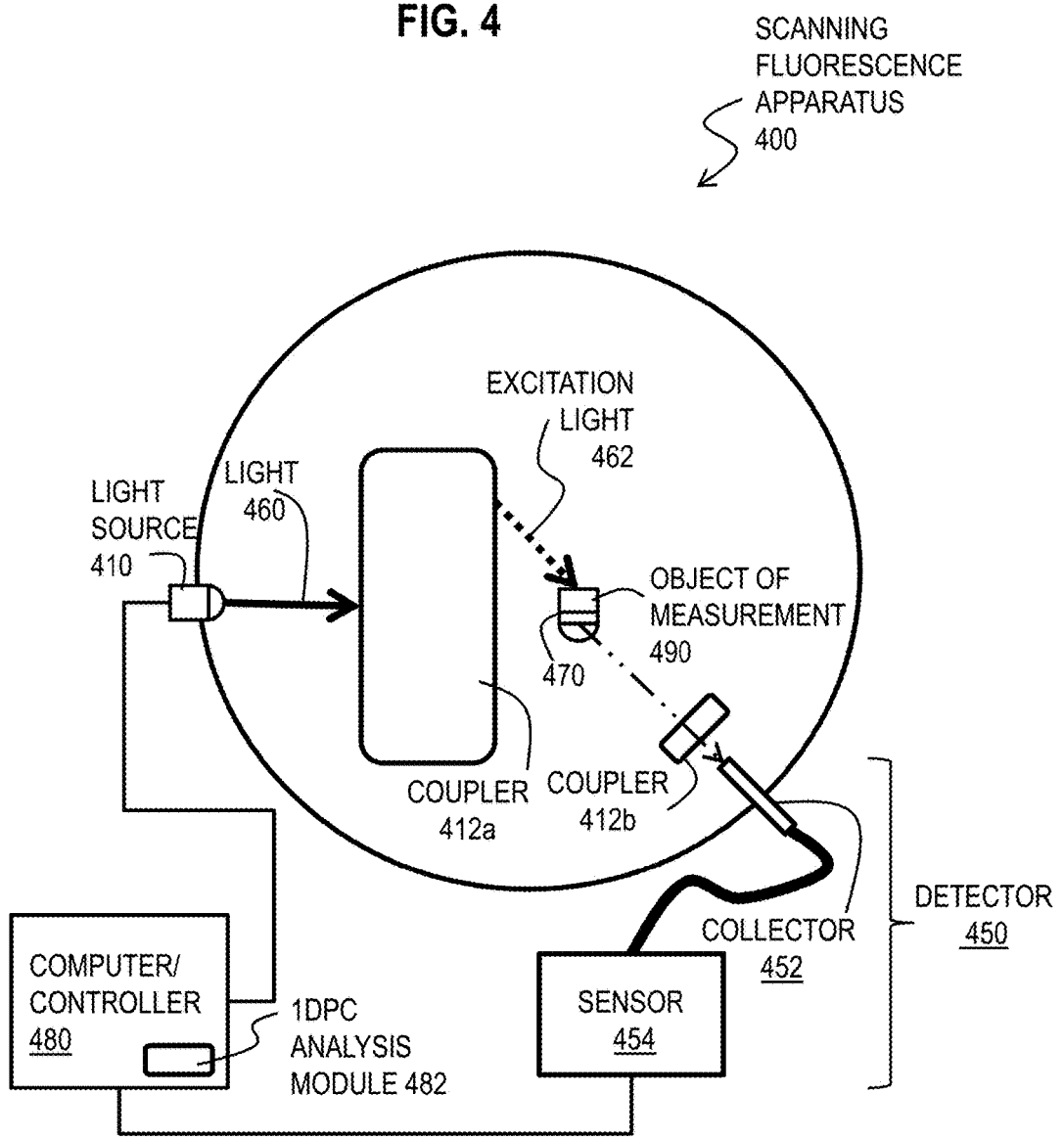

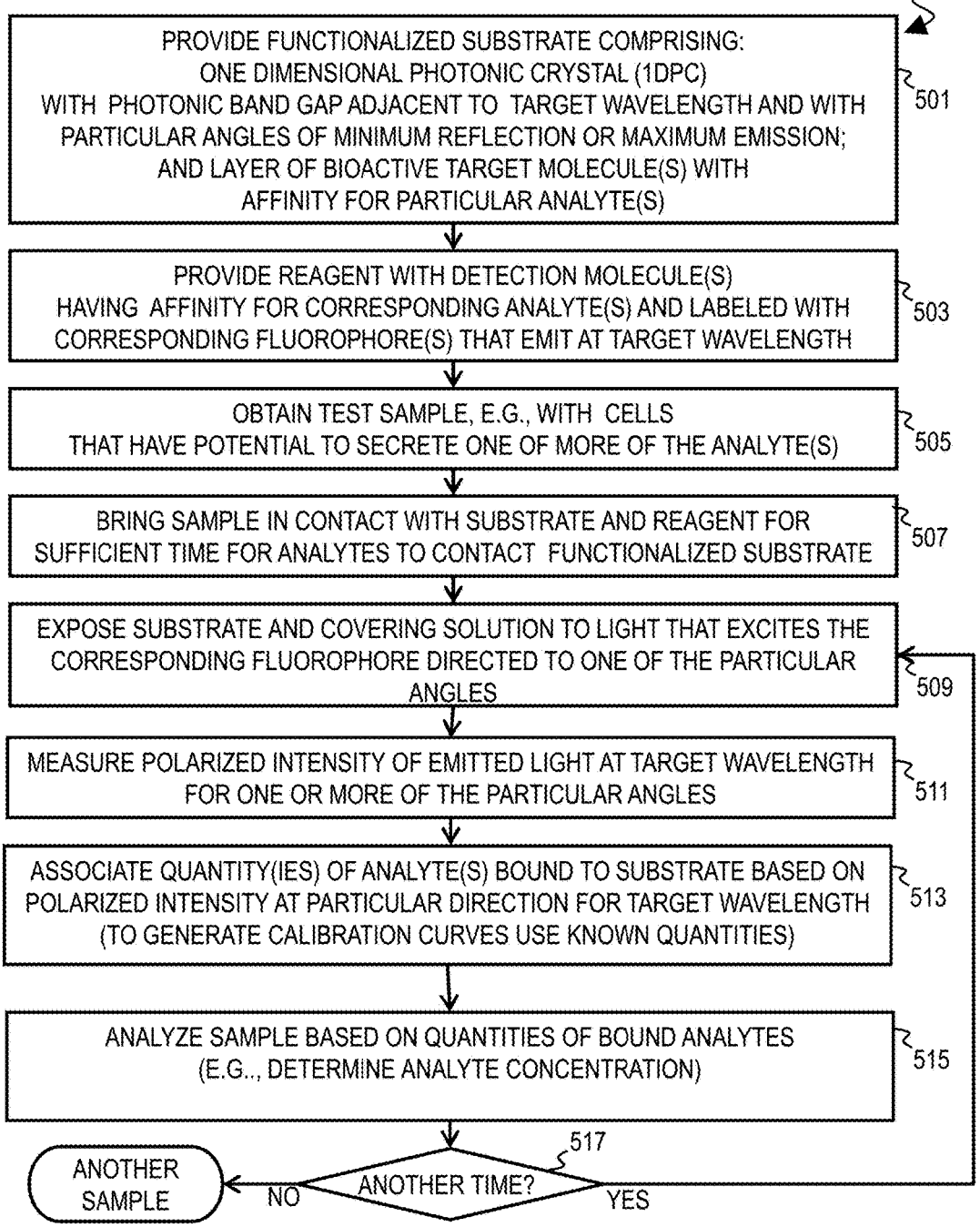

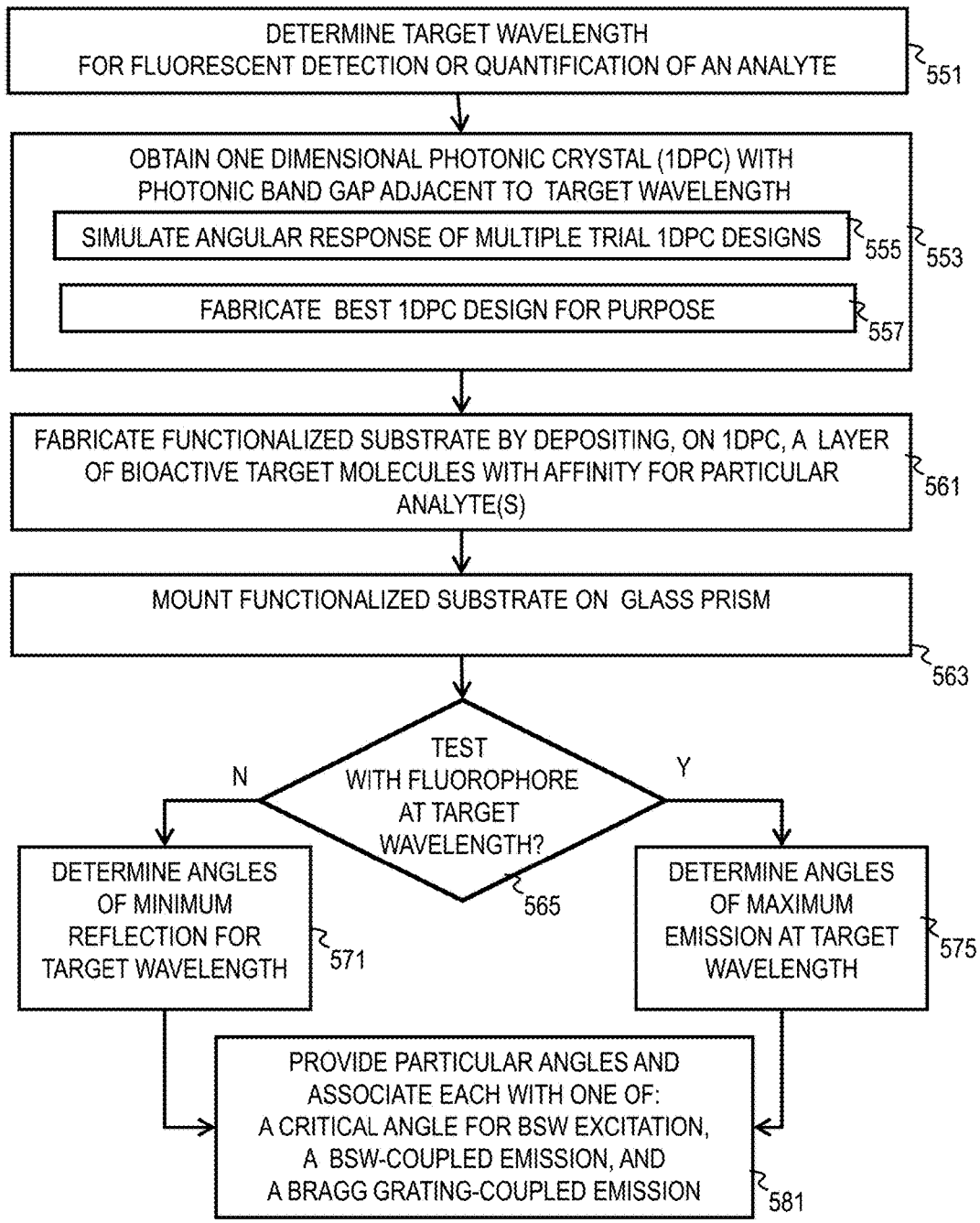

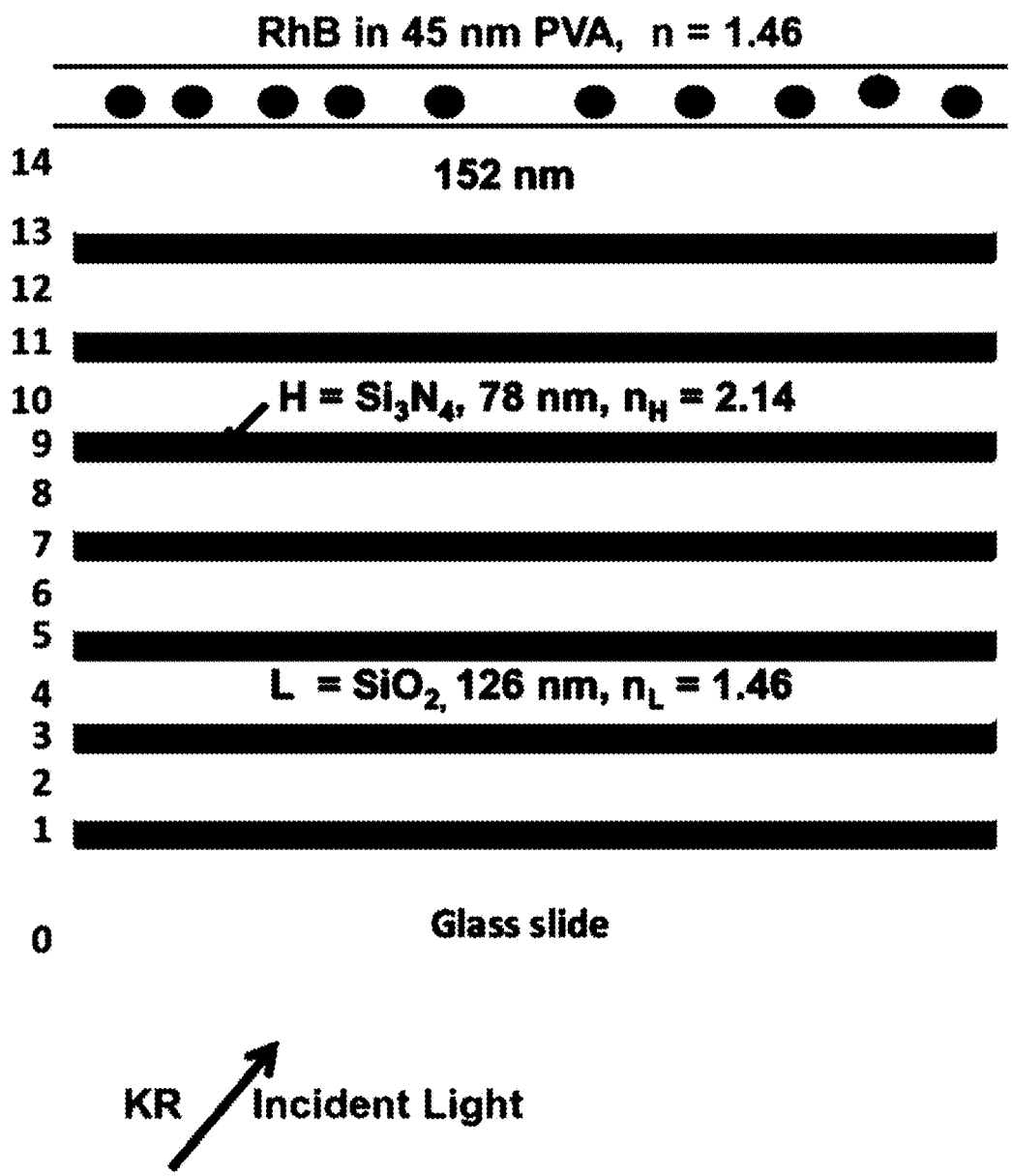

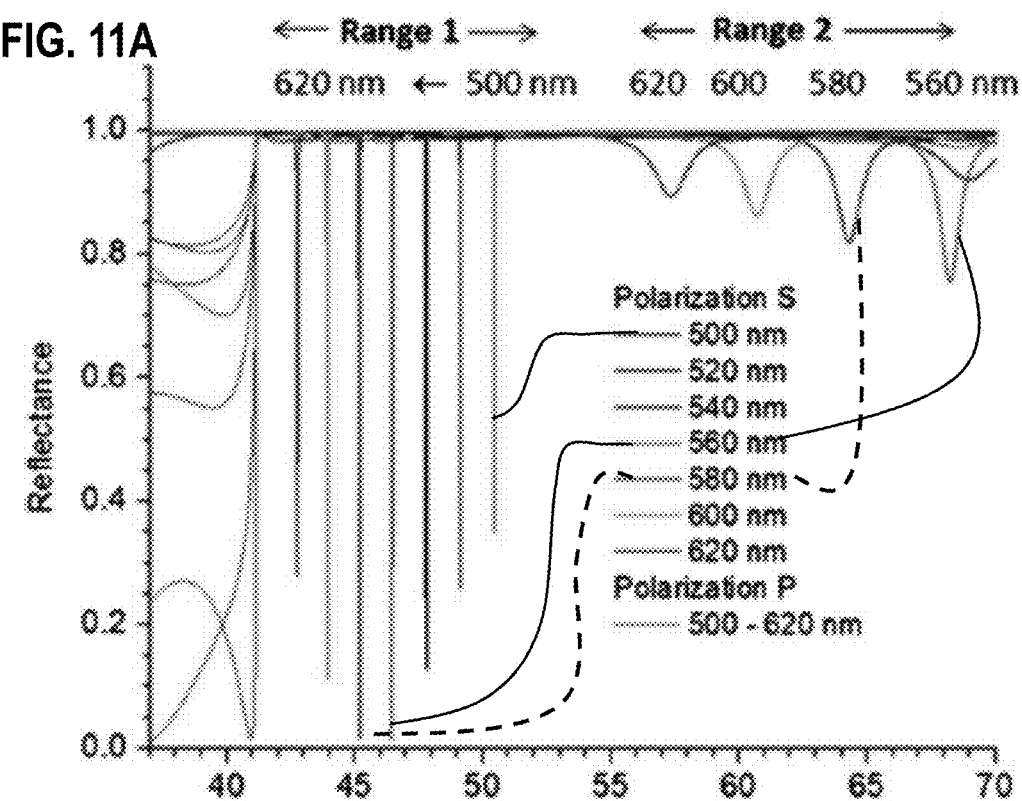
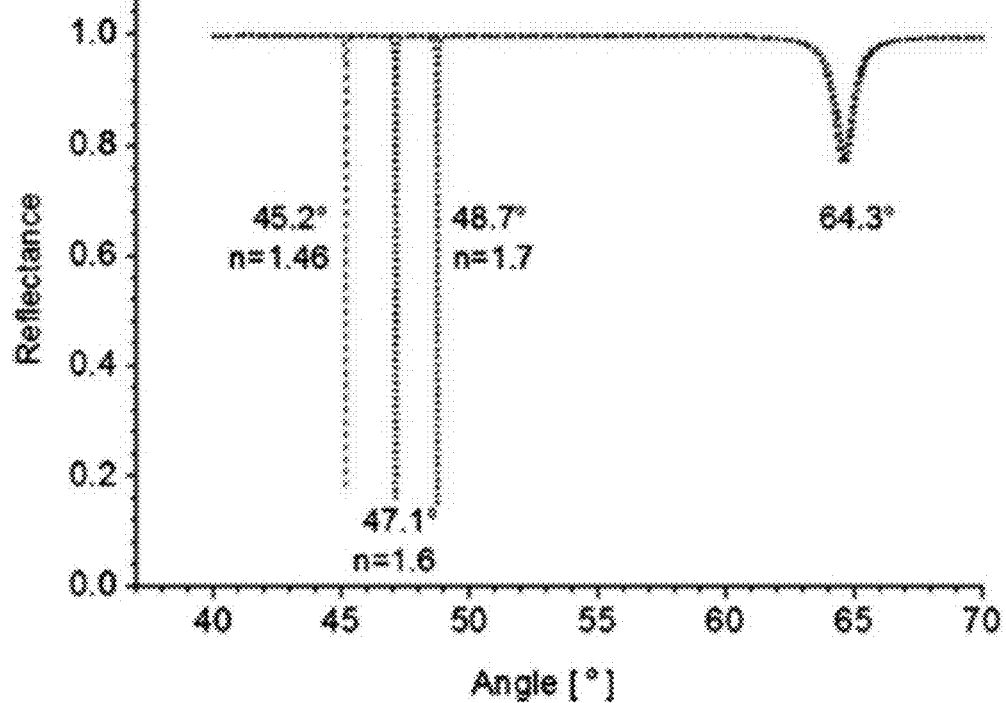

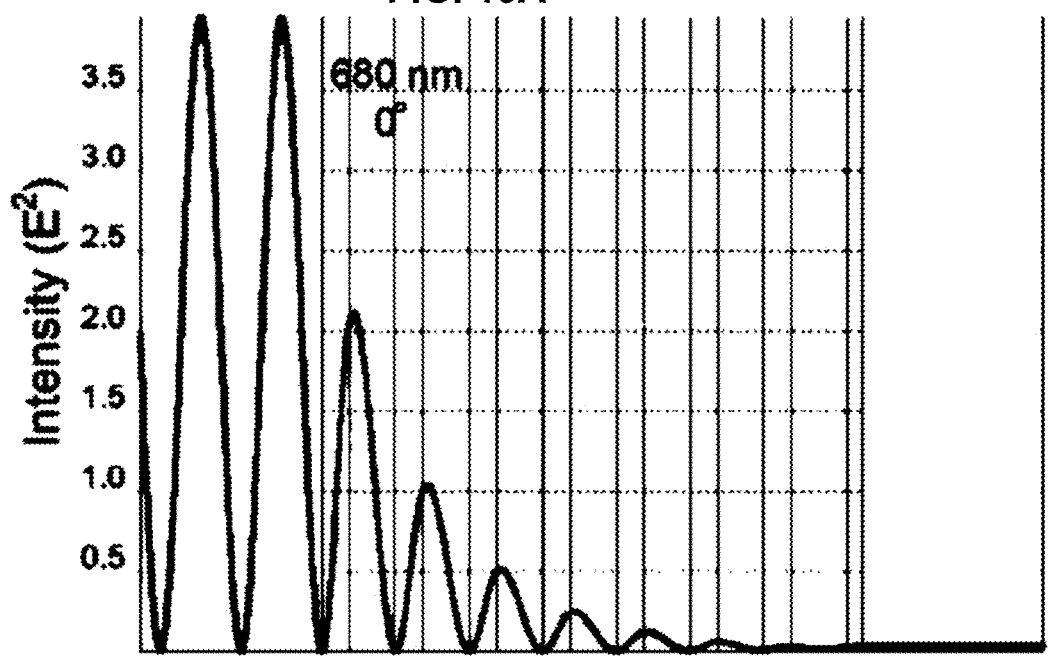
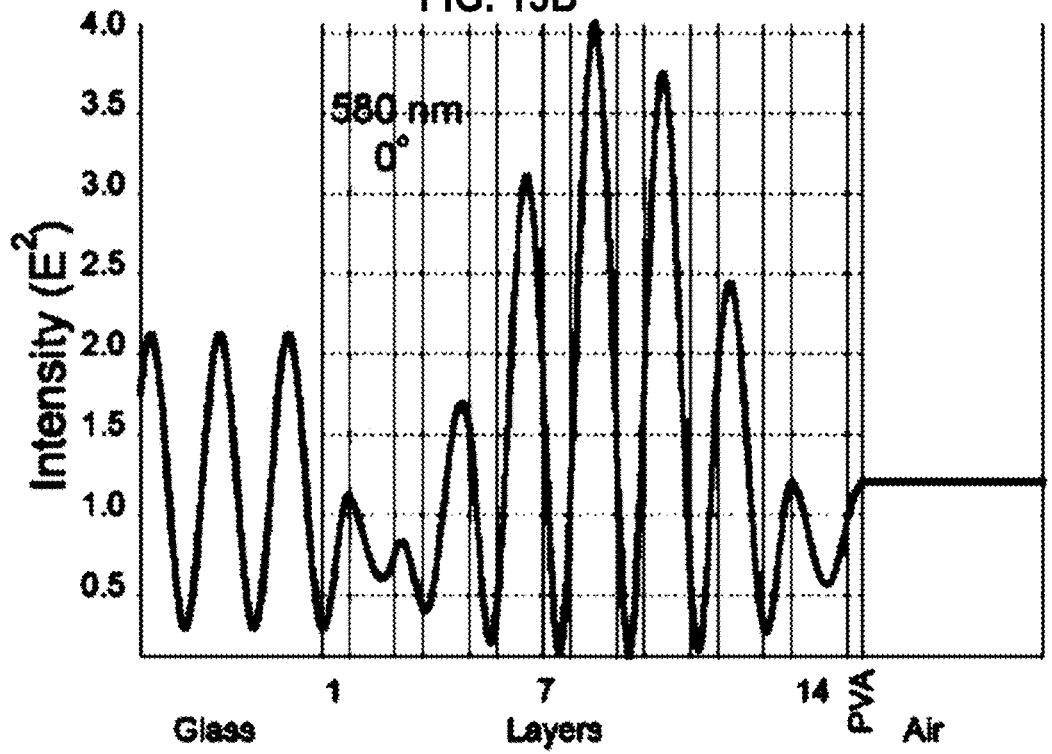

ONE DIMENSIONAL PHOTONIC CRYSTALS FOR ENHANCED FLUORESCENCE BASED SENSING, IMAGING AND ASSAYS

CROSS-REFERENCE TO RELATED APPLICATIONS

This application claims benefit of Provisional Appln. 62/001,653, filed May 22, 2014, the entire contents of which are hereby incorporated by reference as if fully set forth herein, under 35 U.S.C. § 119.

STATEMENT OF GOVERNMENTAL INTEREST

This invention was made with government support under Grant Numbers HG002655, EB006521, and HG005090 awarded by the National Institutes of Health. The government has certain rights in the invention.

BACKGROUND

In affinity assays, a known quantity of a labeled probe competes with or binds to an unknown quantity of unlabeled analyte at binding sites on a target molecule for which the analyte has an affinity. The labeled probe that is bound to the target molecule presents a different measurable phenomenon than the labeled probe that is unbound. Calibration curves relate the presence or quantity of the analyte to the relative amount of bound to unbound labeled probe. The calibration curves are generated by measuring the relative amounts of bound and unbound labeled probe in the presence of known quantities of analyte. In sandwich binding assays, the probe binds to the analyte that is bound to the target molecule. In immunoassays, the analyte is an antigen and the target molecule is an antibody.

In some approaches, the target molecule is affixed to a substrate with properties that causes the emissions from the label to be distinguishable from emissions from a label that is not bound to the target so that the label is displaced farther from the substrate.

During the past decade, there has been a growing interest in plasmonics and in the near-field interactions of fluorophores with metallic structures. Metallic surfaces and particles display surface plasmons, which can result in enhanced and selective excitation of nearby fluorophores. A plasmon is an oscillation of free electron density in a metal particle which can form waves on metal surfaces with the same electric fields and frequencies but shorter wavelengths than electromagnetic waves. In addition, these nearby excited state fluorophores can interact with the photonic mode density (PMD) created by the plasmons, which increases the emission rates and decreases the lifetimes. The PMD is also referred to as the density of states (DoS). The spatial distribution of light from the fluorophore can be changed from the usual omnidirectional distribution to a more narrow spatial distribution, which is determined by wave vector matching at the metallic surfaces.

The use of metals with fluorescence does have some disadvantages. For metal-enhanced fluorescence (MEF), the metal must display a plasmon resonance at wavelengths where its intrinsic absorption is low. This limits the practical metals to Ag, Au, and Al, with a few other metals in occasional use for MEF. There is an optimal distance for metal enhancement near 10 nm from the metal surface because fluorophores at closer distances are often quenched. Metals are lossy and quickly dissipate the optical energy. As a result, MEF often occurs with an increased excitation—relaxation cycling rate.

SUMMARY

It has been determined that improved techniques are desirable for measuring fluorescent emission in biological detection, imaging and assays. Techniques are provided for using a one dimensional photonic crystal (1DPC) as a substrate for enhanced fluorescence based sensing, imaging and assays that alleviate one or more deficiencies of prior art approaches. Each of the layers may be amorphous, but the term "photonic crystals" is widely used. As used in this context and hereinafter, the term "crystal" refers to periodicity on the wavelength scale, and not necessarily on the atomic scale.

In a first set of embodiments, a system includes a source of incident light, a functionalized substrate, an optical coupler and a detector. The functionalized substrate is configured to be placed in contact with a mixture of a sample and a reagent. The functionalized substrate comprises a one dimensional photonic crystal for a target optical frequency and a bioactive target molecule that has an affinity for a particular analyte. The one dimensional photonic crystal includes multiple dielectric layers including multiple high index of refraction layers alternating with multiple low index of refraction layers. The thickness of each layer is within a factor of four of a wavelength of the target optical frequency in the layer. The reagent includes a detection molecule for the particular analyte (the detection molecule includes a fluorophore that emits at the target optical frequency and binds to the analyte or the target molecule or both). The optical coupler is configured to direct incident light onto the functionalized substrate; and the detector is configured to measure fluorescent emissions from the functionalized substrate.

In some embodiments of the first set, the target optical frequency is within a peak in a local radiative density of states (LRDoS) adjacent to a photonic band gap of the one dimensional photonic crystal.

In some embodiments of the first set, the detector is configured for collecting fluorescent emissions in a collection cone that includes an angle of an emission intensity maximum that is independent of a direction of the incident light impinging on the substrate. In various of these embodiments, the emission intensity maximum is associated with a Bloch surface wave coupled emission (BWCE) or a Bragg grating coupled emission (BGCE) or both.

In some embodiments of the first set, the functionalized substrate further comprising a glass prism abutting a surface of the one dimensional photonic crystal opposite a functionalized surface with the bioactive target molecule. In some of these embodiments, the optical coupler is configured to direct the incident light to impinge on a surface of the one dimensional photonic crystal through the glass prism and at an angle of minimum external reflection. In some of these embodiments, the optical coupler further comprises a polarizer configured to polarize the incident light in a direction parallel to the plurality of dielectric layers.

In a second set of embodiments, a method uses the system to obtain measurements of at least one of intensity or direction or polarization of fluorescent emissions at the functionalized substrate in contact with the sample and reagent in response to the incident light. The method also determines a concentration of the particular analyte in the sample from a calibration curve and the measurement. In some embodiments, the method also determines the calibration curve that relates concentration of the particular analyte to at least one of intensity or direction or polarization of fluorescent emissions at the functionalized substrate in response to incident light for a plurality of known concentrations of the particular analyte mixed with the reagent.

In a third set of embodiments, an article of manufacture is a functionalized substrate for a target optical frequency comprising the one dimensional photonic crystal that is functionalized with a bioactive target molecule that has an affinity for a particular analyte.

In a fourth set of embodiments, an article of manufacture is a fluorescence affinity assay kit that includes the one dimensional photonic crystal and a solution comprising a bioactive target molecule that has affinity for a particular analyte, wherein the target molecule includes a ligand for affixing to the one dimensional photonic crystal. The kit also includes a reagent comprising at least one type of detection molecule, wherein the detection molecule comprises a fluorophore, and the detection molecule has affinity for the particular analyte.

In other sets of embodiments, an apparatus or a non-transitory computer-readable medium is configured to perform one or more steps of the above method.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings, in which like reference numerals refer to similar elements, and in which:

FIG. 2A is a block diagram that illustrates an example emission cone from fluorophores on a 1DPC when excited by incident light from below, according to various embodiments;

FIG. 3A is a block diagram that illustrates an example enhanced competitive binding assay during operation, according to an embodiment;

FIG. 3B is a block diagram that illustrates an example enhanced sandwich binding assay during operation, according to an embodiment;

FIG. 4 is a block diagram that illustrates an example enhanced fluorescence measurement system using a 1DPC, according to an embodiment;

FIG. 5A and FIG. 5B are flow charts that illustrate an example method to perform an enhanced fluorescence assay using a 1DPC, according to an embodiment;

FIG. 7 is a block diagram that illustrates an example 1DPC, according to an embodiment;

FIG. 11A and FIG. 11B are graphs that illustrate an example simulated frequency separation by angle in reflectance from a 1DPC model tuned to observations, according to an embodiment;

FIG. 13A and FIG. 13B are graphs that illustrate example simulated illumination-induced electric field intensity inside the 1DPCs at optical frequencies inside and adjacent to the photonic band gap, respectively, according to an embodiment;

DETAILED DESCRIPTION

Figure 1A:
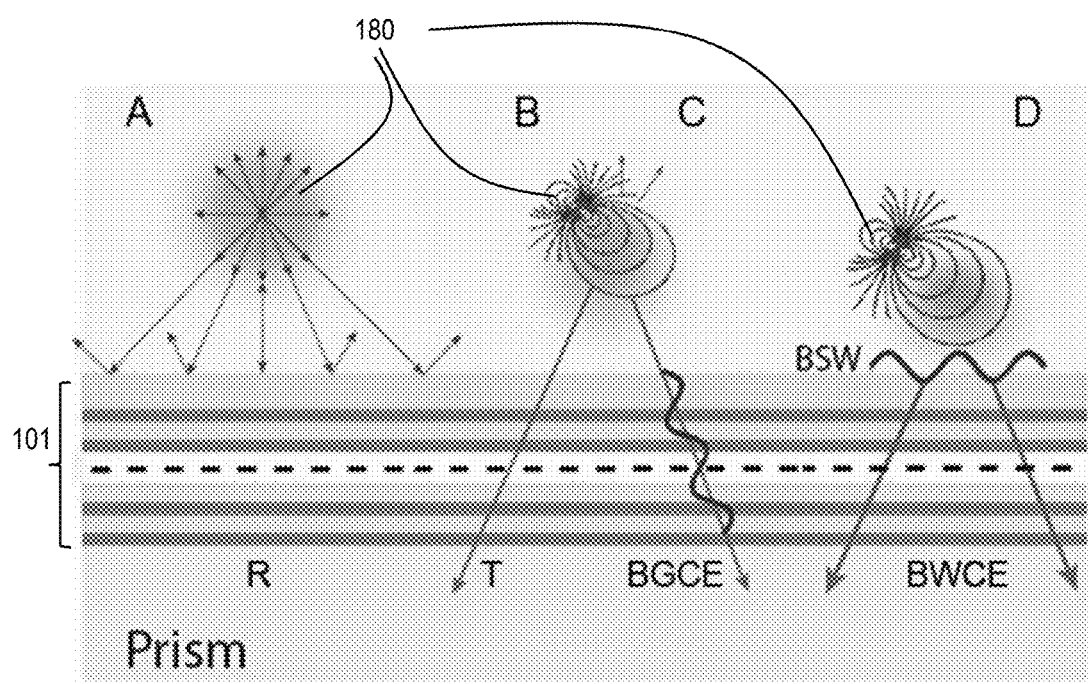
FIG. 1A is a block diagram that illustrates example interactions of a fluorophore with a one dimensional photonic crystal (1DPC), according to various embodiments.

Techniques are described for enhanced fluorescence based sensing, imaging and assays using one dimensional photonic crystals. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of four, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of fluorescent assays in the presence of a particular 1DPC. However, the invention is not limited to this context. In other embodiments, the 1DCP is used in a substrate for simple detection of one or more analytes or for intensity imaging multiple analytes simultaneously on different portions of the substrate, and any 1DPC may be used in the substrate. Furthermore, any fluorophore may be used to label a detection molecule used to determine binding of analyte to target molecule. Indeed, any species that emits light can be used in various embodiments, including organic fluorophores, inorganic fluorophores such as lanthanide, quantum dots, carbon dots, diamond nanoparticles, emission from metallic structures and metal clusters.

Furthermore, as described herein, the use of 1DPC implies different index of refraction (n) in different layers. While the optical frequency is constant in each layer, the speed and hence the wavelength is inversely proportional to the index of refraction. Because the optical spectrum is usually described in terms of the optical wavelength in a vacuum (n=1), which is about the same as the wavelength in air (n=1.000293 at a wavelength of 589.29 nanometers), the term "wavelength" is used for convenience to mean the wavelength in air, unless otherwise stated explicitly (such as "the wavelength in a layer of the 1DPC"). Thus the wavelength of incident light is the wavelength in air of the optical frequency of the incident light, which wavelength changes as the incident light penetrates the 1DPC or other material, such as the sample or glass; and, the wavelength of a fluorescent emission is the wavelength in air of the optical frequency of the emission, which wavelength also changes as the emission penetrates the 1DPC or other material.

1. Definitions

As used in this description, the following terms have the meanings given here.

| | |
|---|---|
| amino acids | An organic molecule comprising both carboxyl and amino groups that can form peptide bonds with complementary groups on other amino acids. 22 amino acids comprise all the proteins found in most living organisms. |
| analyte | a component of a sample for which a quantity is to be determined, including but not limited to a polymer, a ligand, an antigen, an antibody, a protein, a peptide, DNA, RNA, oligonucleotide, a virus or a bacterium. |
| assay | a method to determine the quantity (e.g., the presence, absence, or concentration) of one or more components called analytes in a test sample. |
| assay kit | a collection of materials to be used in an assay. |
| concentration | a fraction of a sample by weight or volume which is due to a component of the sample. |
| detection molecule | a molecule labeled with a fluorophore that is used to detect binding of an analyte to a target molecule by binding to the analyte or by competing with the analyte for binding sites on the target molecule. Also called a probe-fluorophore conjugate or probe-dye conjugate. |
| fluorophore | a functional group in a molecule which absorbs electromagnetic waves at a specific wavelength and subsequently emits electromagnetic waves at a different specific wavelength. Fluorophores include, but are not limited to, fluoresceins, eosin, coumarines, rhodamines, cyanines, benzophenoxazines, phycobiliproteins or fluorescent proteins. |
| functionalized substrate | a substrate that is conditioned to perform a particular function by deposition of layers of one or more types of molecules, such as a glass slide coated with bioactive molecules that facilitate fixing of an analyte to the substrate. |
| ligand | a functional group in a molecule which binds to a metal, generally involving formal donation of one or more of its electrons. Metal-ligand bindings range from covalent bonds to electrostatic attraction between ions (ionic bonding). |
| light | electromagnetic (em) waves in a visible portion of the electromagnetic spectrum, which includes wavelengths in air from about 300 to about 800 nanometers (nm, 1 nm = $10^{-9}$ meters). |
| nanoparticles | particles each having a dimension in a size range from about 1 to about 1000 nanometers, nm. 1 nm = $10^{-9}$ meters. |
| plasmon | an oscillation of free electron density in a metal particle which can form waves on metal surfaces with the same electric fields and frequencies but shorter wavelengths than incident electromagnetic waves. Metal surface plasmons with frequencies in the visible |

| | |
|---|---|
| | spectrum can interact with light. |
| Plasmonic substrate | A substrate that includes a layer of metal nanoparticles that form plasmons with frequencies in a spectral band of one or more fluorophores |
| probe | a molecule that is used to detect binding of an analyte to a target molecule by binding to the analyte or by competing with the analyte for binding sites on the target molecule (the portion of a detection molecule excluding the fluorophore). Probes include, but are not limited to, a polymer, a ligand, an antigen, an antibody, a protein, an oligomer, a protein, a peptide, DNA, RNA or an oligonucleotide. |
| probe-fluorophore conjugate | A detection molecule. |
| protein | A large molecule made up of a long chain of amino acids. Shorter chains of amino acids are called peptides or protein fragments. |
| reagent | substance or compound consumed during a chemical reaction. |
| RhB | Rhodamine B, a chemical compound and a dye. Rhodamine dyes are used extensively in biotechnology applications such as fluorescence microscopy, flow cytometry, fluorescence correlation spectroscopy and ELISA. Rhodamine B is tunable around 610 nm when used as a laser dye. Its luminescence quantum yield is 0.65 in basic ethanol, 0.49 in ethanol, and 0.68 in 94% ethanol. The fluorescence yield is temperature dependent. A solution of 3 grams per liter of ethylene glycol absorbs virtually all incident light from 220 nm to 600 nm and emits with a peak at about 630 nm. |
| solution | a liquid mixture. |
| substrate | a material on which a process is conducted |
| target molecule | a molecule which has an affinity for a particular analyte. Target molecules include, but are not limited to, a polymer, a ligand, an antigen, an antibody, a protein, a peptide, DNA, RNA, an oligonucleotide. Also called a capture molecule. |
| test sample | a sample, such as a biological sample, with an unknown quantity of an analyte |

2. Overview

Advantages have been discovered in the use of near-field interactions of dielectric photonic crystals (PCs) with fluorophores. PCs are defined according to their dimensionality. One-dimensional (1D) PCs are made up of multiple layers of dielectrics with different refractive indexes. Well-known examples include Bragg gratings (BGs) or notch filters for optical spectroscopy. PCs have unusual optical properties because they can display photonic band gaps (PBGs), which are optical frequencies (or wavelengths) that cannot propagate in a given structure. As a result, the PBGs give a colored appearance to structures without the presence of chromophores. The local radiative density of states (LRDoS) increases near the edge of a PBG and then becomes smaller and approaches zero at the PBG. This is important for measurements of fluorescence because the rate at which an excited fluorophore loses energy to the PC increases with an increase in the LRDoS.

1.1 1DPC Functionalized Substrate

A one dimensional photonic crystal (1DPC) is robust and easy to fabricate using only vapor deposition methods, although other methods can also be used. A 1DPC consists of multiple layers of dielectrics with alternating low (L) and high (H) dielectric constants. The dielectric constant κ is equal to the square of the index of refraction, n. These structures can display a partial PBG and become completely reflective for particular wavelengths and incidence angles. However, this complete reflection refers to plane wave light incident from the far field.

Previous studies of fluorophores near metallic structures showed that fluorophores in the near field can interact with metals when plane wave illumination at the same frequency is reflected. As described herein, a similar near field effect occurs with 1DPCs. It was found that fluorophores can also undergo near field interactions and couple with modes of the 1DPC at the same wavelengths (optical frequencies) at which far field illumination results in reflection. These interactions were found to modify the directionality and polarization of the coupled emission. This phenomenon is called herein Bragg grating-coupled emission (BGCE).

There are several potential advantages when using dielectric structures. Metals are lossy, meaning that they rapidly dissipate energy. Dielectrics dissipate less energy than metals, which can allow sharp resonances and strong local fields. Fluorophores will not be quenched when close to the surface of a dielectric; hence, enhanced emission is possible for the entire evanescent field, not just the region beyond 3 nanometers (nm, 1 nm=$10^{-9}$ meters) from the surface as observed for metal structures. A wide variety of dielectrics are available to cover a wide range of wavelengths, and the optical properties (e.g., n) can scale closely with dimensions. In addition, the substrates are not as fragile as metal surfaces and can be cleaned and used multiple times.

Excited state fluorophores can interact with 1DPCs in several ways. FIG. 1A is a block diagram that illustrates example interactions of a fluorophore 180 with a one dimensional photonic crystal (1DPC) 101, according to various embodiments. If the fluorophore 180 is more than approximately 1 wavelength away (panel A), the energy propagates as free space radiation. If the wavelength overlaps with the PBG, it is reflected (R). This effect was used in several studies as a way to collect a greater fraction of the emission from a fluorophore. Alternatively, if the wavelength is much longer or much shorter than the thickness of the layers (panel B), the light can be transmitted (T). The width of the PBG depends on the relative values of the two dielectrics, and harmonics can also be transmitted. Typically a PBG bandwidth is about one-fourth of the fundamental PBG wavelength; but, the bandwidth can be larger or smaller depending on the value of the refractive indices. There are also harmonics in a PBG. factor of four If the wavelength is comparable to the layer thickness, and the emitter is within one wavelength of the 1DPC (panel C and panel D), then the emission can display near-field coupling with optical modes of the 1DPC.

One type of optical mode is made up of internal modes of the 1DPC (panel C). At first glance, it seems that this energy would be trapped by total internal reflection (TIR). However, as shown below, the majority of the radiation appears below the substrate as 1DPC coupled emission. This effect might occur because these modes are leaky, which depends on imperfections in the structure. A cone of emission and its angles in the substrate are expected to be dependent on wavelengths so that the 1DPC also provides spectral separation, as shown in some example embodiments below.

Another type of optical mode is made up of surface states on PCs (panel D). These surface states were recognized only recently, and their use in applications is even more recent. In these states, the electromagnetic energy is trapped on the surface. The energy cannot propagate into the sample because of the PBG and cannot radiate away from the surface because of TIR. These states are called Bloch surface waves (BSWs). The BSWs are analogous to surface plasmons, which are also surface-trapped states. Because of the low losses in dielectrics, the BSWs display high-quality factors and very sharp angular resonances. This provides an opportunity for nearby fluorophores to interact with these surface modes and display BSW-coupled emission (BWCE). BSWs provide opportunities both for selective excitation of surface-bound fluorophores and for a sharp angular distribution in the coupled emission. Although not stated explicitly, BSWs may have contributed to recently reported increased rates of excitation. Because of these unusual effects, 1DPCs offer opportunities for new formats for fluorescence detection and sensing.

Figure 1B:
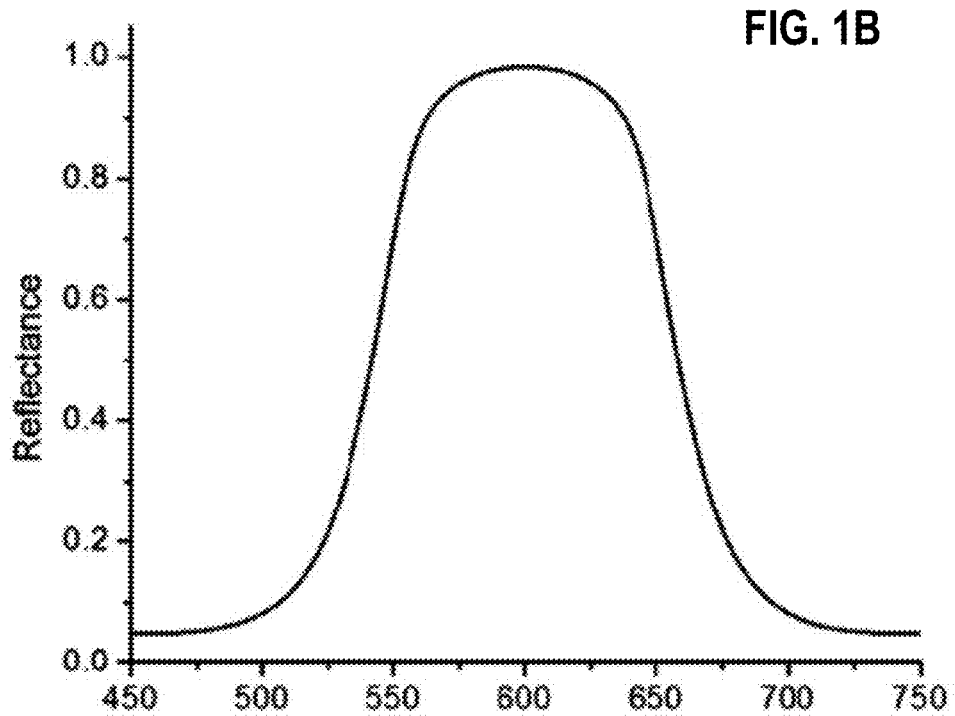
FIG. 1B through FIG. 1E, are graphs that illustrate example interactions of a fluorophore with 1DPC at various optical frequencies represented by their corresponding wavenumbers in air, according to various embodiments.
Figure 1C:
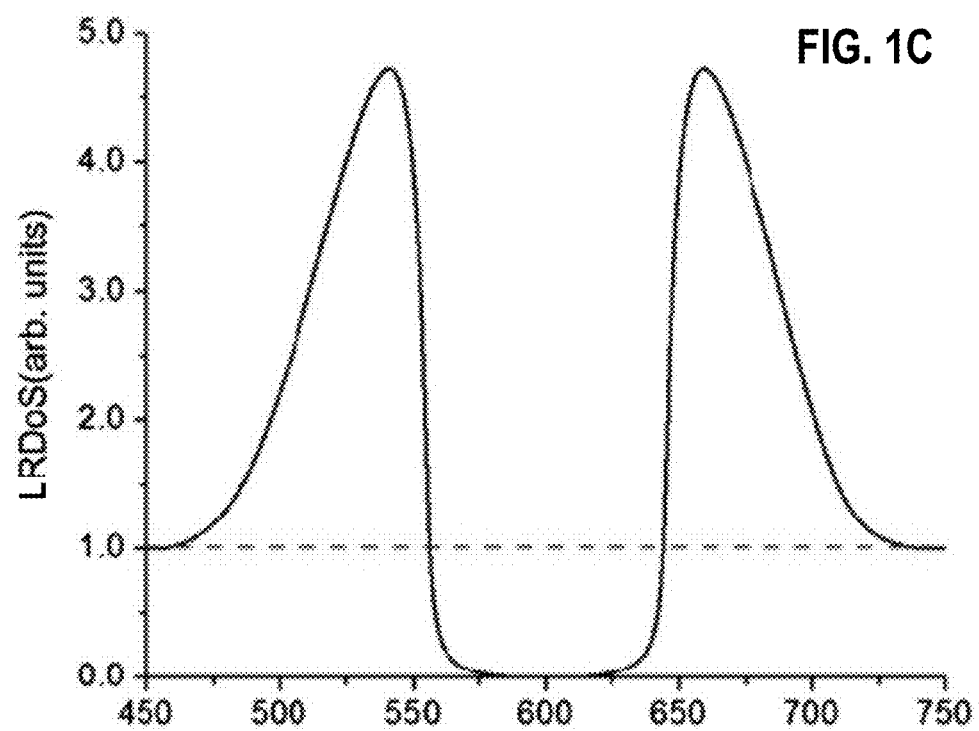
Figure 1D:
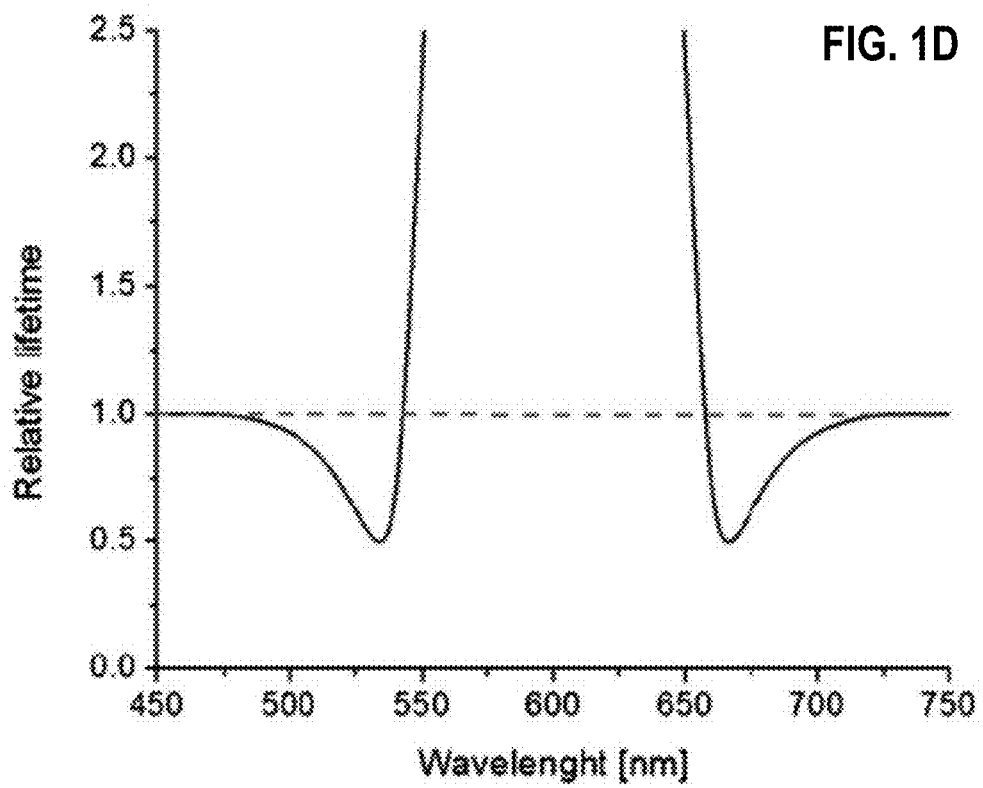
Figure 1E:
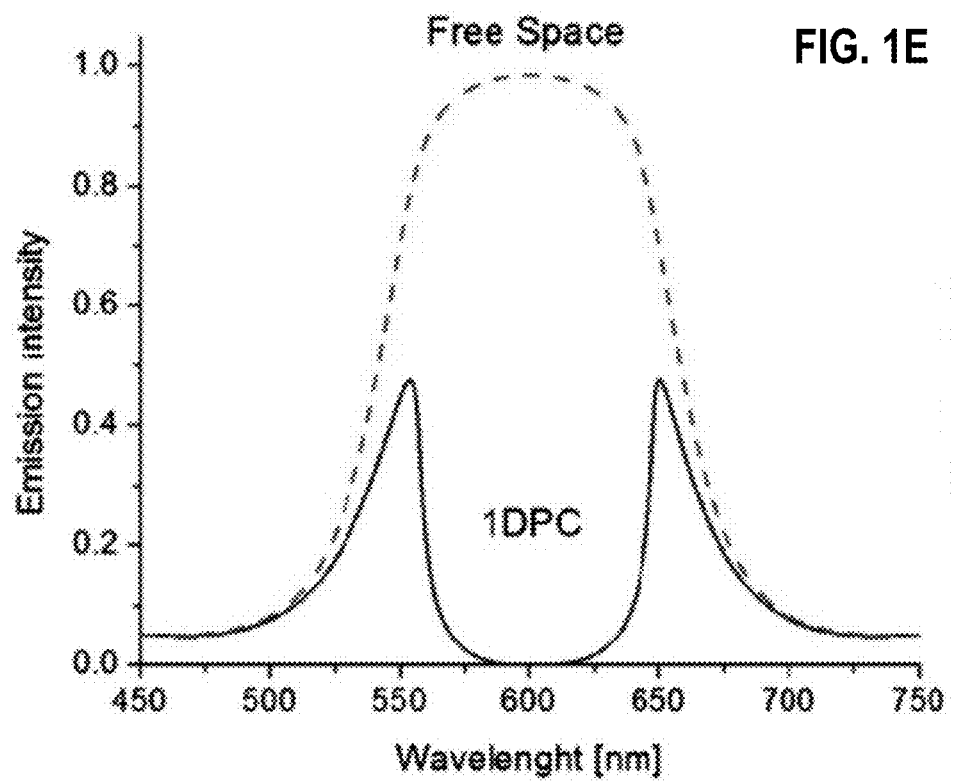

In a homogeneous solution, such as a fluorophore in water, the LRDoS is essentially constant in all locations, in all directions, and for all orientations of the dipole. In contrast, the LRDoS can vary dramatically near a PC. FIG. 1B through FIG. 1E, are graphs that illustrate example interactions of a fluorophore with a 1DPC at various optical frequencies represented by their corresponding wavenumbers in air, according to various embodiments. These figures do not show calculated results based on LRDoS, but rather show increases or decreases relative to the free space density of states that have been reported in the literature. In each of FIG. 1B through FIG. 1E, the horizontal axis indicates wavenumber in air in nanometers (nm, 1 nm=$10^{-9}$ meters). In FIG. 1B, the vertical axis indicates reflectance in fraction of incident light. Near total reflection occurs in the PBG around 600 nm, e.g., from about 575 nm to about 625 nm. In FIG. 1C, the vertical axis indicates a relative amount of radiative density of states. As can be seen, there are almost no states in the PBG; and, there is a large surplus of such states within about 75 nm adjacent to the PBG. In FIG. 1D, the vertical axis indicates relative lifetime of the emission from the fluorophore. Near infinite lifetimes occur in the PBG and long lifetimes nearby followed by a minimum in lifetime at some wavelengths. In FIG. 1E, the vertical axis indicates emission intensity relative to emission from the fluorophore in free space. Emission intensity peaks where there are peaks in the radiative density of states (FIG. 1C), but the intensity is less than half of the intensity in free space. This reduced intensity is acceptable because of the increased lifetime, and, as will be shown below, enhanced excitation and focused emission in particular directions.

Thus, as shown in these figures, LRDoS approaches zero in the PBG, which is seen by the increase in reflectivity at the center of the PGB. A less well-known effect is the increase in the LRDoS at the edges of the PBG. Depending on wavelength and orientation, a fluorophore can display either an increased lifetime for a low LRDoS or a decreased lifetime for a high LRDoS. The emission spectrum can be reduced at wavelengths where there is a low LRDoS and increased where there is a high LRDoS. An indication of such changes in the emission spectra is noted below with S-polarized emissions with reference to FIG. 10A through FIG. 10D. However, at this time it is not known whether fluorophores will couple as efficiently with the LRDoS near photonic crystals as fluorophores couple with plasmonic structures. That is, the range of lifetimes that can be obtained with 1DPCs is not yet known. The actual situation is more complex than that shown in FIG. 1B through FIG. 1E, because the actual effect will depend on the location and orientation of the fluorophore and on the direction of the emission. These factors are described in the LRDoS, which occurs for a specific set of conditions. These figures show, however, that the 1DPC provides multiple and diverse opportunities for near-field control of dipole emission. Such conclusions are supported by the observations reported below.

FIG. 2A is a block diagram that illustrates an example emission cone from fluorophores on a 1DPC 201 when excited by incident light 240 from below, according to various embodiments. The 1DPC 201 comprises L layers 203 of low index of refraction and H layers 205 of high index of refraction. Deposited on one surface of the 1DCP is a functionalized layer 280 that is configured to bind with or include fluorescent probes 282 that each include a fluorophore. The functionalized substrate 220 is made up of the 1DPC 201 and layer 280 (the latter either before or after binding with the probes 282). In some embodiments, the functionalized substrate is disposed on a glass structure, such as a glass slide or prism, for example, the illustrated hemispheroidal glass prism 230. The purpose of the prism is to allow incident light above the critical angle for the 1DPC-air or 1DPC-sample interface. The prism is also advantageous to allow light to be extracted from the bottom. Otherwise, the total internal reflection occurs at the bottom of the glass slide.

The fluorophore in the probes 282 is excited by excitation incident light 240 at incident angle θinc 241, which is greater than the critical angle for the L layer 203 and the functionalized layer 280, to attempt total internal reflection (TIR) as evident from the minimal reflection at ray 242. As shown below, this angle is chosen to increase the opportunity to activate a BSW at the top of 1DPC 201. The emissions are expected at angles that are independent of the excitation angle. The emission angles are represented by the angle θ$_F$ 251 and a spread over angular width 252. In some embodiments, different wavelengths occur at different angles within this angular spread 252, thus providing spectral separation of the emission band. This emission cone intersects a plane, such as a charge-coupled device (CCD) array, in an annular region 250 of high intensity.

The annular region can be predetermined using calibration measurements or theoretical simulations, as described below, or some combination, such as using observations to fit one or more parameters of the simulation. A detector focused in this predetermined annular region is expected to benefit from a higher signal to noise ratio or greater dynamic range or both, thus enhancing the fluorescent sensing, imaging and assays with the simplicity of a detector fixed at a predetermined angle relative to the 1DPC.

Figure 2B:
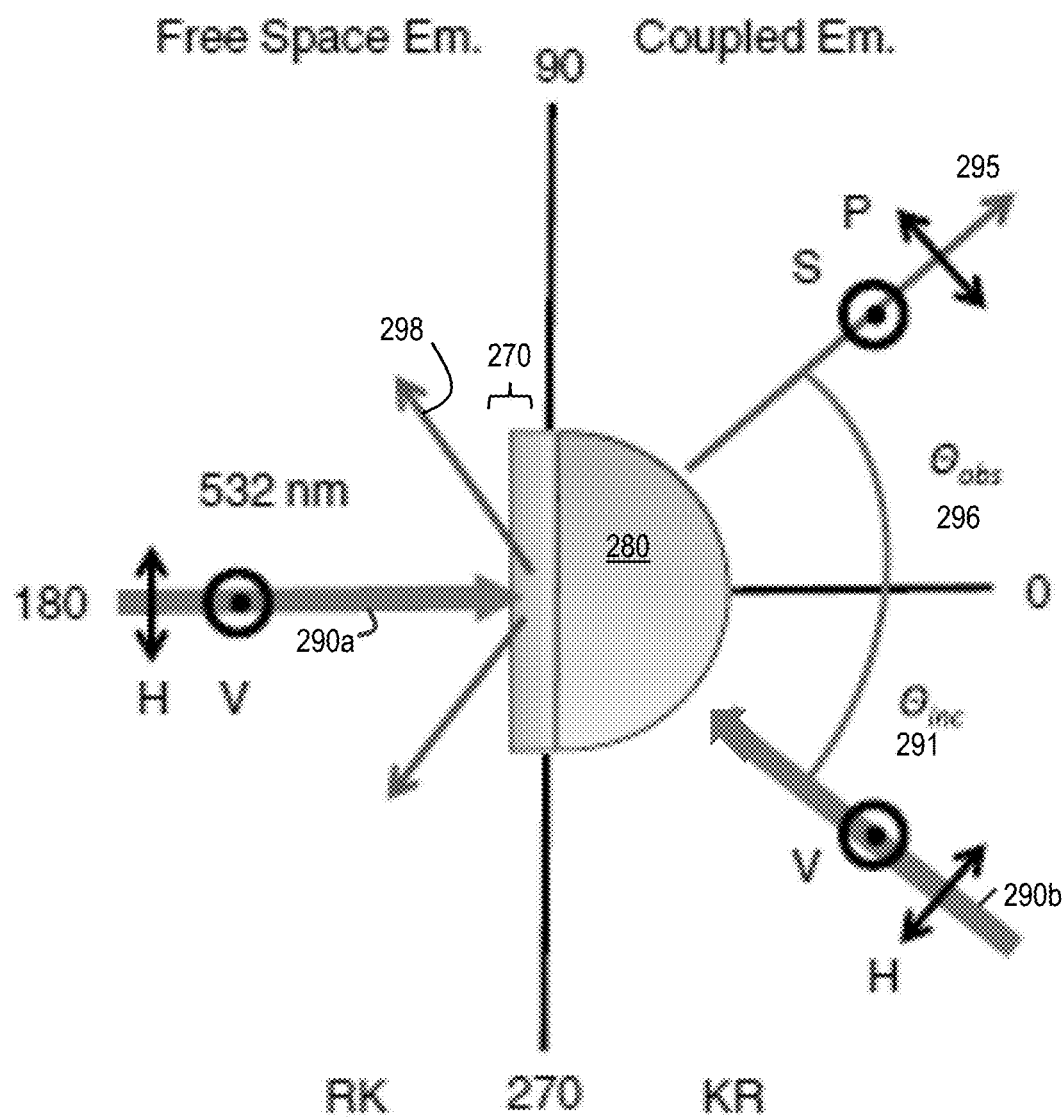
FIG. 2B is a block diagram that illustrates an example coordinate system for describing emission cone from fluorophores on a 1DPC when excited by incident light, according to various embodiments.

FIG. 2B is a block diagram that illustrates an example coordinate system for describing emission cone from fluorophores on a 1DPC when excited by incident light, according to various embodiments. The geometry and polarization conditions of the measurements are depicted in FIG. 2B. An arbitrarily chosen vertical axis in the laboratory corresponds to the out-of-plane axis in FIG. 2B. A rectangular 1DPC substrate 270 is placed on a hemi-cylindrical prism 280 with an index matching fluid and cylindrical axis parallel to the vertical axis (out of the page). The prism 280 is used to provide for a critical angle so that the incident light can be admitted in a direction above the critical angle (θc). Two modes of excitation were used. Excitation light 290b incident through the prism is called the Kretschmann (KR) configuration, and in some embodiments is incident above θc to allow selective excitation of fluorophores adjacent to the top surface of the 1DPC substrate 270 opposite the surface of the 1DPC substrate 270 that abuts the glass prism 280. In some embodiments, the substrate is also, or instead, excited with illumination 290a that does not pass through the prism 280, which is called the reverse Kretschmann (RK) configuration. In this case, fluorophores are excited through the entire thickness of the sample by light that has not passed through the 1DPC, and the incident light is reflected by the 1DPC substrate 270 as reflected light 298. The emission can be observed from either side of the substrate 270. Emission measured through the substrate and prism is referred to as coupled emission or KR emission; and, the emission that does not pass through the prism, is called free space emission or RK emission. The emission through the prism is expected to be polarized due to coupling to various modes in the 1DPC substrate. When describing Bragg grating (BG) structures, the S- and P-polarizations are defined relative to the planar surfaces of the substrate—S being parallel to those surfaces and P being perpendicular to the S direction. (Note that both S and P are perpendicular to the direction of propagation of the emission). Hence, the E-field for S-polarized light is parallel to the surfaces, and P-polarized light has its E-field across the interfaces. Because the out-of-plane axis is the laboratory vertical axis, S is referred to as vertically (V) polarized and P is referred to as horizontally (H) polarized. In the RK configuration, illumination was normal to the sample plane (from direction 180 degrees), but the same definitions for V and H were used to indicate the incident polarization relative to the observation polarization. Here vertical can be any direction relative to the direction of gravity. In some embodiments, the structure is used to analyze a liquid sample, and it is convenient for the direction from 180 degrees (toward 0 degrees) to be in the direction of gravitational acceleration.

As shown herein, these properties can be used to design a new family of sensors, assays or imagers for direct quantification of analytes, such as cytokines, at even very small concentrations, such as associated with cytokine secretion from a single cell, and in real-time.

1.2 1DPC Competitive Binding Assay

In some embodiments, the functionalized substrate 270 is used in a 1DPC competitive binding assay. FIG. 3A is a block diagram that illustrates an example 1DPC competitive binding assay 300 during operation, according to an embodiment. FIG. 3A depicts a portion of a functionalized substrate, including a glass substrate prism 304 and 1DPC 302. The functionalized substrate of FIG. 3A also includes fixed target molecules 332 for a particular analyte as the fixed bioactive molecules.

The functionalized substrate is in contact with a covering solution 310. The covering solution 310 is a mixture of a test sample and a detection molecule reagent. The test sample includes analyte molecules 320 that do not contain a fluorophore. The reagent includes detection molecules comprising analyte molecules 320 labeled with a fluorophore 330. In other embodiments, the detection molecule comprises a fluorophore and a molecule that is different from the analyte, but competes with the analyte for binding sites on the target molecules 332.

As shown in FIG. 3A, the labeled and unlabeled analyte molecules 320 compete for binding sites on the fixed target molecules 332, and eventually reach a steady state equilibrium. The combination of the functionalized substrate and covering solution in steady state is called a product of the assay.

The product of the assay is exposed to incident light 340 with an optical frequency that excites fluorescence of the fluorophore 330 and selected to couple with the modes of the 1DPC. In the illustrated example, the functionalized substrate and covering solution are exposed to linearly polarized incident light 340 indicated by dotted arrows.

The labeled analyte molecules are excited by the incident light and fluoresce, emitting light at a different specific wavelength. The fluorophore labels on analyte molecules that are free in cover solution 310 are typically not within one wavelength of the 1DPC 302 and their emitted light 340 passes directly out of the solution away from the 1DPC or is reflected without penetrating the 1DPC, as depicted in FIG. 1A panel A. For example, a labeled analyte in solution emits solution emitted light 342 indicated by a single dot dash arrow. In contrast, the fluorophore labels on analyte molecules that are bound to fixed target molecules 332 are within one wavelength pf the 1DPC, if the sizes of the target molecules, analytes and fluorophores 330 and target optical frequency are appropriately chosen. These emissions will couple with the 1DPC and be observed at the predetermined angles associated with the target optical frequency for the 1DPC. The compared reflected and coupled emissions can be used to determine the concentration of the analyte in the sample.

In some embodiments, the 1DPC is illuminated from below and excites a BSW that only excites the fluorophores 330 bound to the fixed target molecules 332. Again, these emissions will couple with the 1DPC and be observed at the predetermined angles associated with the target optical frequency for the 1DPC. The coupled emission intensity can be used to determine the concentration of the analyte in the sample.

The angular distribution of the emitted light is measured using an apparatus like apparatus 400 depicted in FIG. 4. The object 490 is the product of the assay, i.e., the functionalized substrate contacting the covering solution 310. A calibration curve constructed based on measurements made with known concentrations of the analyte can be used to determine the ratio of bound to free labeled analytes for a measured intensity value. Other calibration curves, as is well known in the art, are used to determine a resulting analyte associated with such a ratio of bound to free labeled analyte. The resulting analyte is used to determine the quantity (e.g., the presence, absence or concentration) of analyte in the test sample.

1.3 1DPC Sandwich Binding Assay

In some embodiments, the functionalized substrate 270 is used in a 1DPC sandwich binding assay. FIG. 3B is a block diagram that illustrates an example 1DPC sandwich binding assay 350 during operation, according to an embodiment. FIG. 3B depicts a portion of a functionalized substrate, including the glass prism 304 and 1DPC 302. The functionalized substrate also includes fixed target molecules 332 for a particular analyte as the fixed bioactive molecules.

The functionalized substrate is in contact with a covering solution 360. The covering solution 360 is a result of a three step process. First the functionalized substrate is contacted to a test sample that includes analyte molecules 370 that are not labeled with a fluorophore. The contact is maintained for sufficient time under conditions that allow the amount of analyte binding to the fixed target molecules 332 to be proportional to the amount of analyte in the test sample. Such times and conditions are easily determined by routine experimentation. Next, the functionalized substrate is washed to remove excess unbound analyte from the test sample. Then the functionalized substrate with bound analyte is contacted to a solution of reagent. The reagent includes detection molecules 372. Each detection molecule 370 includes a fluorophore 380 and a molecule that binds to the analyte 370 at a site on the analyte different from the site that binds the analyte to the fixed target molecule 332. The combination of the functionalized substrata, sandwiched analyte and covering solution in steady state is called a product of the assay. The sizes of the fixed target molecules 332, analyte 370, detection molecule 372 and fluorophore 380, and the target optical frequency are selected so that emissions are within one wavelength of the 1DPC.

The product of the assay is exposed to linearly polarized incident light at a specific wavelength that excites fluorescence of the fluorophore 380. In the illustrated example, the functionalized substrate and covering solution are exposed to polarized incident light 390 indicated by dotted arrows.

The fluorophores in the detection molecules are excited by the incident light and fluoresce, emitting light at the target optical frequency. The fluorophores on detection molecules that are free in cover solution 360 emit light more than one wavelength from the 1DPC. For example, a detection molecule in solution emits solution emitted light 392 indicated by a single dot dash arrow. In contrast, the fluorophores on detection molecules that are bound to the analyte that is in turn bound to the fixed target molecules 332 emit light that couples to the modes of the 1DPC. For example, detection molecules bound to analytes bound to fixed target molecules 332 emit film emitted light 394 indicated by a double dot dash arrow. The collection of these emissions indicates the amount of bound analyte.

Any molecule may be deposited in the bioactive molecule layer. The properties of the functionalized substrate are affected by the bioactive molecule deposited in layer. The molecule should include a functional group to affix the molecule to the substrate, such as a ligand to affix the molecule to a dielectric. The molecule should also be able to bind to a particular analyte of interest. Such a molecule is also called a target molecule for an assay for the analyte. In illustrated embodiments, all the molecules deposited in the layer are substantively identical. In other embodiments, functionalized substrates are designed for multiple analytes and multiple populations of different target molecules are used in the same substrate for corresponding different analytes. Binding events of the different analytes would be marked by fluorophores in corresponding different detection molecules emitting at different optical wavelengths. In various embodiments, target molecules that are deposited in the layer include, but are not limited to a polymer, a ligand, an antigen, an antibody, a protein, a peptide, DNA, RNA, or an oligonucleotide.

The functionalized substrate may be designed for any analyte to bind to an appropriately chosen target molecule. In various embodiments, the analyte includes, but is not limited to, a polymer, a ligand, an antigen, an antibody, a protein, a peptide, DNA, RNA, any form of RNA, an oligonucleotide, a virus, a bacterium or a cell.

1.4 1DPC Fluorescence Measurement System

FIG. 4 is a block diagram that illustrates an example enhanced fluorescence measurement system using a 1DPC, according to an embodiment. Although an object of measurement 490 is depicted in FIG. 4, the object 490 is not part of apparatus 400, but is operated upon by apparatus 400. In some embodiments, the object 490 is a product formed during an assay described above.

The system includes a source of incident light 410, a functionalized substrate 470, one or more optical couplers 412a and 412b, collectively called optical couplers 412, and a detector 450. The functionalized substrate 470 is configured to be placed in contact with a mixture of a sample and a reagent as an object of measurement 490. The functionalized substrate 470 includes a one dimensional photonic crystal for a target optical frequency and a bioactive target molecule that has an affinity for a particular analyte. The reagent includes a detection molecule for the particular analyte (the detection molecule includes a fluorophore that emits at the target optical frequency and binds to the analyte or the target molecule or both). The optical coupler is configured to direct incident light onto the functionalized substrate 470; and the detector 450 is configured to measure fluorescent emissions from the functionalized substrate 470. In the illustrated embodiment, the detector includes an optical fiber collector 452 and an optical sensor 454, such as a photomultiplier tube or spectral analyzer.

The optical couplers 412 includes one or more of any item that passes or affects an optical beam including any combination of components known in the art that are used to direct an optical beam, such as free space, vacuum, lenses, mirrors, beam splitters, wave plates and optical fibers, diffraction gratings, circulators, and prisms.

In various embodiments, the light source 410 or the optical coupler 412a or both are configured to be rotated to direct the incident light at one or more angles of incidence to the functionalized layer either by passing through the 1DPC, e.g., through the glass prism, or directly to the functionalized layer without passing through the 1DPC. In some embodiments, the detector 450 or coupler 412b or both are configured to be rotated to collect emitted light at one or more angles either by passing through the 1DPC, e.g., through the glass prism, or directly from the functionalized layer without passing through the 1DPC.

In some embodiments, the detector is configured for collecting fluorescent emissions in a collection cone that includes an angle of an emission intensity maximum that is independent of a direction of the incident light impinging on the substrate. In some of these embodiments, the coupler 412b includes a polarizer to pass only polarized light to the detector 450. In several of these embodiments, the emission intensity maximum is associated with a Bloch surface wave coupled emission (BWCE) or a Bragg grating coupled emission (BGCE) or both.

In some embodiments, the functionalized substrate or coupler 412a includes a glass prism abutting a surface of the one dimensional photonic crystal opposite a functionalized surface with the bioactive target molecule. In some of these embodiments, the optical coupler 412a is configured to direct the incident light to impinge on a surface of the one dimensional photonic crystal through the glass prism and at an angle of minimum external reflection. In some of these embodiments, the optical coupler further comprises a polarizer configured to polarize the incident light in a direction parallel to the plurality of dielectric layers. In some embodiments, the system includes a computer system or other controller configured with a 1DPC analysis module 482 configured to operate the light source or couplers 412 or detector 450 to collect data to form one or more calibration curves, or to use the calibration curves to perform an assay on the analyte based on the collected emissions.

Although processes, equipment, and data structures are depicted in FIG. 4 as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

1.5 1DPC Fluorescence Measurement Method

FIG. 5A and FIG. 5B are flow charts that illustrate an example method 500 to perform an enhanced fluorescence assay using a 1DPC, according to an embodiment. Although steps are depicted in FIG. 5A and FIG. 5B as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 501, a functionalized substrate is provided. In an illustrated embodiment, the functionalized substrate includes a 1DPC configured to couple with a target optical frequency to be used in an assay. The 1DPC includes multiple dielectric layers including multiple high index of refraction layers alternating with multiple low index of refraction layers. The thickness of each layer is within a factor of four of a wavelength of the target optical frequency in the layer. As a result, the 1DPC has particular angles of minimum reflection or maximum emission for each of one or more optical frequencies near a photonic band gap (PBG). In this embodiment, the functionalized substrate also includes a layer of one or more populations of substantively identical bioactive target molecules that bind to a particular analyte of interest for corresponding one or more analytes of interest. The functionalized substrate can be provided in any manner. In some embodiments the functionalized substrate is provided as depicted in FIG. 5B and described below.

In step 503, a reagent is provided, typically in solution. The solution of reagent includes a known quantity of a detection molecule comprising a probe and a fluorophore. The probe is selected to assay for the particular analyte. The probe is labeled with a particular fluorophore from the particular set of fluorophores with emission wavelengths suitable for 1DPC interactions. The reagent can be provided in any manner. For example, in some embodiments, the reagent is obtained from a commercial supplier. In some embodiments, the reagent is provided in an assay kit that also includes the 1DPC and the bioactive molecule in a separate container. In some embodiments the reagent is prepared locally by a user of the assay. In some embodiments, the reagent includes known concentrations of each of several different detection molecules, each with corresponding different fluorophores and each with affinities for corresponding different analytes, e.g., different cytokines secreted from a single cell.

Any molecule may be included as the probe in the detection molecule, such as a polymer, a ligand, an antigen, an antibody, a protein, an oligomer, a protein, a peptide, DNA, RNA or an oligonucleotide. Any fluorophore may be included in the detection molecule, such as fluoresceins, eosin, coumarines, rhodamines, cyanines, benzophenoxazines, phycobiliproteins or fluorescent proteins.

In step 505 a test sample is obtained with a quantity of a particular one or more analytes to be determined by the assay. During a calibration phase used in some embodiments, step 505 includes providing a control sample with known quantities of the one or more particular analytes. For assays that are previously developed, with a known calibration curve, a control sample is not used during step 505. The quantity (such as the presence or concentration) of each of the one or more analytes in the test sample is determined during step 515, described below. Any material may serve as one of the one or more analytes, such as a polymer, a ligand, an antigen, an antibody, a protein, a cytokine, a peptide, DNA, RNA, oligonucleotide, a virus, bacterium, or a cell from a patient.

In step 507, the functionalized substrate is contacted with the test sample and the reagent for sufficient time to produce binding of the one or more different detection molecules to the one or more different analytes or to produce binding of the one or more different analytes to the one or more different fixed bioactive target molecules. To monitor temporal progression of a cell-oriented process, steady state conditions do not need to be reached.

In step 509, the substrate and covering solution resulting from step 615 are exposed to excitation light that excites fluorescence in the one or more particular fluorophores corresponding to the different analytes.

In step 511 the relative intensity of emission electromagnetic waves is measured at the emission wavelength of the fluorophore corresponding to each of the one or more analytes. In some embodiments, the measurement of intensity or polarized intensity or direction or some combination is made relative to a reference, such as a reflected amount or an amount at a particular angle not associated with an emission maximums, or an angle of minimum intensity. In the illustrated embodiment, step 511 overlaps in time step 509, as the substrate and covering solution are excited and fluoresce measured at the same or overlapping times.

In step 513, a particular quantity of analyte bound to one or more areas on the functionalized substrate is associated with the measured value of relative intensity or polarization or direction or some combination. During a calibration phase, the known quantity of analyte in the control sample is associated with the measured values to add points to the calibration curves.

In step 515, one or more analyses of the sample are performed based on the quantities of the bound analytes. For example, one or more functions of an immune system cell are determined by a profile of cytokines secreted during measurement. As another example, a rate of secretion of the analyte by cell is determined based on a difference with a prior or subsequent measurement. In some embodiments, step 515 includes exposing the sample to one or more stimulants, e.g., to induce an immune reaction in a sample that includes one or more cells of an immune system.

In step 517, it is determined whether to make a measurement of the same sample at another time. If so, then control passes back to step 509 to expose the sample again to excitation electromagnetic waves. If not, then another sample, if any, is measured on another substrate, e.g., by returning to step 501 or step 505. In some embodiments, the next measurement is with another known quantity of analyte in another control sample to produce another point for the calibration curve. In a post calibration operational phase, a quantity on the established calibration curve associated with the measured intensity or polarization or direction, or some combination, is determined to be the quantity of the analyte in the test sample. The quantity indicates, for example, the presence, absence or concentration of the analyte.

In FIG. 5B a method 550 is depicted for providing a functionalized substrate. Thus method 550 is one embodiment of step 501. In step 551, it is determined which target optical frequency (and associated wavelength in air) is to be used for fluorescent detection or quantification of one or more analytes in a detector, an assay or imaging system. This information is used to determine which 1DPC structures are suitable for use.

In step 553 a 1DPC is obtained with photonic band gap adjacent to target optical frequency (and associated wavelength in air). In some embodiments, the substrate is obtained (e.g., from a commercial supplier) with both the 1DPC and layer of bioactive molecule. In some embodiments, the substrate is obtained with the 1DPC but without the bioactive layer, and the bioactive layer is deposited during step 561. In some of these embodiments the bioactive molecule is supplied and shipped in a separate container (e.g., to preserve its efficacy) as part of an assay kit, and deposited during step 561 to form the functionalized substrate when desired for use.

In some embodiments, step 553 includes step 555 for simulating the optical frequency and angular response of multiple trial 1DPC designs using one of the electric field modeling packages available. For example, in the embodiments described below, simulations of transmission and reflectance spectra were performed using several software packages, based on the transfer matrix method, all of which yielded nearly identical results. These packages are BR Project from the Institute of Electronic Materials Technology (Warsaw, Poland) and TFCalc from Software Spectra. As an initial configuration, the layer thickness is about one quarter a wavelength in the layer of the target PBG center optical frequency, and the number of layers is typically near 10 because 3 layers may not provide the full PBG, and a large number of layers decrease transmission.

In some embodiments, step 553 includes step 557 for fabricating the best 1DPC design determined in step 555. For example, in some of the embodiments described below a 1DPC was made by plasma-enhanced chemical vapor deposition (PECVD) of $SiO_2$ and $Si_3N_4$ on standard microscope slides. This structure consisted of alternating layers of $SiO_2$, with a low (L) refractive index, and $Si_3N_4$, as the high (H) refractive index dielectric. Other embodiments use other dielectrics including tantalum pentaoxide and other appropriate dielectrics suitable for different wavelengths regions of interest, such as the ultraviolet (UV) region of the optical spectrum. Dielectrics with suitable optical parameters are already known. The refractive index of $Si_3N_4$ can be adjusted by the relative amounts of silane and ammonia during deposition. Low-loss dielectric materials provides high-quality factors for resonances, which are expected to provide selective excitation of surface-bound species. The top layer can be silica or alumina, which provides well-known surface chemistry and easy conjugation of biomolecules. These structures do not require top-down nanofabrication methods and can be produced using only vapor deposition. The fabrication of 1DPC structures have also been reported using other methods such as layer-by-layer assembly and spin-coating methods.

In some embodiments, step 557 include making measurements of the actual layer thicknesses and optical properties and simulating the optical frequency and angular dependence based on the actual layer properties.

In step 561, a functionalized substrate is provided by depositing on the 1DPC a layer of one or more different bioactive target molecules with affinity for a particular set of one or more analytes, respectively. Some embodiments include step 563 to mount the functionalized substrate on a glass prism.

To determine the actual optical frequency and angular properties of the fabricated functionalized substrate, steps 565 through 575 are included in some embodiments. In step 565 it is determined whether testing will be done based on emissions from a fluorophore at the target optical frequency. If so, then in step 575 incident angles that produce maximum measured emission intensity at the target optical frequency are determined, as are the angles where the maximum emission is detected. In some embodiments, if these angles differ from the simulated values, one or more parameters of the simulations are adjusted during step 575 to achieve agreement. For example, absorption by one or more layers, modeled as an imaginary part of the index of refraction, is changed to give agreement with the actual angles and intensity of fluorescent emissions. Control then passes to step 581.

If it is determined in step 565 that testing will be not be done based on emissions from a fluorophore at the target optical frequency, then in step 571 incident angles of minimum measured reflection intensity at the target optical frequency are determined as a surrogate for angles of expected maximum emission. Similarly incident angles of minimum reflection at the excitation frequency are also determined for driving BSW production. In some embodiments, if these angles differ from the simulated values, one or more parameters of the simulations are adjusted during step 571 to achieve agreement. Control then passes to step 581.

In step 581, the particular angles of measured emission maximums, or measured reflection minimum or simulated emission maximum are provided for setting up the predetermined angles of measurement during sensing, assaying or imaging experiments. In some embodiments, step 581 includes simulations to associate one or more angles with modes of 1DPC interaction, such as BWCE or BGCE.

These 1DPC functionalized substrates eliminate the need for expensive nanoscale fabrication, provides large surface area to work with, which is suitable for various assay formats, and can be mass-produced at minimum cost. Additional benefits include: the fluorescence emission from different dyes can be conveniently tuned by changing the substrate parameters in a simple and straightforward manner. These substrates can be adapted for multiple uses such as fluorescence studies in multicolor directional fluorescence imaging and/or sensing of multiple probes or for molecule-specific bio-sensing, with a high degree of spatial control over the fluorescence emission. The layer numbers and thicknesses can be modified according to the desired photonic bandgap position.

It is proposed here that fluorescence detection with 1D photonic structures can become widely used in the biosciences, particularly for high-throughput testing and clinical applications. These uses will be facilitated by the favorable structural and optical properties of 1DPCs.

The possible uses of PC-coupled emission are increased by the presence of two types of coupling, e.g., coupling to internal modes and to BSWs of the PC. For a solid PC, the internal modes are confined within the structure and expected to be mostly insensitive to the optical properties (e.g., index of refraction and absorption) of the sample on the structure. Coupling to these modes can serve as an unchanging reference.

In contrast, the energy of the BSWs extends into the sample and, thus, can be used for selective excitation or coupled emission. In addition, the fraction of the energy that resides in the PC or in the sample can be adjusted by minor changes in the dimensions or optical constants. BSWs can be created with both S- and P-polarized incident light and can propagate on surfaces over distances of 200 μm. Recent reports have shown that Bloch surface waves can provide sub-diffraction limited resolution.

In addition, quenching for fluorophores, which are directly on the top surface, is not expected.

It is also noted that the BSW intensity profile is very sensitive to the assumed value of the imaginary part of the index of refraction for energy losses. These considerations suggest that highly selective excitation of surface-bound fluorophores is possible with 1DPCs and BSWs.

It is expected that these 1DPC structures to be useful for microscopy because the resonance angles are within the collection angle of most high NA immersion objectives. In a recent article, it was shown that BSW-coupled emission can be seen in microscopy.

It is further anticipated that BGCE from 1DPCs will provide a new approach to the design formats for detection and assays. The development of simple robust devices for sensing, methodologies in biotechnology and medical applications may take advantage of 1DPCs with assisted directional and wavelength-resolved emission. This is supported by the known ability to modify the direction of BSWs by refraction.

The use of photonic structures is a promising addition to the ongoing studies of fluorophores and near-field interactions.

2. EXAMPLE EMBODIMENTS

Here are described 1DPC substrates that provide fluorescence amplification for surface bound fluorophores within a wavelength of the 1DPC at fixed angles independent of angle of incident excitation light.

Figure 6A:
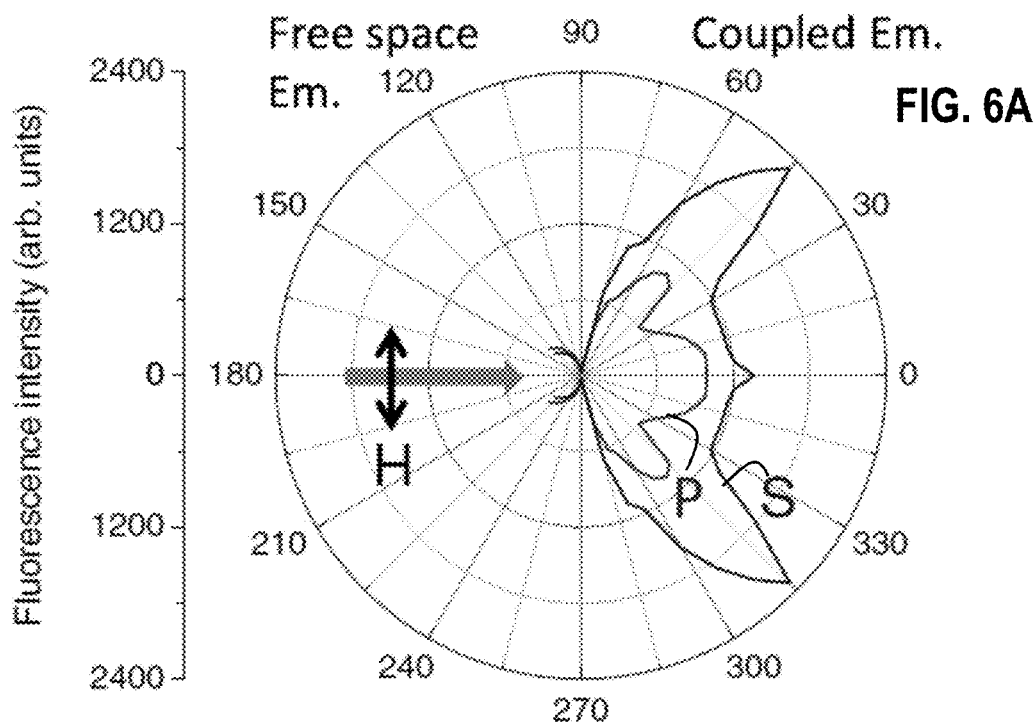
FIG. 6A and FIG. 6B are graphs that illustrate angle and wavelength dependence of fluorescence intensity in control experiments without a 1DPC.
Figure 6B:
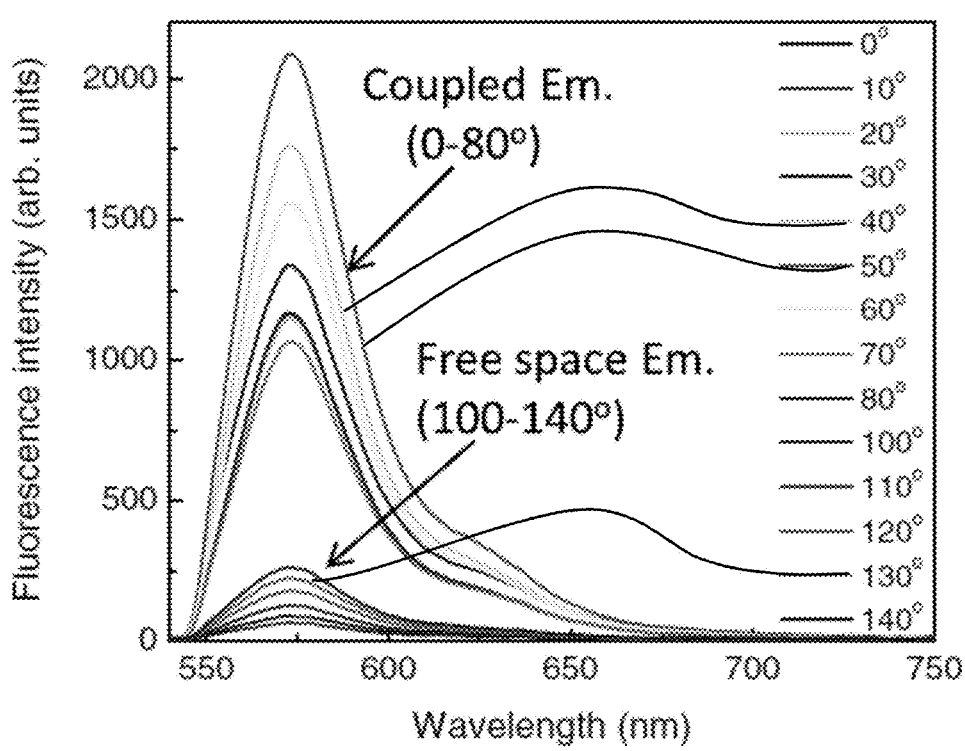

For comparison, a control device was also fabricated using the same fluorescent layer on glass instead of on an 1DPC. A glass slide was functionalized by subsequently coating with rhodamine B (RhB)-doped polyvinyl alcohol (PVA) in water, 1% PVA (MW=16,000-23,000), 3000 rpm, for 1 min, which yielded a thickness of 45 nm. FIG. 6A and FIG. 6B are graphs that illustrate angle and wavelength dependence of fluorescence intensity in control experiments without a 1DPC. FIG. 6A is a polar graph that illustrates example measured fluorescence intensity as a function of measured angle for illumination by horizontally polarized incident light incident from direction 180 degrees. The radial distance from the center of the graph indicates the amount of fluorescence according to the scale to the left in arbitrary units. Note that the scale maximum is 2400 units. The emission occurs over a wide range of angles. As expected, the majority of the emission occurs into the slide (coupled emission) due to its higher refractive index than air. FIG. 6B is a graph that illustrates example dependence of fluorescence intensity on optical frequency (expressed as wavelength in air). The horizontal axis indicates wavelength in nanometers, and the vertical axis indicates fluorescence intensity in arbitrary units, with a maximum over 2000. Multiple traces correspond to angles in ten degree increments for coupled emission (0 to 80 degrees) and free space emission (100 to 140 degrees). Consistent with FIG. 6A, the majority of the emission occurs as coupled emissions. No shifts in the emission spectra were observed for any observation angle. In contrast to the results shown below for the 1DPC, it was found that the RhB emission on the glass slide is only partially polarized. The trace for 50 degrees in FIG. 6B shows the maximum intensity, and has a spectral shape that closely represents the emission spectrum of the RhB fluorophore, which is useful for comparison to spectrally filtered emissions described in some embodiments below.

FIG. 7 is a block diagram that illustrates an example 1DPC, according to an embodiment. This 1DPC includes 7H layers of 78 nm thickness, and 6 L layers of 126 nm thickness, and a top L layer of $SiO_2$ that has a greater thickness of 152 nm. The targeted thicknesses were chosen because this structure was previously shown to display BSWs. The actual thickness and optical constants were determined using an N and K model 1200 instrument and are listed in Table 1.

TABLE 1

Measured optical constants for the Bragg grating structure

| Sample | Thickness (nm) | n or κ* | 270 nm | 550 nm | 633 nm | 900 nm |
|---|---|---|---|---|---|---|
| $SiO_2$ Si (κ = 0.0) | 126 | n | 1.496 | 1.460 | 1.457 | 1.452 |
| $Si_3N_4$ on Si | 78 | n | 2.473 | 2.196 | 2.144 | 2.051 |
|  |  | κ | 0.536 | 0.033 | 0.016 | 0.0007 |
| 1% PVA on Ag mirror (κ = 0.0) | 45 | n | 1.496 | 1.459 | 1.457 | 1.452 |
| Final $SiO_2$ layer (κ = 0.0) | 152 | n | 1.496 | 1.460 | 1.457 | 1.452 |

*The complex refractive index is defined as ñ = n + iκ

The 1DPC was functionalized by subsequently coating with rhodamine B (RhB)-doped polyvinyl alcohol (PVA) in water, 1% PVA (MW=16,000-23,000), 3000 rpm, for 1 min, which yielded a thickness of 45 nm.

Figure 8A:
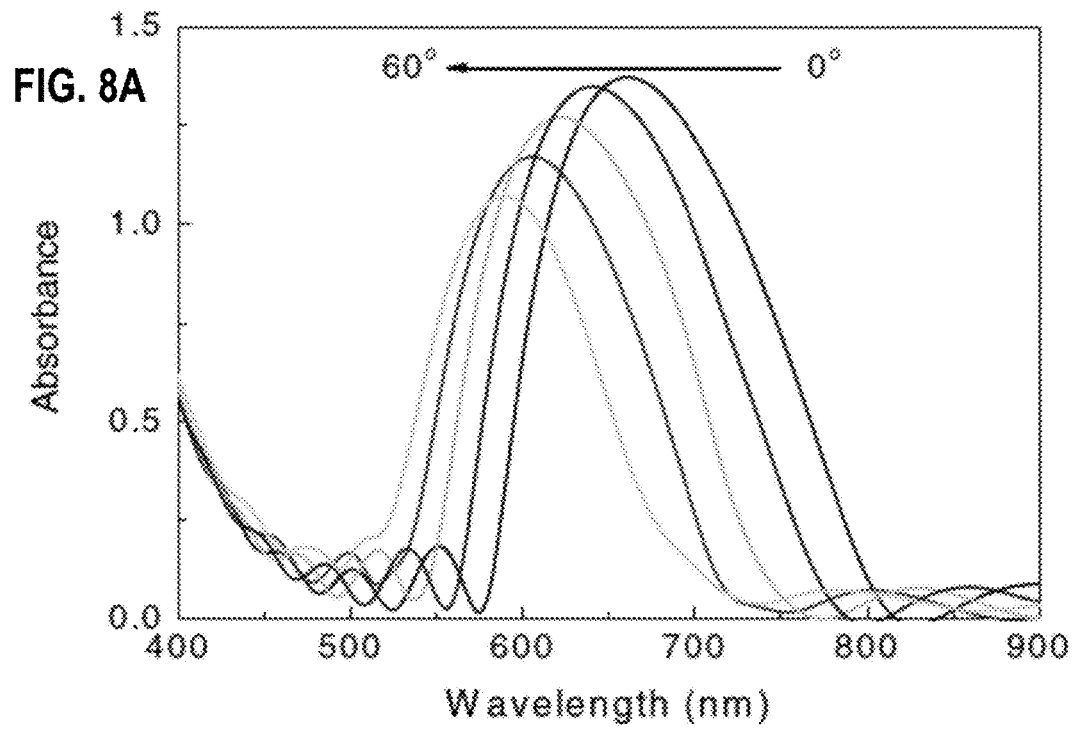
FIG. 8A is a graph that illustrates an example measured absorbance for a 1DPC, according to an embodiment.

FIG. 8A is a graph that illustrates an example measured absorbance for a 1DPC, according to an embodiment. The horizontal axis indicates optical frequency expressed as wavelength in air in nm; and, the vertical axis indicates absorbance. Each trace indicates the spectrum for a different angle of incidence, increasing from the spectrum with the rightmost peak at 0 degrees to the spectrum with the leftmost peak at 60 degrees. As the angle is increased, there is more transmission of red wavelengths below 700 nm. The high absorption near 670 nm is due to the PBG and overlaps the emission of RhB (see FIG. 6B). As expected for a Bragg grating (BG), the spectra shift to shorter wavelengths as the incidence angle is increased.

Figure 8B:
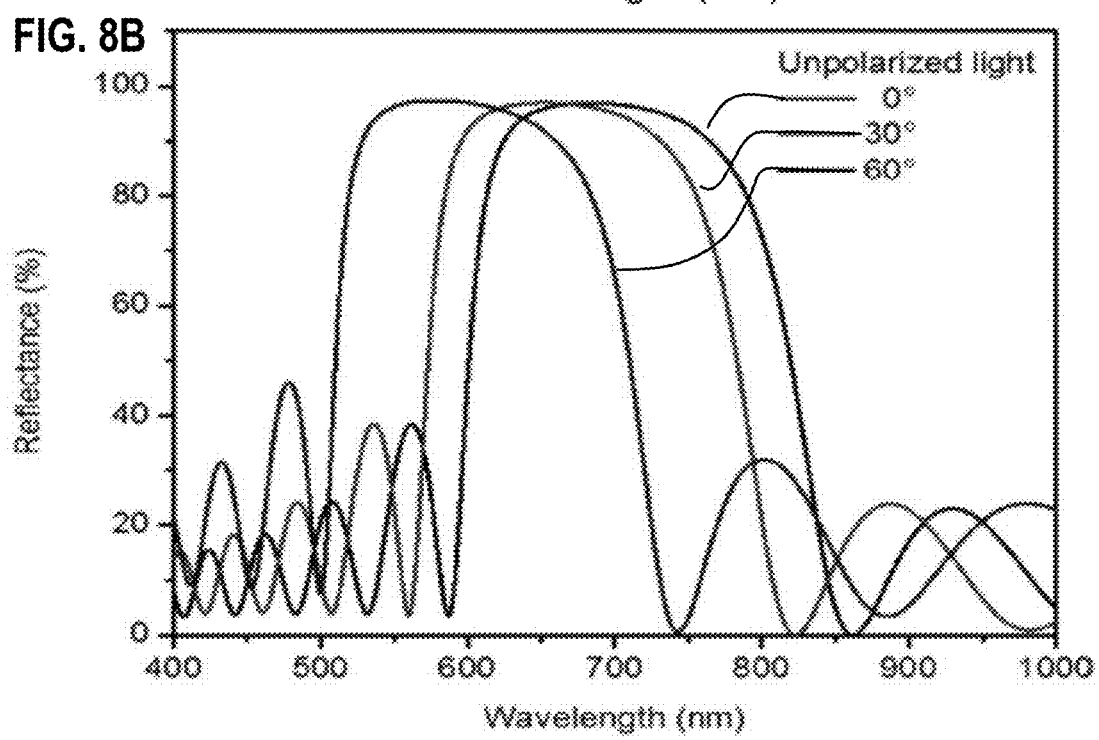
FIG. 8B is a graph that illustrates an example simulated reflectance for the 1DPC of FIG. 8A, according to an embodiment.

FIG. 8B is a graph that illustrates an example simulated reflectance for the 1DPC of FIG. 8A, according to an embodiment. The horizontal axis indicates optical frequency expressed as wavelength in air in nm; and, the vertical axis indicates reflectance in percent. Each trace represent the spectrum for a different angle of incidence. Near 100% reflectance indicates a PBG; and, the PGB band shifts to lower wavelengths as the angle of incidence increases. The simulated reflectance spectra are in good agreement with the measured spectra and display a similar dependence on incident angle. The harmonics on each side of the PBG are due to Fabry-Perot effects due to the finite thickness of the sample. These oscillations are smaller for the measured spectra, probably because of a less perfect cavity.

Figure 9A:
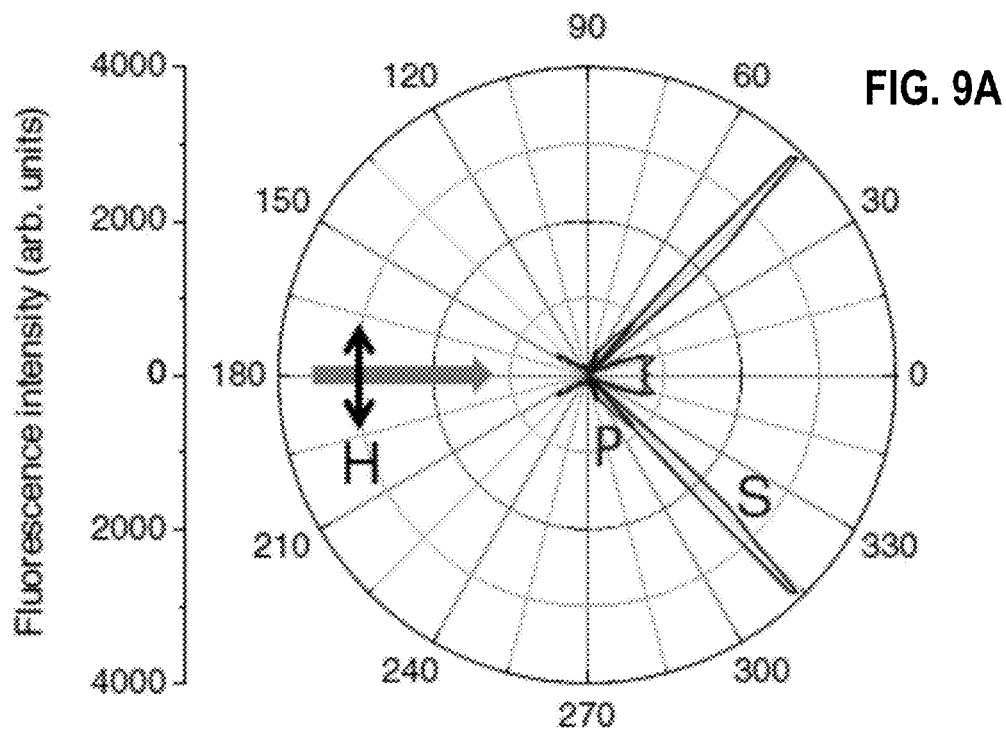
FIG. 9A and FIG. 9B are graphs that illustrate example measured angular dependence of fluorescence intensity for excitation by light incident without passing through the 1DPC, according to various embodiments.
Figure 9B:
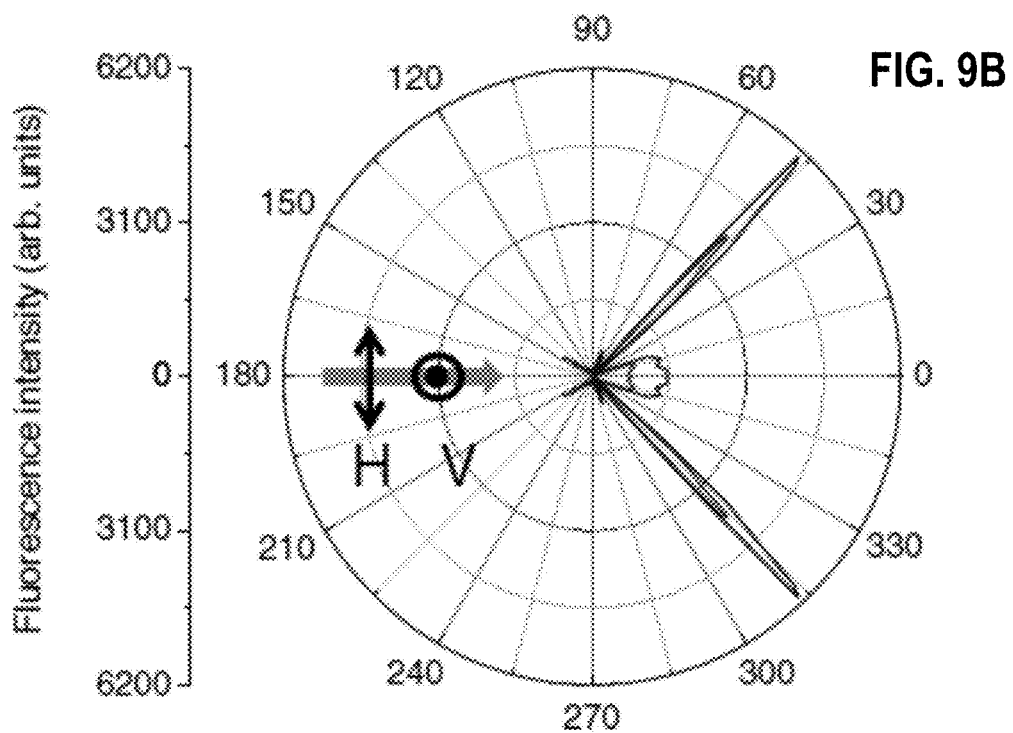

FIG. 9A and FIG. 9B are graphs that illustrate example measured angular dependence of fluorescence intensity for excitation by light incident without passing through the 1DPC, according to various embodiments. Recall that this is termed RK illumination or excitation. FIG. 9A is a polar graph that illustrates example measured fluorescence intensity as a function of measured angle for illumination by horizontally polarized incident light incident from direction 180 degrees. Note that the scale maximum is 4000 units. S-polarized emissions (also called S emissions) are much greater than P-polarized emissions (also called P emissions), and both are maximum in a narrow angle band at about +/−45 degrees, with secondary peaks at 0 degrees. Recall that S-polarized means polarized parallel to layers of 1DPC; and P-polarized is perpendicular to both S-polarized and the direction of propagation. FIG. 9B is a polar graph that for illumination by unpolarized incident light. Note that the scale maximum is even greater at 6200. S emission are about double P emissions at the same angles as in FIG. 9A.

With RK excitation, selective excitation of the fluorophores closest to the 1DPC is not expected, so that the excited fluorophores are not necessarily coupled to any modes in the 1DPC. Even without selective excitation, the emission was found to be highly polarized and sharply distributed over a small range of angles. The S-polarized emission was observed at an angle closer to the normal axis than the P-polarized emission in FIG. 9A. This distribution was observed for all of the samples independent of RK or KR excitation. The angle and intensity of the S-polarized emission was mostly independent of the excitation polarization as demonstrated in FIG. 9B. These results demonstrate that the fluorophores display near-field coupling with the 1DPC even when excitation occurs independent of optical modes in the 1DPC.

Figure 9C:
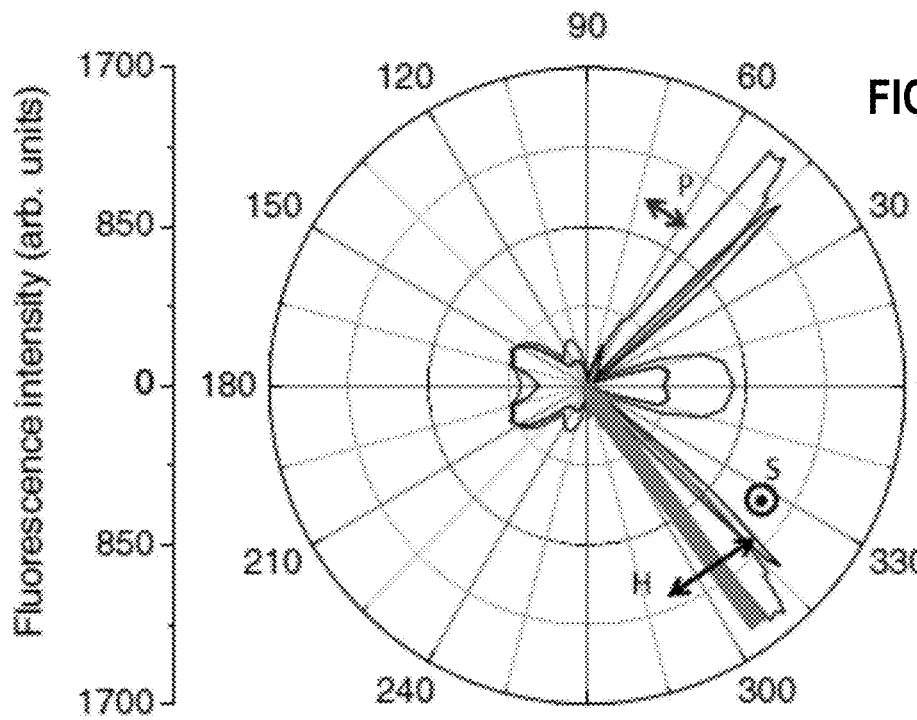
FIG. 9C and FIG. 9D are graphs that illustrate example measured angular dependence of fluorescence intensity for excitation by light incident through the 1DPC, according to various embodiments.
Figure 9D:
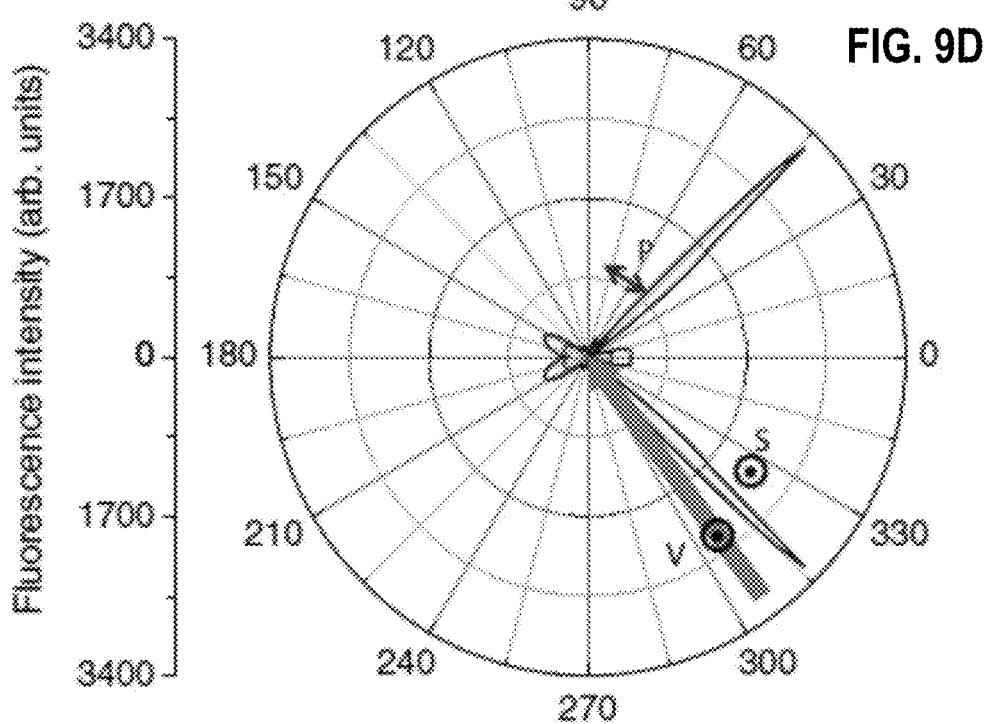

FIG. 9C and FIG. 9D are graphs that illustrate example measured angular dependence of fluorescence intensity for excitation by light incident through the 1DPC, according to various embodiments. Recall that this is termed KR illumination or excitation. FIG. 9C is a polar graph that illustrates example measured fluorescence intensity as a function of measured angle for illumination by horizontally polarized incident light incident from direction about −55 degrees (305 degrees). Note that the scale maximum is small at 1700 units. The P emissions at about +/−50 are angularly displaced from the S emission at about +/−45 degrees. FIG. 9D is for vertically polarized incident light. Note that the scale maximum is 3400, double that of FIG. 9C. P emissions are negligible.

The incident angle was adjusted to obtain the highest emission intensities and, thus, corresponds to a reflectivity minimum or to be in resonances with a mode in the 1DPC. The emission intensities were observed to depend strongly on the incident polarization. With H-illumination, higher intensities were found in the P-polarized emission (FIG. 9C). With V-illumination, the S polarized emission was dominant (FIG. 9D). These intensities are consistent with alignment of the polarizers. H-illumination is in the same plane with P-emission, and V-illumination is in plane with the S-emission. It is interesting to note that the smaller angle emission band is S-polarized. This is opposite of that found with metallic surfaces and surface plasmon-coupled emissions.

Figure 10A:
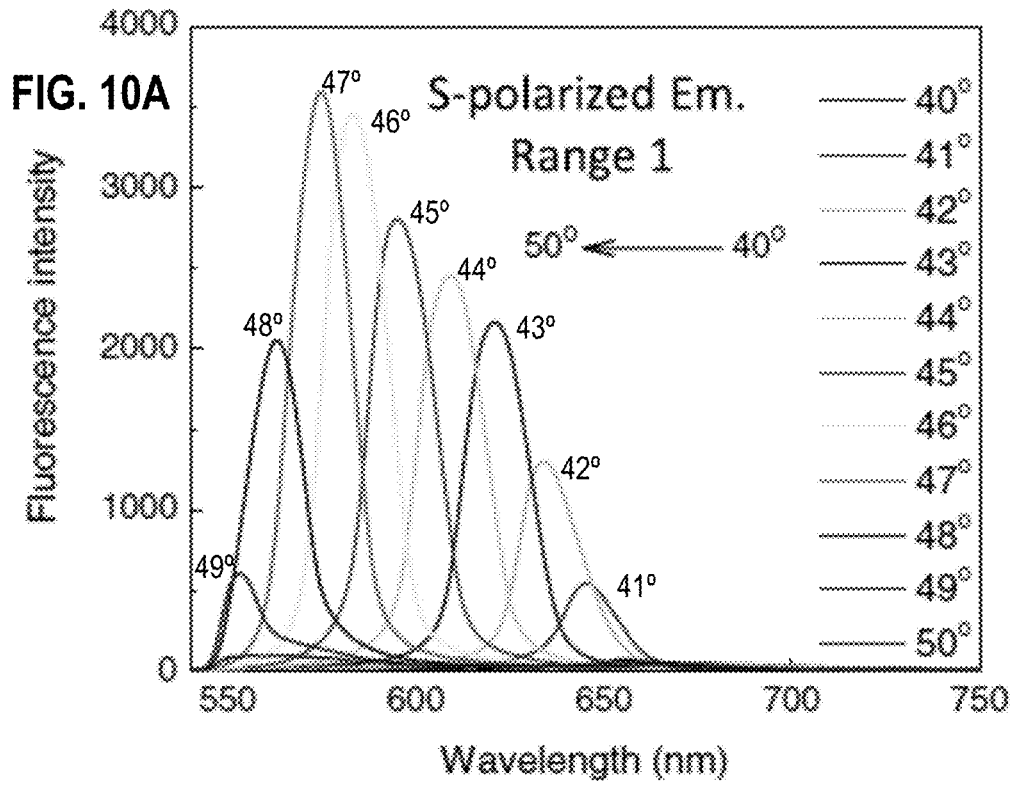
FIG. 10A and FIG. 10B are graphs that illustrate example measured optical frequency separation by angle for S-polarized emissions (polarized parallel to layers of 1DPC), according to an embodiment.
Figure 10B:
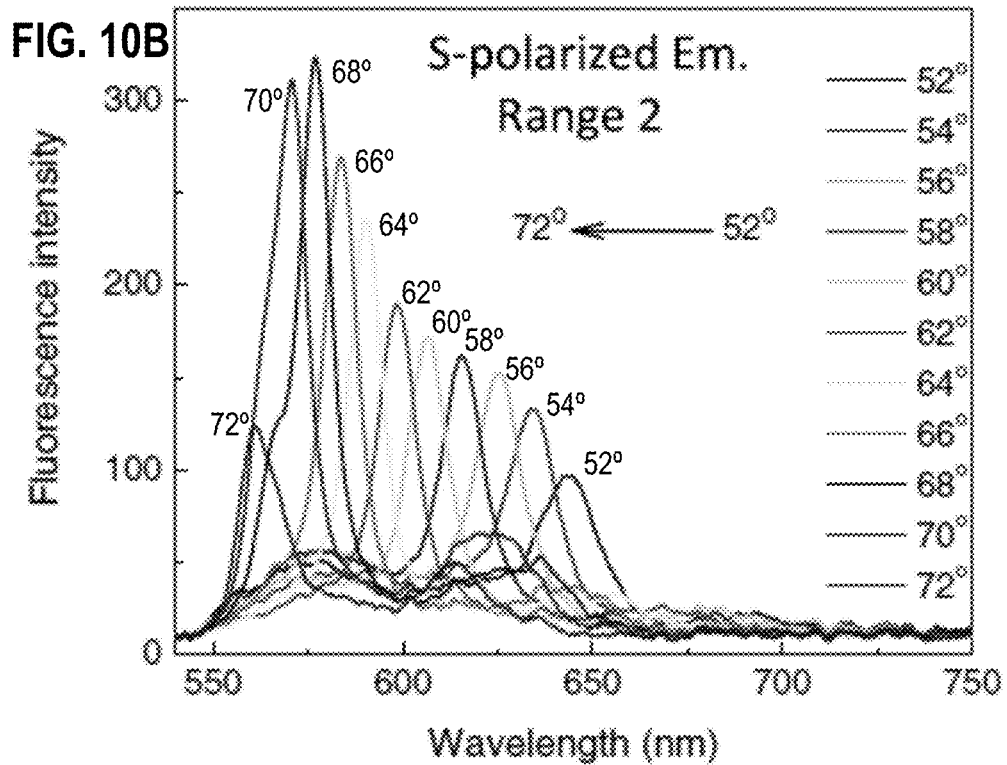
Figure 10C:
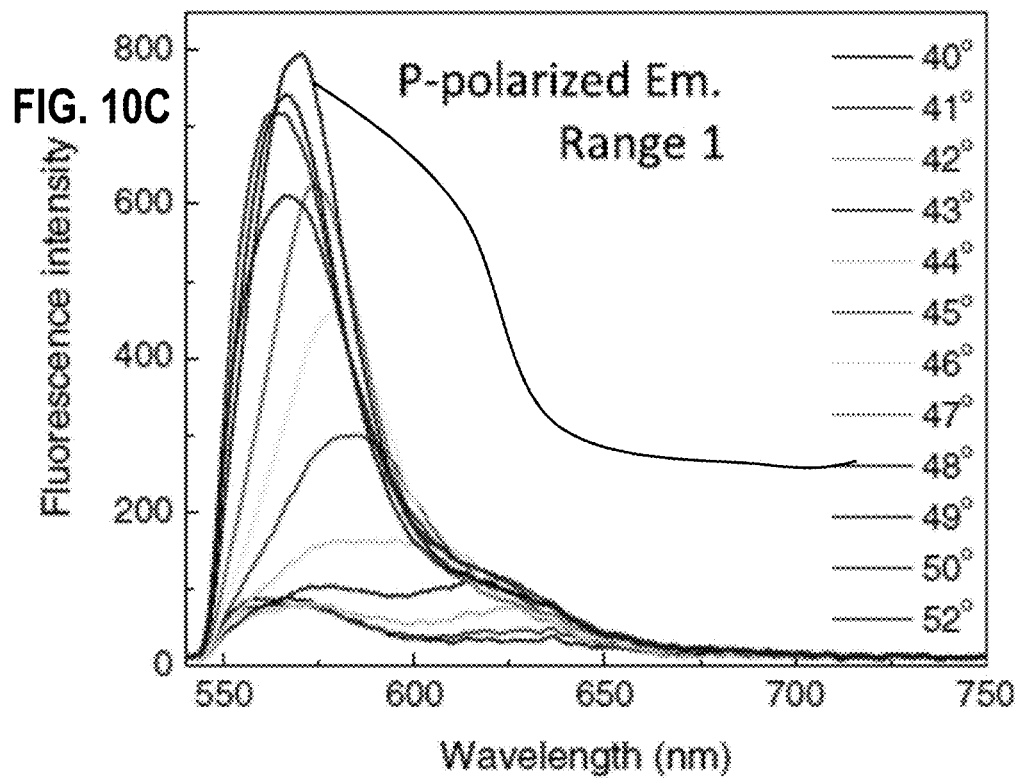
FIG. 10C and FIG. 10D are graphs that illustrate example measured lack of optical frequency separation by angle for P-polarized emissions (perpendicular to S-polarized and direction of propagation), according to an embodiment.
Figure 10D:
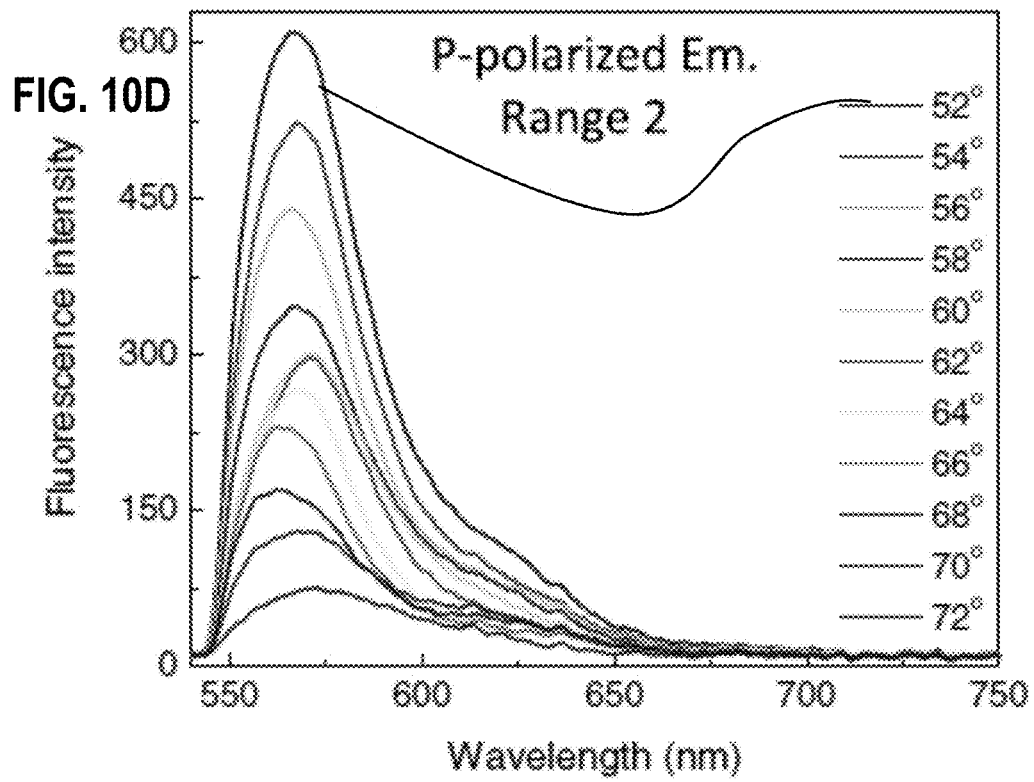

Different wavelengths are expected to appear at slightly different angles because of dispersion in the optical properties of the 1DPC. FIG. 10A and FIG. 10B are graphs that illustrate example measured optical frequency separation by angle for S-polarized emissions (polarized parallel to layers of 1DPC), according to an embodiment. On both plots horizontal axis indicates optical frequency expressed as wavenumber in air; and, the vertical axis indicates fluorescence intensity in the same arbitrary units. FIG. 10 is for a first range of angles from 40 degrees to 52 degrees, called range 1; and, FIG. 10B for a second range of angle from 52 degrees to 72 degrees, called range 2. Different optical frequencies are dominant at different angles in both plots, indicating spectral separation for S-polarized emission. FIG. 10C and FIG. 10D are graphs that illustrate example measured lack of optical frequency separation by angle for P-polarized emissions (perpendicular to S-polarized), according to an embodiment. On both plots horizontal axis indicates optical frequency expressed as wavenumber in air; and, the vertical axis indicates fluorescence intensity in the same arbitrary units. FIG. 10C is for a first range of angles from 40 degrees to 52 degrees, called range 1; and, FIG. 10D for a second range of angle from 52 degrees to 72 degrees, called range 2.

Thus, in both angle ranges, the S-polarized emission wavelength was found to depend strongly on the observation angle and the P-polarized emission to be relatively insensitive to the observation angle. Note that fluorescent intensities are much greater for S-polarized in range 1 than in the other graphs. In addition, the widths of the recorded spectra were narrower for range 2 than for range 1. As described below, we believe that the different widths are due to coupling to a BSW (range 1) or an internal mode of the PC with higher dispersion (range 2).

RhB intensity decays were measured on glass and on the 1DPC with different polarizer orientations. Several trends are informative. All of the intensity decays on the 1DPC are more rapid (shorter lifetimes) than on glass. This result indicates that the structure is not slowing the decay rate due to an altered DoS. The more rapid decays on the 1DPC suggest that coupling of the fluorophores with the 1DPC provides a pathway for more rapid decay, which is plausibly due to an increased DoS near the PBG. Because fluorophores are not expected to be quenched by the dielectric 1DPC, it seems likely that the more rapid decay is due to an increase in the radiative decay rate and not to an increased rate of non-radiative decay. In addition, the decay rates on the 1DPC are only weakly dependent on the polarization of the incident light. Furthermore, the intensity decay appears to be somewhat faster for the P-polarized emission than for the S-polarized emission, which is unexpected because the S-polarized modes have much higher quality factors than the P-polarized modes.

To determine the association of the two ranges with 1DPC interaction modes, simulations were performed to determine the effect of reflectivity on incident angle and how this depends on wavelength. For these calculations, the exact measured optical constants could not be used because the BSWs are extremely narrow if there are no optical losses. It is very likely that the example 1DPC displays some optical losses due to imperfections in the multiple layers. These losses would not be seen in measurements of the optical constants of single dielectric layers. Therefore it was useful to add small imaginary components (described below) that added finite widths to the BSWs.

FIG. 11A and FIG. 11B are graphs that illustrate an example simulated frequency separation by angle in reflectance from a 1DPC model tuned to observations, according to an embodiment. In both graphs the horizontal axis indicates emission angle and the vertical axis indicates reflectance as a fraction of the incident light. In FIG. 11A, two angle ranges were found where the reflectivity decreases.

Range 1 shows very sharp resonances, and range 2 shows wider resonances. In both cases, the calculated resonances appear only for S-polarized light. The reflectivity of the P-polarized light is high and mostly independent of incident angle above the critical angle. For both angle ranges, the S-polarized reflectivity is dependent on incident wavelength in a manner comparable to the wavelength shifts in the emission spectra (FIG. 10A and FIG. 10B). The sharp resonances in range 1 are highly dependent on the imaginary part of the refractive index. It was useful to fit the observations to include finite non-zero values of the imaginary part. Otherwise, the sharp resonances could be missed with the finite angular resolution of the calculations. In range 2, the resonances are independent of small values for the imaginary part. From the shapes and distribution of the resonances, it appears that the range 1 band was due to BSWs and the range 2 band was due to internal modes of the 1DPC. FIG. 11B is the result from simulations using a different value for the refractive index of the 45 nm thick functionalized layer.

Figure 12:
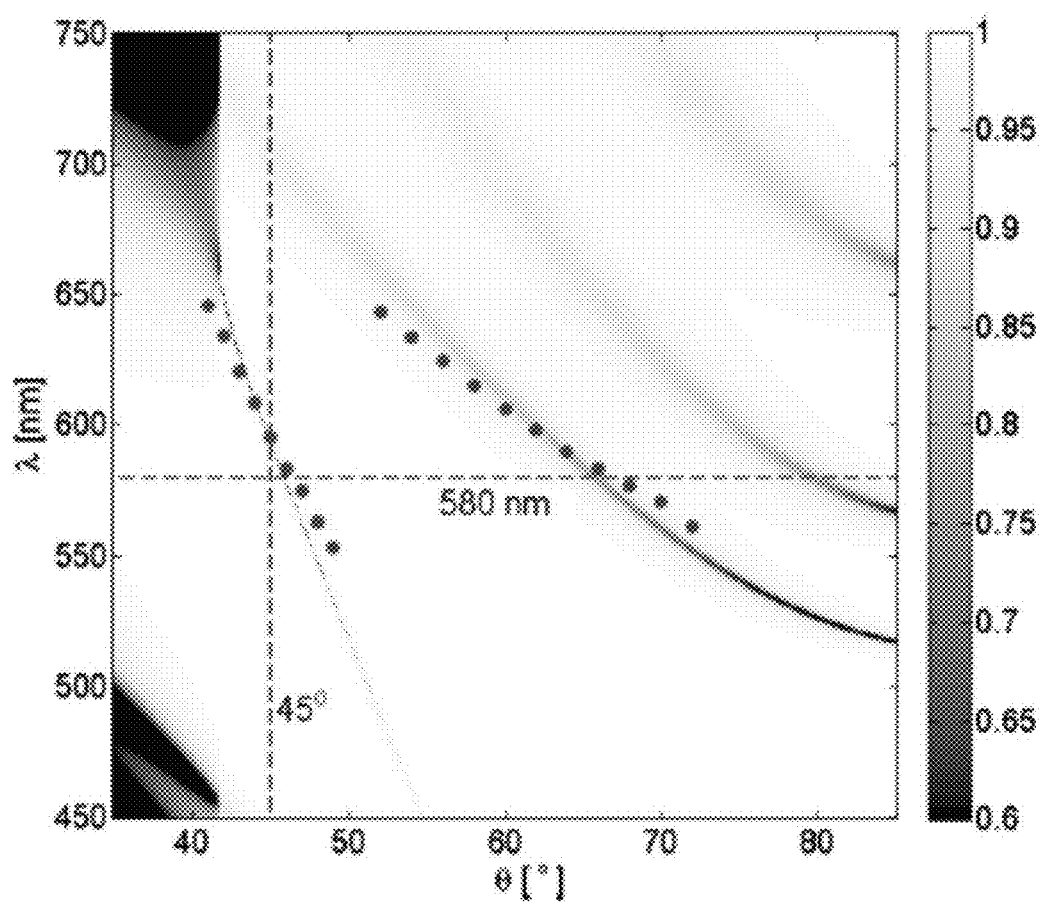
FIG. 12 is a graph that illustrates an example dispersion graph of simulated frequency separation by angle in reflectance from a 1DPC model tuned to observations, according to an embodiment.

The simulations in FIG. 11A and FIG. 11B are now compared with the dispersion diagrams as presented by the optics community. These dispersion diagrams are presented in varying degrees of complexity. FIG. 12 is a graph that illustrates an example dispersion graph of simulated frequency separation by angle in reflectance from a 1DPC model tuned to observations, according to an embodiment. The horizontal axis indicates angle in degrees from normal and the vertical axis indicates optical frequency as represented by wavelength in air, in nanometers. The bright areas indicates high simulated reflectivity and the dark areas low simulated reflectivity. Such plots are used because the reflectivity depends on both wavelength and incidence angle. This is in contrast to chromophores in which the absorption occurs at a fixed wavelength and does not depend on incidence angle.

At first glance, it can be difficult to correlate FIG. 12 with the experimental results in FIG. 10A through FIG. 10D. This correlation is aided by considering the reflectivity at a selected wavelength, which is shown by a horizontal line in FIG. 12. Consider the line at 580 nm. As the incident angle is increased, there is a narrow reflectivity dip near 45°. This corresponds to the BSW resonance seen at 45° for 580 nm in FIG. 11A. As the incidence angle is increased further in FIG. 12, there is a wider reflectivity dip near 65°, which corresponds to the wider resonances seen in FIG. 11A at this angle. For all wavelengths, the resonance angle increases as the wavelength decreases, consistent with FIG. 12A.

Another way to interpret these plots is to consider the reflectivity spectra at a given angle. Consider a vertical line in FIG. 12 at 38° (not shown in the figure for clarity). There is a wide region of high reflectivity (white area) from 500 to 700 nm, and the reflectivity decreases above and below these wavelengths. This spectrum corresponds to the reflectivity spectrum at normal incidence shown in FIG. 8B. Now, consider the reflectivity spectrum at 45°. In this case, the sharp BSW resonance is seen at approximately 550 nm. The BSW is not seen at an angle of incidence higher than 60°.

The calculated reflectivity was compared with the angle-dependent measured emission spectra shown in FIG. 10A through FIG. 10D. The dots in FIG. 12 represent the emission maxima and respective angles from range 10 (left) and range 2 (right) in FIG. 10A through FIG. 10D. The measured emission maximum at each angle is in excellent agreement with the BSW resonance in range 1 and the internal mode in range 2. This analysis highlights the mechanism leading to the observed emission properties. The small deviations are probably due to small differences between the optical properties of the single measured layers and the total composite structure.

To identify the resonances, we simulated the electric field intensities ($|E^2|$) for the example 1DPC for several wavelengths and incident angles. FIG. 13A and FIG. 13B are graphs that illustrate example simulated illumination-induced electric field intensity inside the 1DPC at optical frequencies inside and adjacent to the photonic band gap, respectively, according to an embodiment. For both plots the angle of incidence is zero degrees (normal incidence), and the horizontal axis indicates distance through the 1DPC from a glass prism through 14 dielectric layers to the functionalized layer (PVA) and then the air. The vertical axis indicates electric field intensity $|E^2|$ relative to no 1DPC structure (dimensionless).

For normal incidence at 680 nm, which is at the center of the PBG, the $|E^2|$ field is localized at the surface and decays exponentially in the IDPC (FIG. 13A). This effect occurs because the light is reflected; that is, the 680-nm light cannot propagate in the sample. Reflectance by a BG is different from that with a metal mirror. For a mirror, the field is sharply localized at the surface and penetrates only the skin depth of the mirror, which is typically near 20 nm. For a BG, the attenuation occurs over distances comparable to or larger than the wavelength.

For normal incidence at 580 nm, which is outside or near the edge of the PBG, the $|E^2|$ field exists within the 1DPC and the 1DPC is partially transmissive (FIG. 13B). This $|E^2|$ field corresponds to the reflectivity drop shown in FIG. 11A for 580 nm in range 2, indicating that the range 2 dips are due to internal optical modes in the 1DPC.

Figure 14A:
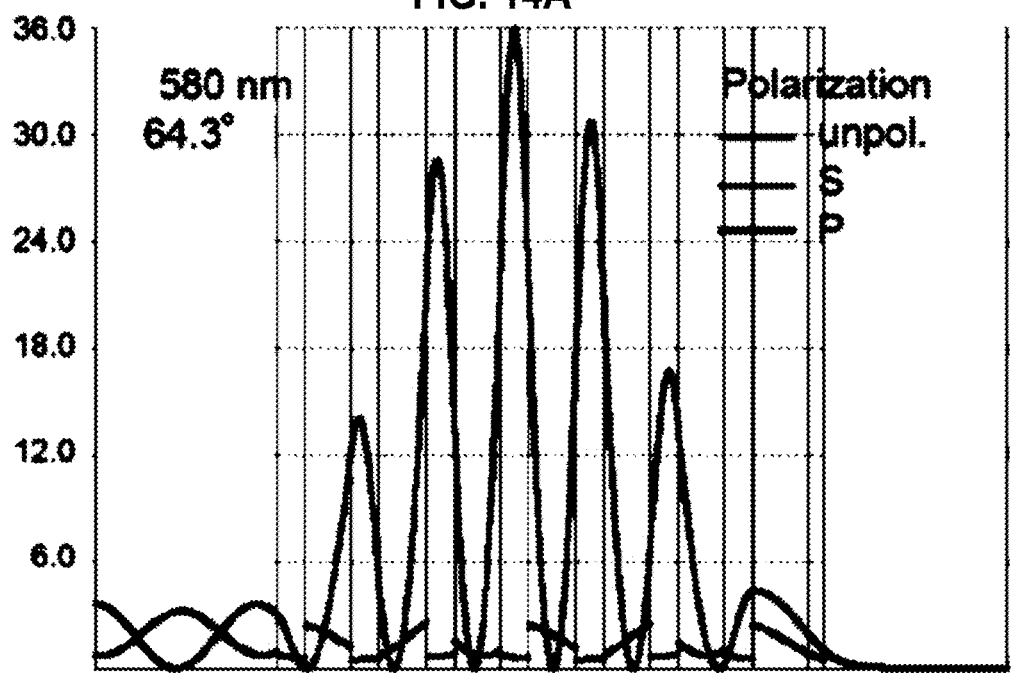
FIG. 14A and FIG. 14B are graphs that illustrate example simulated illumination-induced electric field intensity inside the 1DPCs at a target optical frequency for Bragg grating coupled emissions (BGCE) and Boch surface wave coupled emissions (BWCE), respectively, according to an embodiment.
Figure 14B:
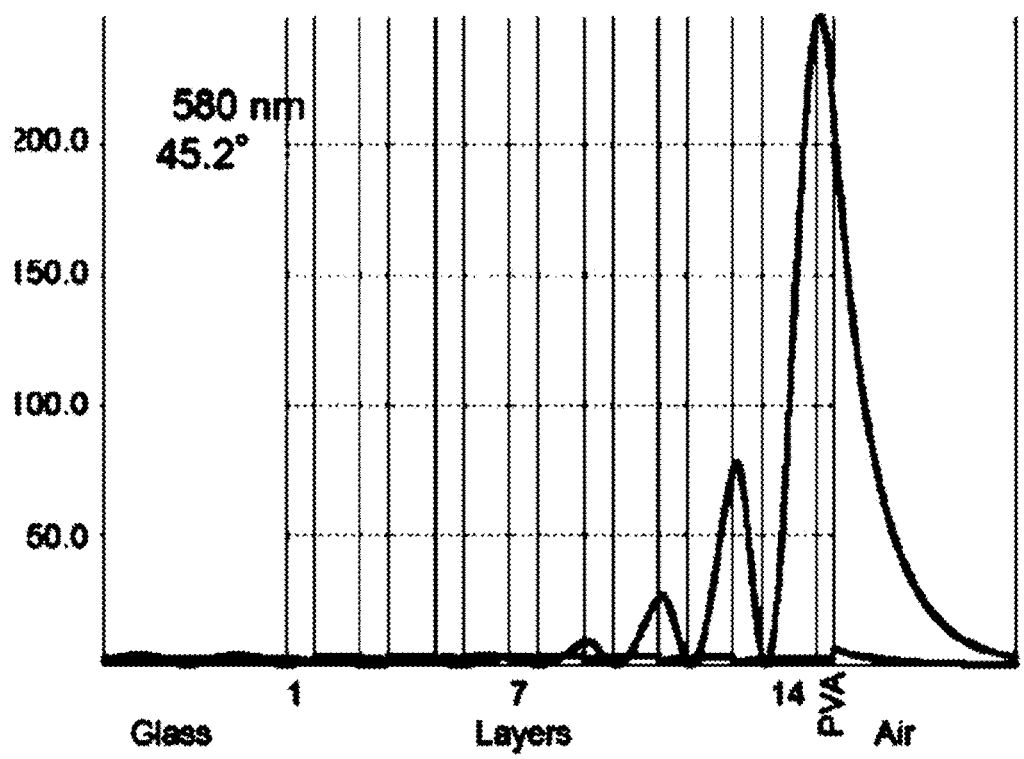

The $|E^2|$ field for 580 nm was also calculated for selected incident angles in range 1 and range 2. FIG. 14A and FIG. 14B are graphs that illustrate example simulated illumination-induced electric field intensity inside the 1DPCs at a target optical frequency for Bragg grating coupled emissions (BGCE) and Boch surface wave coupled emissions (BWCE), respectively, according to an embodiment. In range 2 at 64.3°, the $|E^2|$ field is centered in the 1DPC structure (FIG. 14A). A remarkably different result is found for 45.2° at 580 nm in range 1. In this case, the $|E^2|$ field is strongly localized on the surface of the 1DPC (FIG. 14B). In addition, the field intensity is much higher (nearly 100-fold higher) than for a reflected wavelength. These results demonstrate that the range 1 resonances are BSWs that have high-quality factors that allow the energy to build up at the surface. The potential fields in 1DPC are much higher than with metal films because of the higher dissipation losses in the metal films. FIG. 14B shows that the $|E^2|$ field due to the BSW penetrates into the sample, but the other $|E^2|$ fields are inside the 1DPC. This suggests that only the BSW mode should be sensitive to the optical properties (e.g., index of refraction and absorption) of the sample. This was confirmed by changing the refractive index of the top layer, which in the sample is 45 nm of PVA. A change in refractive index caused an angular shift in range 1 but not in range 2 (FIG. 11B), confirming this association of the resonances.

The previous calculations allow association of the fluorescence spectral data with optical modes in the 1DPC. In both range 1 and range 2, the measured emission maxima shift to shorter wavelengths at large observation angles (FIG. 10A and FIG. 10B), which is the same trend found in the simulations (FIG. 11A and FIG. 11B). We associate the emission in angle range 1 to BSW-coupled emission and associate that in range 2 to internal mode-coupled emission (IMCE).

The observed emission spectra are narrower in range 2 than in range 1. At first glance, this is counterintuitive because of the wider resonances in range 2 in FIG. 11A. However, the angle wavelength dispersion is higher in range 2. As a result, it is believed that a smaller range of wavelengths is captured by the optical fiber aperture of collector 452 in range 2, leading to the more narrow spectra. The overall dispersion and spectral narrowing in the S-polarized emission might be the result of modifications in the DoS by the PBG.

Another favorable property of PCs is the possibility of large enhancements of local fields with BSWs as indicated by a comparison of the field intensities for the 1DPC and for a continuous silver film on a glass prism. The high losses in the Ag film limits the evanescent field intensities to approximately 50-fold. In addition, the emission is quenched at distances below 5 nm from the metal surfaces. In contrast, the evanescent fields can be increased 1000-fold or more with a BSW on a 1DPC. This is possible because of the lower losses in the dielectrics.

3. Computer Hardware Overview

Figure 15:
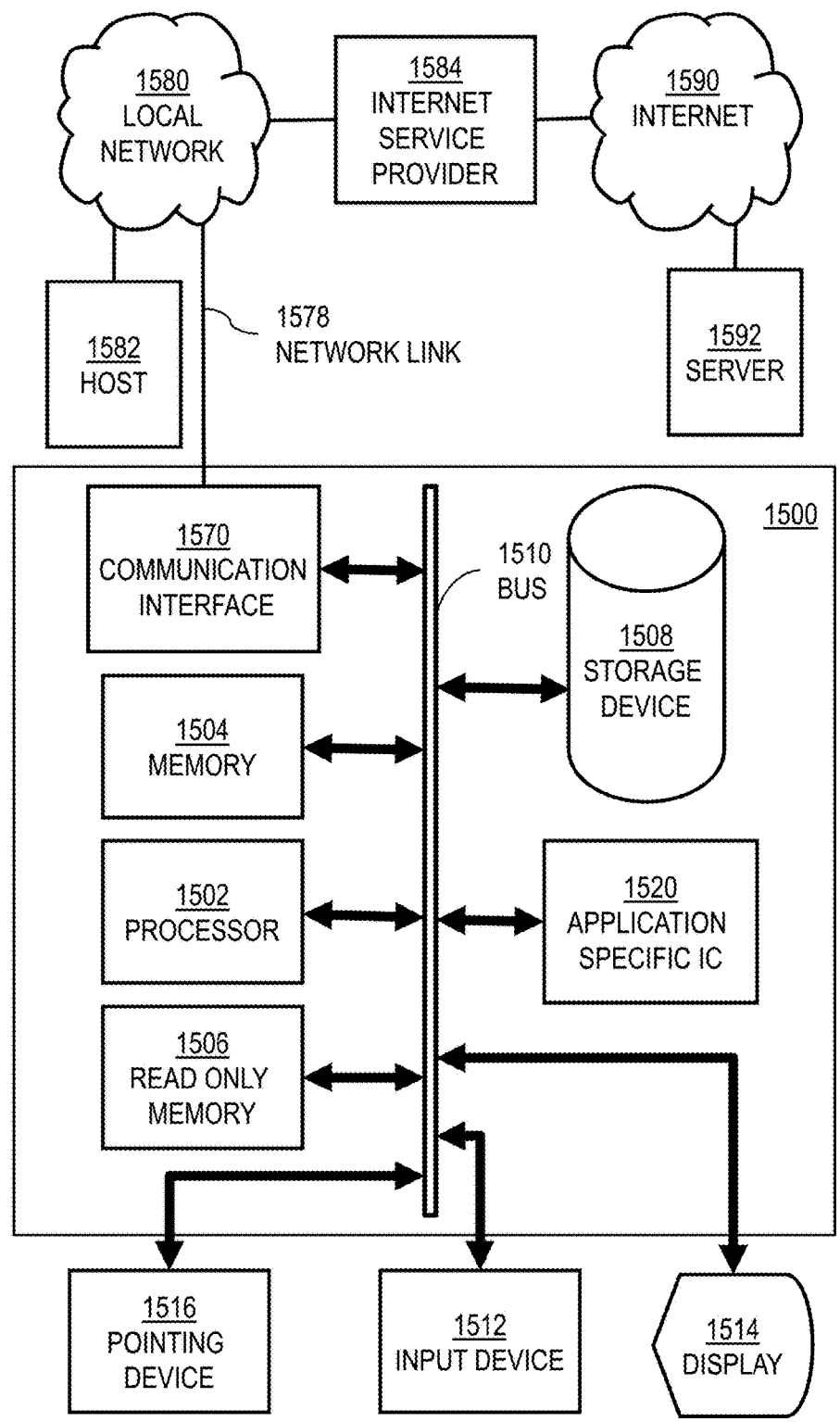
FIG. 15 is a block diagram that illustrates a computer system upon which an embodiment of the invention may be implemented.

FIG. 15 is a block diagram that illustrates a computer system 1500 upon which an embodiment of the invention may be implemented. Computer system 1500 includes a communication mechanism such as a bus 1510 for passing information between other internal and external components of the computer system 1500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1500, or a portion thereof, constitutes a means for performing one or more steps of one or more methods described herein.

A sequence of binary digits constitutes digital data that is used to represent a number or code for a character. A bus 1510 includes many parallel conductors of information so that information is transferred quickly among devices coupled to the bus 1510. One or more processors 1502 for processing information are coupled with the bus 1510. A processor 1502 performs a set of operations on information. The set of operations include bringing information in from the bus 1510 and placing information on the bus 1510. The set of operations also typically include comparing two or more units of information, shifting positions of units of information, and combining two or more units of information, such as by addition or multiplication. A sequence of operations to be executed by the processor 1502 constitute computer instructions.

Computer system 1500 also includes a memory 1504 coupled to bus 1510. The memory 1504, such as a random access memory (RAM) or other dynamic storage device, stores information including computer instructions. Dynamic memory allows information stored therein to be changed by the computer system 1500. RAM allows a unit of information stored at a location called a memory address to be stored and retrieved independently of information at neighboring addresses. The memory 1504 is also used by the processor 1502 to store temporary values during execution of computer instructions. The computer system 1500 also includes a read only memory (ROM) 1506 or other static storage device coupled to the bus 1510 for storing static information, including instructions, that is not changed by the computer system 1500. Also coupled to bus 1510 is a non-volatile (persistent) storage device 1508, such as a magnetic disk or optical disk, for storing information, including instructions, that persists even when the computer system 1500 is turned off or otherwise loses power.

Information, including instructions, is provided to the bus 1510 for use by the processor from an external input device 1512, such as a keyboard containing alphanumeric keys operated by a human user, or a sensor. A sensor detects conditions in its vicinity and transforms those detections into signals compatible with the signals used to represent information in computer system 1500. Other external devices coupled to bus 1510, used primarily for interacting with humans, include a display device 1514, such as a cathode ray tube (CRT) or a liquid crystal display (LCD), for presenting images, and a pointing device 1516, such as a mouse or a trackball or cursor direction keys, for controlling a position of a small cursor image presented on the display 1514 and issuing commands associated with graphical elements presented on the display 1514.

In the illustrated embodiment, special purpose hardware, such as an application specific integrated circuit (IC) 1520, is coupled to bus 1510. The special purpose hardware is configured to perform operations not performed by processor 1502 quickly enough for special purposes. Examples of application specific ICs include graphics accelerator cards for generating images for display 1514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1500 also includes one or more instances of a communications interface 1570 coupled to bus 1510. Communication interface 1570 provides a two-way communication coupling to a variety of external devices that operate with their own processors, such as printers, scanners and external disks. In general the coupling is with a network link 1578 that is connected to a local network 1580 to which a variety of external devices with their own processors are connected. For example, communication interface 1570 may be a parallel port or a serial port or a universal serial bus (USB) port on a personal computer. In some embodiments, communications interface 1570 is an integrated services digital network (ISDN) card or a digital subscriber line (DSL) card or a telephone modem that provides an information communication connection to a corresponding type of telephone line. In some embodiments, a communication interface 1570 is a cable modem that converts signals on bus 1510 into signals for a communication connection over a coaxial cable or into optical signals for a communication connection over a fiber optic cable. As another example, communications interface 1570 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1570 sends and receives electrical, acoustic or electromagnetic signals, including infrared and optical signals, which carry information streams, such as digital data.

The term computer-readable medium is used herein to refer to any medium that participates in providing information to processor 1502, including instructions for execution. Such a medium may take many forms, including, but not limited to, non-volatile media, volatile media and transmission media. Non-volatile media include, for example, optical or magnetic disks, such as storage device 1508. Volatile media include, for example, dynamic memory 1504. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1502, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1502, except for carrier waves and other signals.

Logic encoded in one or more tangible media includes one or both of processor instructions on a computer-readable storage media and special purpose hardware, such as ASIC 1520.

Network link 1578 typically provides information communication through one or more networks to other devices that use or process the information. For example, network link 1578 may provide a connection through local network 1580 to a host computer 1582 or to equipment 1584 operated by an Internet Service Provider (ISP). ISP equipment 1584 in turn provides data communication services through the public, world-wide packet-switching communication network of networks now commonly referred to as the Internet 1590. A computer called a server 1592 connected to the Internet provides a service in response to information received over the Internet. For example, server 1592 provides information representing video data for presentation at display 1514.

The invention is related to the use of computer system 1500 for implementing the techniques described herein. According to one embodiment of the invention, those techniques are performed by computer system 1500 in response to processor 1502 executing one or more sequences of one or more instructions contained in memory 1504. Such instructions, also called software and program code, may be read into memory 1504 from another computer-readable medium such as storage device 1508. Execution of the sequences of instructions contained in memory 1504 causes processor 1502 to perform the method steps described herein. In alternative embodiments, hardware, such as application specific integrated circuit 1520, may be used in place of or in combination with software to implement the invention. Thus, embodiments of the invention are not limited to any specific combination of hardware and software.

The signals transmitted over network link 1578 and other networks through communications interface 1570, carry information to and from computer system 1500. Computer system 1500 can send and receive information, including program code, through the networks 1580, 1590 among others, through network link 1578 and communications interface 1570. In an example using the Internet 1590, a server 1592 transmits program code for a particular application, requested by a message sent from computer 1500, through Internet 1590, ISP equipment 1584, local network 1580 and communications interface 1570. The received code may be executed by processor 1502 as it is received, or may be stored in storage device 1508 or other non-volatile storage for later execution, or both. In this manner, computer system 1500 may obtain application program code in the form of a signal on a carrier wave.

Various forms of computer readable media may be involved in carrying one or more sequence of instructions or data or both to processor 1502 for execution. For example, instructions and data may initially be carried on a magnetic disk of a remote computer such as host 1582. The remote computer loads the instructions and data into its dynamic memory and sends the instructions and data over a telephone line using a modem. A modem local to the computer system 1500 receives the instructions and data on a telephone line and uses an infra-red transmitter to convert the instructions and data to a signal on an infra-red a carrier wave serving as the network link 1578. An infrared detector serving as communications interface 1570 receives the instructions and data carried in the infrared signal and places information representing the instructions and data onto bus 1510. Bus 1510 carries the information to memory 1504 from which processor 1502 retrieves and executes the instructions using some of the data sent with the instructions. The instructions and data received in memory 1504 may optionally be stored on storage device 1508, either before or after execution by the processor 1502.

Figure 16:
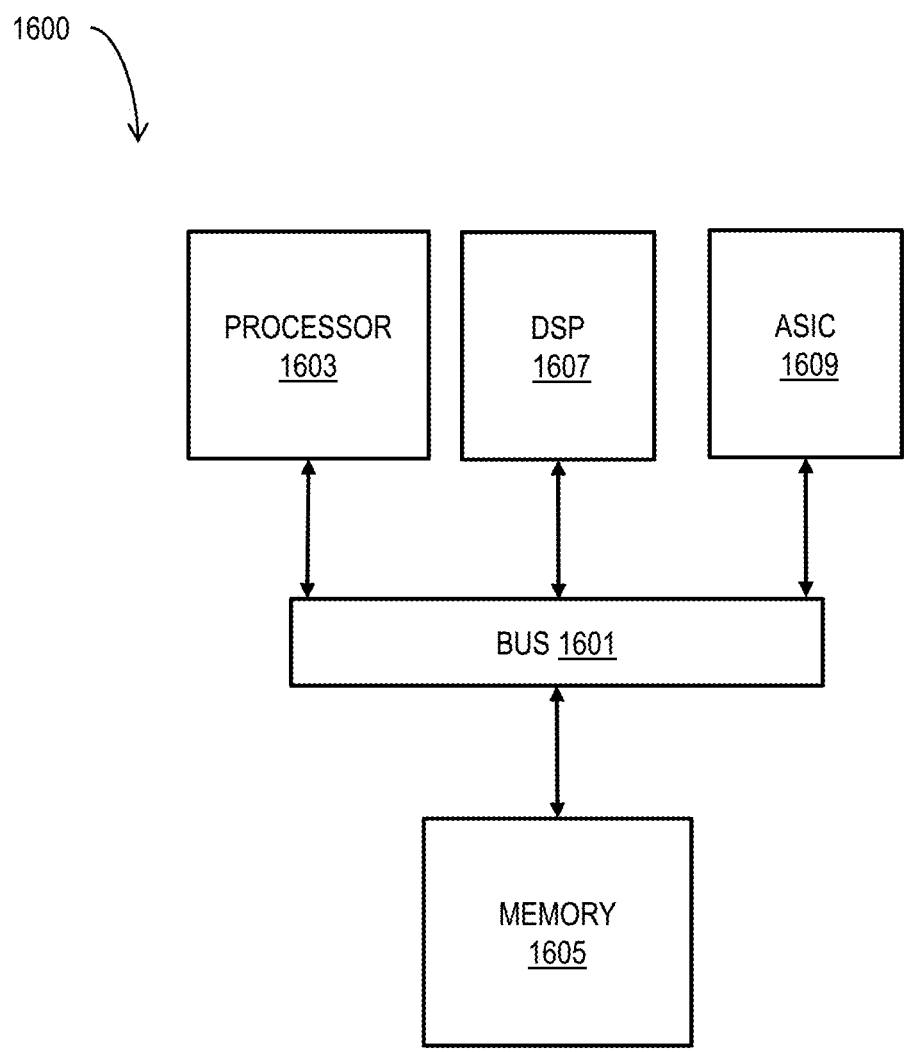
FIG. 16 illustrates a chip set upon which an embodiment of the invention may be implemented.

FIG. 16 illustrates a chip set 1600 upon which an embodiment of the invention may be implemented. Chip set 1600 is programmed to perform one or more steps of a method described herein and includes, for instance, the processor and memory components described with respect to FIG. 15 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1600, or a portion thereof, constitutes a means for performing one or more steps of a method described herein.

In one embodiment, the chip set 1600 includes a communication mechanism such as a bus 1601 for passing information among the components of the chip set 1600. A processor 1603 has connectivity to the bus 1601 to execute instructions and process information stored in, for example, a memory 1605. The processor 1603 may include one or more processing cores with each core configured to perform independently. A multi-core processor enables multiprocessing within a single physical package. Examples of a multi-core processor include two, four, eight, or greater numbers of processing cores. Alternatively or in addition, the processor 1603 may include one or more microprocessors configured in tandem via the bus 1601 to enable independent execution of instructions, pipelining, and multithreading. The processor 1603 may also be accompanied with one or more specialized components to perform certain processing functions and tasks such as one or more digital signal processors (DSP) 1607, or one or more application-specific integrated circuits (ASIC) 1609. A DSP 1607 typically is configured to process real-world signals (e.g., sound) in real time independently of the processor 1603. Similarly, an ASIC 1609 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1603 and accompanying components have connectivity to the memory 1605 via the bus 1601. The memory 1605 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1605 also stores the data associated with or generated by the execution of one or more steps of the methods described herein.

4. Extensions and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

5. Bibliography

Each of the following citations is hereby incorporated by reference as if fully set forth herein, except as the terminology is inconsistent with the terminology used herein.

[1] J. R. Lakowicz, K. Ray, M. Chowdhury, H. Szmacinski, Y. Fu, J. Zhang, K. Nowaczyk, Plasmon-controlled fluorescence: a new paradigm in fluorescence spectroscopy, Analyst 133 (2008) 1308-1346.

[2] W. Deng, E. M. Goldys, Plasmonic approach to enhanced fluorescence for applications in biotechnology and the life sciences, Langmuir 28 (2012) 10152-10163.

[3] J. R. Lakowicz, Radiative decay engineering 5: metal-enhanced fluorescence and plasmon emission, Anal. Biochem. 337 (2005) 171-194.

[4] S.-H. Cao, W.-P. Cai, Q. Liu, Y.-Q. Li, Surface plasmon-coupled emission: what can directional fluorescence bring to the analytical sciences?, Annu Rev. Anal. Chem. 5 (2012) 317-336.

[5] C.-F. Lai, H.-C. Kuo, P. Yu, T.-C. Lu, C.-H. Chao, H.-H. Yen, W.-Y. Yeh, Highly directional emission patterns based on near single guided mode extraction from GaN-based ultrathin microcavity light-emitting diodes with photonic crystals, Appl. Phys. Lett. 97 (2010) 013108.

[6] K. Ray, M. H. Chowdhury, J. R. Lakowicz, Aluminum nanostructured films as substrates for enhanced fluorescence in the ultraviolet-blue spectral region, Anal. Chem. 79 (2007) 6480-6487.

[7] N. Akbay, F. Madhavi, J. R. Lakowicz, K. Ray, Metal-enhanced intrinsic fluorescence of nucleic acids using platinum nanostructured substrates, Chem. Phys. Lett. 548 (2012) 45-50.

[8] X. Feng, F. Liu, Y. Huang, Spontaneous emission rate enhancement of silicon nanocrystals by plasmonic bandgap on copper grating, J. Lightwave Technol. 28 (2010) 1420-1430.

[9] Y. Zhang, K. Aslan, M. J. R. Previte, C. D. Geddes, Metal-enhanced fluorescence from copper substrates, Appl. Phys. Lett. 90 (2007) 173116.

[10] Y. Zhang, A. Dragan, C. D. Geddes, Broad wavelength range metal-enhanced fluorescence using nickel nanodeposits, J. Phys. Chem. C 113 (2009) 15811-5816.

[11] H. Szmacinski, Z. Murtaza, J. R. Lakowicz, Time-resolved fluorometric method for one-step immunoassays using plasmonic nanostructures, J. Phys. Chem. C 114 (2010) 7236-7241.

[12] W. Knoben, P. Offermans, S. H. Brongersma, M. Crego-Calama, Metal-induced fluorescence enhancement as a new detection mechanism for vapor sensing, Sens. Acutators. B 148 (2010) 307-314.

[13] L. Zhou, F. Ding, H. Chen, W. Ding, W. Zhang, S. Y. Chou, Enhancement of immunoassay's fluorescence and detection sensitivity using threedimensional plasmonic nano-antenna-dots array, Anal. Chem. 84 (2012) 4489-4495.

[14] F. Tang, N. Ma, L. Tong, F. He, L. Li, Control of metal-enhanced fluorescence with pH- and thermoresponsive hybrid microgels, Langmuir 28 (2012) 883-888.

[15] J. Zhao, X. Zhang, C. R. Yonzon, A. J. Haes, R. P. Van Duyne, Localized surface plasmon resonance biosensors, Nanomedicine 1 (2006) 219-228.

[16] S. J. Norton, T. Vo-Dinh, Plasmonics quenching and enhancement of a fluorescing molecule outside and inside a silver metallic nanoshell, IEEE Trans. Nanotechnol. 10 (2011) 1264-1274.

[17] W. Deng, K. Drozdowicz-Tomsia, D. Jin, E. M. Goldys, Enhanced flow cytometry based bead immunoassays using metal nanostructures, Anal. Chem. 81 (2009) 7248-7255.

[18] J. Zhang, Y. Fu, G. Li, R. Y. Zhao, J. R. Lakowicz, Detection of CXCR4 receptors on cell surface using a fluorescent metal nanoshell, J. Biomed. Opt. 16 (2011) 01611.

[19] P. Bharadwaj, L. Novotny, Spectral dependence of single molecule fluorescence enhancement, Opt. Express 15 (2007) 14266-14274.

[20] Y. Fu, J. Zhang, J. R. Lakowicz, Large enhancement of single molecule fluorescence by coupling to hollow silver nanoshells, Chem. Commun. 48 (2012) 9726-9728.

[21] A. Kinkhabwala, Z. Yu, Y. Avlasevich, K. Mullen, W. E. Moerner, Large single-molecule fluorescence enhancements produced by a bowtie nanoantenna, Nat. Photonics 3 (2009) 654-657.

[22] S. Thongrattanasiri, N. A. Kuhta, M. D. Escarra, A. J. Hoffman, C. F. Gmachi, V. A. Podolskiy, Analytical technique for subwavelength far field imaging, Appl. Phys. Lett. 97 (2010) 101103.

[23] M. H. Chowdhury, J. M. Catchmark, J. R. Lakowicz, Imaging three-dimensional light propagation through periodic nanohole arrays using scanning aperture microscopy, Appl. Phys. Lett. 91 (2007) 103118.

[24] S. Vedantam, H. Lee, J. Tang, J. Conway, M. Staffaroni, E. Yablonovitch, A plasmonic dimple lens for nanoscale focusing of light, Nano Lett. 9 (2009) 3447-3452.

[25] G. Rong, H. Wang, L. R. Skewis, R. M. Reinhard, Resolving sub-diffraction limit encounters in nanoparticle tracking using live cell plasmon coupling microscopy, Nano Lett. 8 (2008) 3386-3393.

[26] B. E. A. Saleh, M. C. Teich, Fundamentals of Photonics, second ed., Wiley-Interscience, New York, 2007.

[27] J. D. Joannopoulos, S. G. Johnson, J. N. Winn, R. D. Meade, Photonic Crystals: Molding the Flow of Light, second ed., Princeton University Press, Princeton, N.J., 2008.

[28] E. Yablonovitch, Inhibited spontaneous emission in solid-state physics and electronics, Phys. Rev. Lett. 58 (1987) 2059-2062.

[29] S. John, Strong localization of photons in certain disordered dielectric superlattices, Phys. Rev. Lett. 58 (1987) 2486-2489.

[30] P. Lodahl, F. van Driel, I. S. Nikolaev, A. Irman, K. Overgaag, D. Vanmaekelbergh, W. L. Vos, Controlling the dynamics of spontaneous emission from quantum dots by photonic crystals, Nature 430 (2004) 654-657.

[31] N. Ganesh, W. Zhang, P. C. Mathias, E. Chow, J. A. N. T. Soares, V. Malyarchuk, A. D. Smith, B. T. Cunningham, Enhanced fluorescence emission from quantum dots on a photonic crystal surface, Nat. Nanotechnol. 3 (2007) 515-520.

[32] I. S. Nikolaev, P. Lodahl, W. L. Vos, Fluorescence lifetime of emitters with broad homogeneous line-widths modified in optical photonic crystals, J. Phys. Chem. C 112 (2008) 7250-7254.

[33] S. Kubo, A. Fujishima, O. Sato, H. Segawa, Anisotropic accelerated emission of the chromophores in photonic crystals consisting of a polystyrene opal structure, J. Phys. Chem. C 113 (2009) 11704-11711.

[34] I.D. Block, P. C. Mathias, N. Ganesh, S. L. Jones, B. R. Dorvel, V. Chaudhery, L. O. Vodkin, R. Bashir, B. T. Cunningham, A detection instrument for enhanced fluorescence and label-free imaging on photonic crystal surfaces, Opt. Express 17 (2009) 13222-13235.

[35] C.-S. Huang, S. George, M. Lu, V. Chaudhery, R. Tan, R. C. Zangar, B. T. Cunningham, Application of photonic crystal enhanced fluorescence to cancer biomarker microarrays, Anal. Chem. 83 (2011) 1425-1430.

[36] R. V. Nair, R. Vijaya, Photonic crystal sensors: An overview, Prog. Quantum Electron. 34 (2010) 89-134.

[37] Y. Zhu, W. Xu, H. Zhang, W. Wang, L. Tong, S. Xu, Z. Sun, H. Song, Highly modified spontaneous emission in YVO4:Eu3+ inverse opal and refractive index sensing application, Appl. Phys. Lett. 100 (2012) 081104.

[38] I. A. Sukhoivanov, I. V. Guryev, J. A. A. Lucio, E. A. Mendez, M. Trejo-Duran, M. Torres-Cisneros, Photonic density of states maps for design of photonic crystal devices, Microelectron. J. 39 (2008) 685-689.

[39] M. Kaniber, A. Laucht, T. Hurlimann, M. Bichler, R. Meyer, M.-C. Amann, J. J. Finley, Highly efficient single-photon emission from single quantum dots within a two-dimensional photonic band-gap, Phys. Rev. B 77 (2008) 0733120.

[40] M. D. Meistikow, A. P. Mosk, E. Yeganegi, S. R. Huisman, A. Lagendijk, W. L. Vos, Inhibited spontaneous emission of quantum dots observed in a 3D photonic band gap, Phys. Rev. Lett. 107 (2011) 193903.

[41] J. Y. Ye, M. Ishikawa, Y. Yamane, N. Tsurumachi, H. Nakatsuka, Enhancement of two-photon excited fluorescence using one-dimensional photonic crystals, Appl. Phys. Lett. 75 (1999) 3605-3607.

[42] Y. Guo, C. Divin, A. Myc, F. L. Terry, J. R. Baker, T. B. Norris, J. Y. Ye, Sensitive molecular binding assay using a photonic crystal structure in total internal reflection, Opt. Express 16 (2008) 11741-11749.

[43] O. D. Velev, S. Gupta, Materials fabricated by micro- and nanoparticle assembly: the challenging path from science to engineering, Adv. Mater. 21 (2009) 1897-1905.

[44] J. H. Holtz, S. A. Asher, Polymerized colloidal crystal hydrogel films as intelligent chemical sensing materials, Nature 389 (1997) 829-832.

[45] V. L. Alexeev, A. C. Sharma, A. V. Goponenko, S. Das, I. K. Lednev, C. S. Wilcox, D. N. Finegold, S. A. Asher, High ionic strength glucose-sensing photonic crystal, Anal. Chem. 75 (2003) 2316-2323.

[46] J. R. Lakowicz, Radiative decay engineering 3: surface plasmon-coupled directional emission, Anal. Biochem. 324 (2004) 153-169.

[47] I. Gryczynski, J. Malicka, Z. Gryczynski, J. R. Lakowicz, Radiative decay engineering 4: experimental studies of surface plasmon-coupled directional emission, Anal. Biochem. 324 (2004) 170-182.

[48] J. Gao, A. M. Sarangan, Q. Zhan, Experimental confirmation of strong fluorescence enhancement using one-dimensional GaP/SiO2 photonic band gap structure, Opt. Mater. Express 1 (2011) 1216-1223.

[49] J. Y. Ye, M. Ishikawa, Enhancing fluorescence detection with a photonic crystal structure in a total-internal reflection configuration, Opt. Lett. 33 (2008) 1729-1731.

[50] Y. Ding, R. Magnusson, Resonant leaky-mode spectral-band engineering and device applications, Opt. Express 12 (2004) 5661-5674.

[51] N. Ganesh, I. D. Block, P. C. Mathias, W. Zhang, E. Chow, V. Malyarchuk, B. T. Cunningham, Leaky-mode assisted fluorescence excitation: application to fluorescence enhancement biosensors, Opt. Express 16 (2008) 21626-21640.

[52] F. Ramos-Mendieta, P. Halevi, Surface electromagnetic waves in twodimensional photonic crystals: effect of the position of the surface plane, Phys. Rev. B 59 (1999) 15112-15120.

[53] R. D. Meade, K. D. Brommer, A. M. Rappe, J. D. Joannopoulos, Electromagnetic Bloch waves at the surface of a photonic crystal, Phys. Rev. B 44 (1999) 44-49.

[54] M. Liscidini, J. E. Sipe, Enhancement of diffraction for biosensing applications via Bloch surface waves, Appl. Phys. Lett. 91 (2007) 253125.

[55] A. Farmer, A. C. Friedli, S. M. Wright, W. M. Robertson, Biosensing using surface electromagnetic waves in photonic band gap multilayers, Sens. Actuators B 173 (2012) 79-84.

[56] V. Paeder, V. Musi, L. Hvozdara, S. Herminjard, H. P. Herzig, Detection of protein aggregation with a Bloch surface wave based sensor, Sens. Actuators B 257 (2011) 260-264.

[57] A. Sinibaldi, N. Danz, E. Descrovi, P. Munzert, U. Schulz, F. Sonntag, L. Dominici, F. Michelotti, Direct comparison of the performance of Bloch surface wave and surface plasmon polariton sensors, Sens. Actuators B 174 (2012) 292-298.

[58] F. Giorgis, E. Descrovi, C. Summonte, L. Dominici, F. Michelotti, Experimental determination of the sensitivity of Bloch surface waves bases sensors, Opt. Express 18 (2010) 8087-8093.

[59] P. Rivolo, F. Michelotti, F. Frascella, G. Digregorio, P. Mandracci, L. Dominici, F. Giorgis, E. Descrovi, Real time secondary antibody detection by means of silicon-based multilayers sustaining Bloch surface waves, Sens. Actuators B 161 (2012) 1046-1052.

[60] F. Frascella, S. Ricciardi, P. Rivolo, V. Moi, F. Giorgis, E. Descrovi, F. Michelotti, P. Munzert, N. Danz, L. Napione, M. Alvaro, F. Bussolino, A fluorescent onedimensional photonic crystal for label-free biosensing based on Bloch surface waves, Sensors 13 (2013) 2011-2022.

[61] J. Y. Ye, M. Ishikawa, Enhancing fluorescence detection with a photonic crystal structure in a total-internal-reflection configuration, Opt. Lett. 33 (2008) 1729-1731.

[62] H. Inouye, M. Arakawa, J. Y. Ye, T. Hattori, Optical properties of a totalreflection-type one-dimensional photonic crystal, IEEE Explore 38 (2002) 867-871.

[63] M. Ballarini, F. Frascella, F. Michelotti, G. Digregorio, P. Rivolo, V. Paeder, V. Musi, F. Giorgis, E. Descrovi, Bloch surface wave-controlled emission of organic dyes grafted on a one-dimensional photonic crystal, Appl. Phys. Lett. 99 (2011) 043302.

[64] I. Gryczynski, J. Malicka, K. Nowaczyk, Z. Gryczynski, J. R. Lakowicz, Effects of sample thickness on the optical properties of surface plasmon-coupled emission, J. Phys. Chem. B 108 (2004) 12073-12083.

[65] J. R. Lakowicz, Radiative decay engineering: biophysical and biomedical applications, Anal. Biochem. 298 (2001) 1-24.

[66] J. R. Lakowicz, Y. Shen, S. D'Auria, J. Malicka, J. Fang, Z. Gryczynski, I. Gryczynski, Radiative decay engineering 2: effects of silver island films on fluorescence intensity, lifetimes, and resonance energy transfer, Anal. Biochem. 301 (2002) 261-277.

[67] F. Michelotti, A. Sinibaldi, P. Munzert, N. Danz, E. Descrovi, Probing losses of dielectric multilayers by means of Bloch surface waves, Opt. Lett. 38 (2013) 616-618.

[68] M. L. Brongersma, P. G. Kik (Eds.), Surface Plasmon Nanophotonics, Springer, New York, 2010.

[69] D. J. Griffiths, Introduction to Electrodynamics, Prentice Hall, Englewood Cliffs, N.J., 1999.

[70] A. Sinibaldi, E. Descrovi, F. Giorgis, L. Dominici, M. Ballarini, P. Mandracci, N. Danz, F. Michelotti, Hydrogenated amorphous silicon nitride photonic crystals for improved performance surface electromagnetic wave biosensors, Biomed. Opt. Exp. 3 (2012) 2405-2410.

[71] C. Ricciardi, V. Ballarini, M. Galli, M. Liscidini, L. C. Andreani, M. Losurdo, G. Bruno, S. Lettieri, F. Gesuele, P. Maddalena, F. Giorgis, Amorphous silicon nitride: a suitable alloy for optical multilayered structures, J. Non-Cryst. Solids 352 (2006) 1294-1297.

[72] A. Inoue, S. Inoue, S. Yokoyama, K. Kojima, K. Yasui, M. Ozawa, K. Odoi, One dimensional polymeric photonic crystal doped with second-order nonlinear optical chromophore, Proc. SPIE 7213 (2009) 72131C.

[73] P. Kurt, D. Banerjee, R. E. Cohen, M. F. Rubner, Structural color via layer-by-layer deposition: layered nanoparticle arrays with near-UV and visible reflectivity bands, J. Mater. Chem. 19 (2009) 8920-8927.

[74] M. Liscidini, J. E. Sipe, Analysis of Bloch-surface-wave assisted diffraction-based biosensors, J. Opt. Soc. Am. B 26 (2009) 279-289.

[75] E. Guillermain, V. Lysenko, R. Orobtchouk, T. Benyattou, S. Roux, A. Pillonnet, P. Perriat, Bragg surface wave device based on porous silicon and its application for sensing, Appl. Phys. Lett. 90 (2007) 241116.

[76] J. Gao, A. M. Saranagan, Q. Zhan, Polarization multiplexed fluorescence enhancer using a pixelated one-dimensional photonic band gap structure, Opt. Lett. 37 (2012) 2640-2642.

[77] E. Descrovi, T. Sfez, L. Dominici, W. Nakagawa, F. Michelotti, F. Giorgis, H.-P. Herzig, Near-field imaging of Bloch surface waves on silicon nitride onedimensional photonic crystals, Opt. Express 16 (2008) 5453-5464.

[78] S. D. Choudhury, R. Badugu, K. Nowaczyk, K. Ray, J. R. Lakowicz, Tuning fluorescence direction with plasmonic metal-dielectric-metal substrates, J. Phys. Chem. Lett. 4 (2013) 227-232.

[79] A. Angelini, E. Enrico, N. De Leo, P. Munzert, L. Boarino, F. Michelotti, F. Giorgis, E. Descrovi, Fluorescence diffraction assisted by Bloch surface waves on onedimensional photonic crystals, New J. Phys. 15 (2013) 073002.

[80] N. Vats, S. John, Theory of fluorescence in photonic crystals, Phys. Rev. A 65 (2002) 043808.

[81] I. S. Nikolaev, W. L. Vos, A. F. Koenderink, Accurate calculation of the local density of optical states in inverse-opal photonic crystals, J. Opt. Soc. Am. B 26 (2009) 987-997.

[82] M. Barth, A. Gruber, F. Cichos, Spectral and angular redistribution of photoluminescence near a photonic stop band, Phys. Rev. B 72 (2005) 085129.

[83] S. V. Boriskina, A. Gopinath, L. D. Negro, Optical gaps, mode patterns, and dipole radiation in two-dimensional aperiodic photonic structures, Phys. E 41 (2008) 1102-1106.

[84] A. F. Koenderink, M. Kafesaki, C. M. Soukoulis, V. Sandoghdar, Spontaneous emission in the near field of two-dimensional photonic crystals, Opt. Lett. 30 (2005) 3210-3212.

[85] Y. Cesa, C. Blum, J. M. van den Broek, A. P. Mosk, W. L. Vos, V. Subramaniam, Manipulation of the local density of photonic crystals to elucidate fluorescent protein emission rates, Phys. Chem. Chem. Phys. 11 (2009) 2525-2531.

[86] R. Sprik, B. A. Van Tiggelen, A. Lagendijk, Optical emission in periodic dielectrics, Europhys. Lett. 35 (1996) 265-270.

[87] R. Wagner, L. Heerklotz, N. Kortenbruck, F. Cichos, Back focal plane imaging spectroscopy of photonic crystals, Appl. Phys. Lett. 101 (2012) 081904.

[88] I. Frezza, M. Patrini, M. Liscidini, D. Comoretto, Directional enhancement of spontaneous emission in polymer flexible microcavities, J. Phys. Chem. C 115 (2011) 19939-19946.

[89] T. Sfez, E. Descrovi, L. Yu, M. Quaglio, L. Dominici, W. Nakagawa, F. Michelotti, F. Giorgis, P. Herzig, Two-dimensional optics on silicon nitride multilayer: refraction of Bloch surface waves, Appl. Phys. Lett. 96 (2010) 151101.

[90] E. Descrovi, T. Sfez, M. Quaglio, D. Brunazzo, L. Dominici, F. Michelotti, H. P. Herzig, O. J. F. Martin, F. Giorgis, Guided Bloch surface waves on ultrathin polymeric ridges, Nano Lett. 10 (2010) 2087-2091.

[91] C. V. Kelly, B. A. Baird, H. G. Craighead, An array of planar apertures for near-field fluorescence correlation spectroscopy, Biophys. J. 100 (2011) L34-L36.

[92] E. E. Schadt, S. Turner, A. Kasarskis, A window into third-generation sequencing, Hum. Mol. Genet. 19 (2010) R227-R240.

[93] R. J. P. Engelen, D. Mori, T. Baba, L. Kuipers, Subwavelength structure of the evanescent field of an optical Bloch wave, Phys. Rev. Lett. 102 (2009) 023902.

[94] S.-Y. Su, T. Yoshie, Optical surface edge Bloch modes: low-loss subwavelength scale two-dimensional light localization, Opt. Lett. 37 (2012) 4398-4400.

[95] R. Chatterjee, N. C. Panoiu, K. Liu, Z. Dios, M. B. Yu, M. T. Doan, L. J. Kaufman, R. M. Osgood, C. W. Wong, Achieving subdiffraction imaging through bound surface states in negative refraction photonic crystals in the near-infrared range, Phys. Rev. Lett. 100 (2008) 187401.

[96] L. C. Estrada, O. E. Martinez, M. Brunstein, S. Bouchoule, L. Le-Gratiet, A. Talneau, I. Sagnes, P. Monnier, J. A. Levenson, A. M. Yacomotti, Small volume excitation and enhancement of dye fluorescence on a 2D photonic crystal surface, Opt. Express 18 (2010) 3693-3699.

[97] R. Badugu, K. Nowaczyk, E. Descrovi, J. R. Lakowicz, Radiative decay engineering 6: Fluorescence on one-dimensional photonic crystals, Anal. Biochem. 442 (2013) 83-96.

[98] R. Badugu, E. Descrovi, J. R. Lakowicz, Radiative decay engineering 7: Tamm state-coupled emission using a hybrid plasmonic-photonic structure, Anal. Biochem. 445 (2014) 1-13.

What is claimed is:

1. A method for determining a concentration of a particular analyte comprising:
    providing a functionalized substrate for a target optical frequency comprising a one dimensional photonic crystal that is functionalized with a bioactive target molecule that has an affinity for a particular analytic, wherein the one dimensional photonic crystal comprises a plurality of dielectric layers including a plurality of high index of refraction layers alternating with a plurality of low index of refraction layers and the thickness of each layer is within a factor of four of a wavelength of the optical frequency in the layer;
    providing a reagent comprising a detection molecule for the particular analyte, wherein the detection molecule includes a fluorophore that fluoresces at the target optical frequency;
    determining a calibration curve that relates concentration of the particular analyte to at least one of intensity or direction or polarization of fluorescent emissions at the functionalized substrate in response to incident light for a plurality of known concentrations of the particular analyte mixed with the reagent,
    contacting a sample and the reagent to the functionalized substrate;
    obtaining measurements of at least one of intensity or direction or polarization of fluorescent emissions at the functionalized substrate in contact with the sample and reagent in response to the incident light; and
    determining a concentration of the particular analyte in the sample from the calibration curve and the measurements.

2. A method as recited in claim 1, wherein the target optical frequency is within a peak in a local radiative density of states (LRDoS) adjacent to a photonic band gap of the one dimensional photonic crystal.

3. A method as recited in claim 1, wherein obtaining measurements further comprises directing the incident light to impinge on the sample without passing through the one dimensional photonic crystal.

4. A method as recited in claim 3, wherein obtaining measurements further comprises directing the incident light normal to the plurality of dielectric layers in the one dimensional photonic crystal.

5. A method as recited in claim 3, wherein obtaining measurements further comprises directing the incident light polarized parallel to the plurality of dielectric layers in the one dimensional photonic crystal.

6. A method as recited in claim 1, wherein obtaining measurements further comprises directing the incident light to impinge on a surface of the one dimensional photonic crystal opposite the sample at an angle of minimum external reflection.

7. A method as recited in claim 6, wherein obtaining measurements further comprises directing the incident light polarized parallel to the plurality of dielectric layers in the one dimensional photonic crystal.

8. A method as recited in claim 1, wherein the angle of minimum external reflection depends on an index of refraction of a solution of the sample and the reagent.

9. A method as recited in claim 1, further comprising determining an angle of an emission intensity maximum independent of a direction of the incident light.

10. A method as recited in claim 9, wherein obtaining measurements further comprises collecting fluorescent emissions in a collection cone that includes the angle of the emission intensity maximum.

11. A method as recited in claim 9, wherein the angle of an emission intensity maximum is associated with a Bloch surface wave coupled emission (BWCE).

12. A method as recited in claim 9, wherein the angle of an emission intensity maximum is associated with a Bragg grating coupled emission (BGCE).

13. A method as recited in claim 1, wherein the functionalized substrate further comprises a glass prism abutting a surface of the one dimensional photonic crystal opposite a surface that the sample contacts.

14. A method as recited in claim 1, wherein:
    the substrate includes a top layer that comprises silica or alumina;
    the plurality of low index of refraction layers comprises $SiO_2$; and
    the plurality of high index of refraction layers comprises $Si_3N_4$.

15. A method as recited in claim 1, wherein a distance from the fluorophore to the one dimensional photonic crystal, when the detection molecule is bound to the bioactive target molecule, is less than a wavelength of the target optical frequency in the sample.

16. A method as recited in claim 1, wherein obtaining measurements further comprises directing the incident light with a wavelength of 580 nanometers in air to impinge on a surface of the one dimensional photonic crystal opposite the sample at an angle of 45.2 degrees from normal.

17. A functionalized substrate for a target optical frequency comprising a one dimensional photonic crystal that is functionalized with a bioactive target molecule that has an affinity for a particular analyte, wherein
    the one dimensional photonic crystal comprises a plurality of dielectric layers including a plurality of high index of refraction layers alternating with a plurality of low index of refraction layers, and
    the thickness of each layer is within a factor of four of a wavelength of the optical frequency in the layer,
    wherein the target optical frequency is within a peak in a local radiative density of states (LRDoS) adjacent to a photonic band gap of the one dimensional photonic crystal.

18. A functionalized substrate as recited in claim 17, further comprising a glass prism abutting a surface of the one dimensional photonic crystal opposite a functionalized surface with the bioactive target molecule.

19. A functionalized substrate as recited in claim 18, wherein:
the substrate includes a top layer that comprises silica or alumina;
the plurality of low index of refraction layers comprises $SiO_2$; and
the plurality of high index of refraction layers comprises $Si_3N_4$.

20. A functionalized substrate for a target optical frequency comprising a one dimensional photonic crystal that is functionalized with a bioactive target molecule that has an affinity for a particular analyte, wherein
the one dimensional photonic crystal comprises a plurality of dielectric layers including a plurality of high index of refraction layers alternating with a plurality of low index of refraction layers;
the thickness of each layer is within a factor of four of a wavelength of the optical frequency in the layer; and
for emissions from a fluorophore bound to the target molecule and excited by incident light, there is an emission intensity maximum centered at an angle independent of the direction of the incident light.

21. A fluorescence affinity assay kit for determining the quantity of a particular analyte, comprising:
a one dimensional photonic crystal comprising a plurality of dielectric layers including a plurality of high index of refraction layers alternating with a plurality of low index of refraction layers, wherein the thickness of each layer is within a factor of four of a wavelength of the optical frequency in the layer;
a solution comprising a bioactive target molecule that has affinity for a particular analyte, wherein the target molecule includes a ligand for affixing to the one dimensional photonic crystal to form a functionalized surface; and
a reagent comprising at least one plurality of substantively identical detection molecules, wherein the detection molecule comprises a fluorophore, and the detection molecule has affinity for the particular analyte.

22. A fluorescence affinity assay kit as recited in claim 21, wherein for emissions from a fluorophore bound to the target molecule on the one dimensional photonic crystal and excited by incident light, there is an emission intensity maximum centered at an angle independent of the direction of the incident light.

23. A fluorescence affinity assay kit as recited in claim 21, wherein the target optical frequency is within a peak in a local radiative density of states (LRDoS) adjacent to a photonic band gap of the one dimensional photonic crystal.

24. A fluorescence affinity assay kit as recited in claim 21, further comprising a glass prism abutting a surface of the one dimensional photonic crystal opposite the functionalized surface.

25. A fluorescence affinity assay kit as recited in claim 21, wherein:
the substrate includes a top layer that comprises silica or alumina;
the plurality of low index of refraction layers comprises $SiO_2$; and
the plurality of high index of refraction layers comprises $Si_3N_4$.

26. A system comprising:
a source of incident light,
a functionalized substrate that is to be placed in contact with a mixture of a sample and a reagent, wherein
the functionalized substrate comprises a one dimensional photonic crystal for a target optical frequency and a bioactive target molecule that has an affinity for a particular analyte,
the one dimensional photonic crystal comprises a plurality of dielectric layers including a plurality of high index of refraction layers alternating with a plurality of low index of refraction layers, and
the thickness of each layer is within a factor of four of a wavelength of the target optical frequency in the layer; and
the reagent comprises a detection molecule for the particular analyte wherein the detection molecule includes a fluorophore that fluoresces at the target optical frequency;
an optical coupler that directs incident light onto the functionalized substrate; and
a detector that measure fluorescent emissions from the functionalized substrate.

27. A system as recited in claim 26, wherein the target optical frequency is within a peak in a local radiative density of states (LRDoS) adjacent to a photonic band gap of the one dimensional photonic crystal.

28. A system as recited in claim 26, wherein the detector that collects fluorescent emissions in a collection cone that includes an angle of an emission intensity maximum that is independent of a direction of the incident light impinging on the substrate.

29. A system as recited in claim 28, wherein the angle of an emission intensity maximum is associated with a Bloch surface wave coupled emission (BWCE).

30. A system as recited in claim 28, wherein the angle of an emission intensity maximum is associated with a Bragg grating coupled emission (BGCE).

31. A system as recited in claim 26, the functionalized substrate further comprising a glass prism abutting a surface of the one dimensional photonic crystal opposite a functionalized surface with the bioactive target molecule.

32. A system as recited in claim 31, wherein the optical coupler directs the incident light to impinge on a surface of the one dimensional photonic crystal through the glass prism.

33. A system as recited in claim 32, wherein the optical coupler further comprises a polarizer that polarizes the incident light in a direction parallel to the plurality of dielectric layers.

34. A system as recited in claim 26, further comprising:
at least one processor; and
at least one memory including one or more sequences of instructions,
the at least one memory, and the one or more sequences of instructions and the at least one processor, cause the apparatus to perform at least the following,
determining a calibration curve that relates concentration of a particular analyte to at least one of intensity or direction or polarization of fluorescent emissions at the functionalized substrate in response to the incident light for a plurality of known concentrations of the particular analyte mixed with the reagent; and
determining a concentration of the particular analyte in a sample directly from the calibration curve and measurements of at least one of intensity or direction or polarization of fluorescent emissions at the functionalized substrate in contact with the sample and reagent in response to the incident light.

* * * * *